(12) United States Patent
Sabin

(10) Patent No.: US 7,449,196 B2
(45) Date of Patent: Nov. 11, 2008

(54) ANTI TUMOR COMPOSITIONS AND METHODS OF USE

(76) Inventor: Robert Sabin, P.O. Box 332, Goosedown Estate, Mill Neck, NY (US) 11765

( * ) Notice: Subject to any disclaimer, the term of this patent is extended or adjusted under 35 U.S.C. 154(b) by 342 days.

(21) Appl. No.: 10/888,576

(22) Filed: Jul. 9, 2004

(65) Prior Publication Data

US 2006/0008535 A1 Jan. 12, 2006

(51) Int. Cl.
| | |
|---|---|
| A61K 9/127 | (2006.01) |
| A61K 31/295 | (2006.01) |
| A61K 33/34 | (2006.01) |
| A61K 33/26 | (2006.01) |
| A61K 31/30 | (2006.01) |
| A61F 13/00 | (2006.01) |
| A01N 59/20 | (2006.01) |
| A01N 59/16 | (2006.01) |
| A01N 55/02 | (2006.01) |
| A01N 25/26 | (2006.01) |
| A01N 25/28 | (2006.01) |

(52) U.S. Cl. .................. 424/422; 424/417; 424/418; 424/450; 424/493; 424/630; 424/646; 514/499; 514/502

(58) Field of Classification Search ............... 424/417, 424/418, 422, 450, 493, 630, 646; 514/59, 514/499, 502
See application file for complete search history.

(56) References Cited

U.S. PATENT DOCUMENTS

| | | | |
|---|---|---|---|
| 2,924,551 A | 2/1960 | Harwood et al. | 167/22 |
| 4,101,669 A | 7/1978 | Baude et al. | 424/286 |
| 4,177,263 A | 12/1979 | Rosenberg et al. | |
| 4,193,993 A | 3/1980 | Hilditch | 424/141 |
| 4,569,836 A * | 2/1986 | Gordon | 424/1.37 |
| 4,670,429 A | 6/1987 | Dombay et al. | 514/187 |
| 4,745,129 A | 5/1988 | Ikari et al. | 514/502 |
| 4,952,607 A | 8/1990 | Sorenson et al. | 514/589 |
| 5,124,351 A | 6/1992 | Rabinovitz et al. | 514/499 |
| 5,202,353 A | 4/1993 | Schroth et al. | 514/500 |
| 5,624,668 A | 4/1997 | Lawrence et al. | 424/78.17 |
| 5,632,982 A | 5/1997 | Sussman et al. | 424/85.1 |
| 5,635,532 A | 6/1997 | Samid | 514/538 |
| 5,876,781 A | 3/1999 | Lasdon et al. | 426/633 |
| 6,225,489 B1 | 5/2001 | Fost et al. | 556/405 |
| 6,235,776 B1 | 5/2001 | Pamukcu et al. | |
| 6,248,712 B1 | 6/2001 | Dan.o slashed. et al. | 514/2 |
| 6,252,058 B1 | 6/2001 | Thompson | 536/24.1 |
| 6,258,774 B1 | 7/2001 | Stein et al. | 514/2 |
| 6,355,268 B1 | 3/2002 | Slater et al. | 424/450 |
| 6,465,008 B1 | 10/2002 | Slater et al. | 424/450 |
| 6,506,405 B1 | 1/2003 | Desai et al. | 424/450 |
| 6,534,096 B2 | 3/2003 | Shaw | |
| 6,537,988 B2 | 3/2003 | Lee | 514/221 |
| 6,703,050 B1 | 3/2004 | Brewer et al. | 424/641 |
| 6,706,759 B1 | 3/2004 | Kennedy | 514/499 |
| 6,747,148 B2 | 6/2004 | Peyman et al. | 544/122 |
| 2001/0051183 A1 | 12/2001 | Martin | 424/450 |
| 2002/0172711 A1 | 11/2002 | Martin | 424/450 |
| 2002/0198166 A1 | 12/2002 | Rothman et al. | 514/44 |
| 2003/0083367 A1 | 5/2003 | Murray et al. | 514/449 |
| 2003/0158249 A1 | 8/2003 | Chi et al. | 514/449 |
| 2003/0187039 A1 | 10/2003 | Favreau et al. | 514/365 |
| 2003/0195161 A1 | 10/2003 | Bissery | 514/27 |
| 2003/0195214 A1 | 10/2003 | Camden et al. | 514/242 |
| 2003/0198235 A1 | 10/2003 | Weldon et al. | 370/401 |
| 2003/0198638 A1 | 10/2003 | Watkins | 424/143.1 |
| 2003/0199469 A1 | 10/2003 | Schwartz et al. | 514/44 |
| 2004/0204385 A1 | 10/2004 | Leech | |
| 2004/0224005 A1 * | 11/2004 | Gabbay | 424/443 |

OTHER PUBLICATIONS

MedlinePlus Medical Encyclopedia: Cancer [online] Jul. 14, 2006 retrieved Oct. 18, 2006 retrieved from the internet http://www.nlm.nih.gov/medlineplus/ency/article/000583.htm pp. 1-3.*
MedlinePlus Medical Encyclopedia: Multiple Myeloma [online] Aug. 3, 2004 retrieved Oct. 18, 2006 retrieved from the internet http://www.nlm.nih.gov/medlineplus/ency/article/001289.htm pp. 1-4.*
Tabata et al. Journal of Controlled Release 1999, 59, 187-196.*
Szabo USA Today Killer Cancer Genes ID'd Sep. 7, 2006, pp. 1-2.*
Pan et al. Cancer Research 2002, 62, 4854-4859.*
Lowndes et al. Oncology Research 2004, 14, 529-539.*
Google internet search, [online] retrieved from the internet on Sep. 25, 2007, retrieved from www.google.com 3 pages.*
*Alza's Stealth® Liposomal Technology; Current Therapies and Future Opportunities*, Alza Corporation, Delivery Times Issues and Opinions, vol. II, Issue 1, 1-11, 2002.
*Consumers Guide to Cancer Drugs*, The American Cancer Society, Jones and Bartlett Publishers (previously supplied as a book) (2000) pp. 1-448.
*Cancer Facts and Figures 2003*, The American Cancer Society report, p. 4 (2003).
*It's Not About the Bike*, Armstrong, Lance, Berkley Publishing (previously supplied as a book) (2000).
*Copper ion-dependent damage to the base pairs in DNA in the presence of hydrogen peroxide*, Aruoma, Biochem. Jour., 273: 601-4 (1991) 1 page abstract.
*Intravenous Iron Optimizes the Response to Recombinant Human Erythropoietin in Cancer Patients with Chemotherapy-Related Anemia: A Multicenter. Open-Label, Randomized Trial*, Auerbach, J. of Clin. Oncology 227-1301-1307 (2004).

(Continued)

*Primary Examiner*—Johann Richter
*Assistant Examiner*—Ernst V Arnold
(74) *Attorney, Agent, or Firm*—Alfred M. Walker; Lee Grosskreuz Hechtel; Jennifer Yancy

(57) ABSTRACT

An anti-cancer composition having biocompatible materials, which can selectively exploit chemical variations between normal cells and cancer cells to inhibit or prevent the proliferation of cancerous cells and methods of use.

25 Claims, 50 Drawing Sheets

OTHER PUBLICATIONS

*Circulation and Biodistribution Profiles of Long-Circulating PEG Liposomes of Various Sizes in Rabbits*, Awasthi, Int. Journal of Pharmaceutics 253 (2003) 121-122.
*Cancer Chemotherapy Handbook*, Baquiran, Lippincott, p. 85 (2001) p. 85.
*An Indistinct Balance: The Safety and Efficacy of Parenteral Iron Therapy*, Besarab, Journal of American Society of Nephrology, vol. 10, No. 9, 23 pages (Sep. 1999).
*Angiogenesis and Cancer Control: From Concept to Therapeutic Trial*, Brem, Cancer Control Jour., 6 (5):436-458 (1999).
*Phase II Trial of Copper Depletion as Angiosuppresive Treatment in Newly Diagnosed Gliobastoma Multiforme: Final Report*, Brem, et al., Journal of Clinical Oncology vol. 22, No. 14S, (2004) 1 page abstract.
"Control of Copper in Wilson's Disease and Diseases of Neovascularization, such as Cancer", *Handbook of Copper Pharmacology and Toxicology*, Brewer, Humana Press, Chap. 27, (2002).
*Copper Control as an Antiangiogenic Anticancer Therapy: Lessons from Treating Wilson's Disease*, Brewer, Exp. Bio. and Med., 226(7):665-673 (2001).
*Treatment of Metastatic Cancer with Tetrathiomolybdate, an Anticopper, Antiangiogenesis Agent: Phase I Study*, Brewer, et al., Clin. Cancer Res., 6:1-10 (2000).
Applied and Envir. Microbio., Clarke et al., May 1987 pp. 917-922.
*Gallium in Cancer Treatment.*, Collery, et al., Crit. Rev. in Oncology/Hematology 42:283-296 (2002).
*Inhibition of the Growth of Squamous Cell Carcinoma by Tetrathiomolybdate-Induced Copper Supression in a Murine Model*, Cox, Merajver, Yoo, Dick, Brewer, Lee and Teknos, Arch Otolaryngol Head Neck Surg. 2003; 129:781-785 (2003) 1 page abstract.
*Structure of an iron-dextran complex*, Cox, J. of Pharma & Pharmac, 24:513-517 (1972).
*Physicians' Cancer Chemotherapy Drug Manual, 2003*, Chu & Devita, Jones and Bartlett Publishers, (2003) pp. 12-20.
*Glycolysis and GLUT1 in Breast Tumors: Markers of Response to Hormonal Therapy*, Degani, The American Society of Clinical Oncology, Intn'l J. of Cancer 107:177-182 (Nov. 2003),2 page summary in asco.org.
*Cancer in Metals and Metal Compounds: Part I—Carcinogenesis*, Desoize, B., Editor, Critical Reviews in Oncology/Hematology, 42:1-3 (2002).
*Cancer and Metals and Metal Compounds, Part II—Cancer Treatment*, Desoize, B. Editor, Crit. Rev. In Oncology/Hematology, 42:213-215 (2002).
(Iron Dextran Injection), USP, DEXFERRUM® American Regent, Inc., Package insert, (2004).
*Synthesis, cytotoxicity, and antitumor activity of copper (II) and Iron (III) complexes of (4)N-azabicyclo[3.1.2] nonane thiosemicarbazones derived from acyl diazines*, Easmon, J. Med. Chem, Jun. 2001, 44(13):2164-71, 2 page abstract.
*Hepatitis C Virus Infection and Non-Hodgkin Lymphoma: Results of the NCI-seer Multi-center Case-control Study*, Engels et al., Int. Journal of Cancer, vol. 111, Issue 1, 76-80 (2004) 3 page abstract.
*Advances in FDG PET Probes in Surgical Oncology*, Essner, et al., Cancer Jour. 8:100-108 (2002).
*The Role of Oxidative Stress in Mechanisms of Metal-Induced Carcinogenesis*, Galaris, et al., Critical Reviews In Oncology/Hematology, 42:93-103 (2002).
*The glycolysis phenotype in carcinogenesis and tumor invasion: insights through mathematical models*, Gatenby and Gawlinski, Cancer Res., 63(14):3847-54 (Jul. 2003).
*Why Do Cancers Have High Aerobio Glycolysis?*, Gatenby and Gillies, Nature Reviews Cancer, 4 (Nov. 2004).
*Novel Therapy for Liver Cancer: Direct Intraarterial Injection of a Potent Inhibitor of ATP Production*, Geschwind, Ko, Torbenson, Magee and Pedersen, Cancer Research 62, 3909-3913, Jul. 15, 2002.
*Cancer-Treating Cancer with Insulin Potentiation Therapy*, Hauser & Hauser, Boulah Land Press, (2001), pp. 1-414., (previously supplied as a book).

*Characteristics of Iron Dextran Utilization in Man*, Henderson & Hillman, Blood, 34(3):357-375 (1969).
*An Innovative Drug Delivery Technology*, Johnson, Magnetics Business & Technology Magazine, (2002).
Cancer Combat, King, (previously supplied as book).
Journal D'Agriculture Pratique, pp. 698-700, 728-729, and 765-766 (1887) (No translation).
*Paclitaxel analog kills more cancer cells than natural product*, Kingston, David, et al., American Chemical Society, Mar. 28, 2004.
*The Iron Metabolism of Neoplastic Cells: alterations that facilitate proliferation?*, Kwok, et al., Crit. Rev. In Oncology/Hematology 42:65-78 (2002).
Comparative Analysis of Copper and Iron Metabolism in Photosynthetic Eukaryotes vs. Yeast and Mammals, LaFontaine; Massaro, *Handbook of Copper Pharmacology and Toxicology*, Chapter 30, 481-503, 2002.
*Development and Comparison of Iron Dextran Products*, Lawrence, J. of Pharm. Sci. & Tech., 52(5):190-197 (1998).
*Glucose Metabolism in Cancer*, Lee and Pedersen, J. of Biol. Chem. 278 (42):41047-41058 (Oct. 2003).
*The Spraying of Plants*, Lodeman, the MacMillan Company, New York, N.Y. (1910).
*Hopes in cancer drug dashed*, Marchlone, Milwaukee Journal Sentinel, May 22, 2002.
*Basic Cancer Medicine*, Markman, M.D., W. B. Saunders Co., p. 103, (1997).
*2-deoxy-D-glucose increases the efficacy of adriamycin and paclitaxel in human osteosarcoma and non-small cell lung cancers in vivo*, Maschek, et al., Cancer Res., 64(1):31-34 (2004).
*Curing Metastatic Cancer: Lessons from Testicular Germ-Cell Tumours*, Masters and Koberle, Nature Reviews, 3(7) (Jul. 2003).
*Dextrans for targeted and sustained delivery of therapeutic and imaging agents*, Mehvar, J. of Controlled Release, 69:1-25 (2000).
*Recent Trends in the Use of Polysaccharides for Improved Delivery of Therapeutic Agents*, Mehvar, Pharmacokinetic and Pharmacodynamic Perspectives Current Pharmaceutical Biotechnology, 2003, 4, 283-302.
*The Discovery of the Bordeaux Mixture*, Millardet, (1885) translated by Schneiderman (1933) p. 13-15.
*Notes Sur Les Vignes Americaines et Opuscules Divers Sur le Merne Sujet*, Millardet, pp. 56-60 (1881) (No translation).
*Long-Circulating and Target-Specific Nanoparticles: Theory to Practice*, Moghimi, et al., Pharm. Rev., 53(2):283-318 (2001).
*Questioning Chemotherapy*, Moss, Equinox Press, p. 77, (2000).
*Cancer Therapy*, Moss, Equinox Press, p. 316 (1992).
The *Moss Reports Newsletter*, Moss, (Jul. 4, 2004), Ralph W. Moss, PhD. Weekly CancerDecisions.com Newsletter #139.
*Management of Hepatocellular Carcinoma*, Nakakura & Choti, Oncology, 14(7) (2000).
*Doxirubicin and Paclitaxel Comparable in Treatment of Metastatic Breast Cancer*, OncoLink, Reuters Health, Journal of Clinical Oncology, 2003; 21: 588-592.
*Copper Deficiency Induced by Tetrathiomolybdate Suppresses Tumor Growth and Angiogenesis*, Pan, et al., Cancer Res., 62:4854-4859 (2002).
"3-Bromopyruvate Slays Hepatoma Cells in Rabbits Without Damaging Normal Tissue", *Inhibiting glycolysis and oxidative phosphorylation. 3-BrPA abolishes cell ATP production*, Pedersen et al., Reuters News, (Jul. 18, 2002).
*CRC Handbook of Pest Management in Agriculture Volume III*, Pimentel, David, pp. 19-25, 49-59, 70-71, 75-93, 265, 366-369, 494-495, (1980).
*Cancer's Sweet Tooth*, Quillin, Nutrition Science News, (Apr. 2000).
*Beating Cancer with Nutrition*, Quillin, Nutrition Times Press, p. 225 (1998).
*Phase II Trial of Tetrathiomolybdate in Patients with Advanced Kidney Cancer*, Redman, Clin. Cancer Res., 9:1666-1672 (2003).
*The Red Devil*, Rich, Three Rivers Press, (1999), pp. 1-242, (previously supplied as a book).
*Iron Chelators as therapeutic agents for the Treatment of Cancer*, Richardson, Crit. Rev. in Oncology/Hematology 42:267-281 (2002).

*Glycolysis as a metabolic marker in orthotopic breast cancer, monitored by in vivo 13C MRS*, Rivenzon-Segal, et al., Amer. J. Phys. Endocrinology Metabolism, 283:E623-E630 (2002).

*DNA Damage Mediated by Metal Ions with Special Reference to Copper and Iron*, Sagripanti, Met. Ions Biol. Syst. 36:179-209 (1999).

*Virus Inactivation by Copper or Iron Ions alone and in the Presence of Peroxide*, Sagripanti, et al., Applied and Environ. Microbio, 59:12, 4374-4376 (1993).

*Metal- based Formulations with High Microbicidal Activity*, Sagripanti, Applied and Environ. Microbio, 58:9, 3157-3162 (1992).

*Site-specific Oxidative DNA Damage at Polyguanosines Produced by Copper Plus Hydrogen Peroxide*, Sagripanti and Kraemer, J. of Biol. Chem., 264(3):1729-1734 (1989).

*Comparison of Four Chemotherapy Regimens for Advanced Non-Small-Cell Lung Cancer*, Schiller, et al., The N. Eng. J. of Med., 346(2):92-98 (Jan. 2002).

"Research Proposal: New Approaches to Controlling Walnut Blight;" Schroth et al., 1984 pp. 1-4.

Information Disclosure Statement, Schroth, U.S. Appl. No. 07/644,997.

*Phase III, Trial of Doxorubicin, pacilitaxel, and the combination of doxorubicin and paclitaxel as front-line chemotherapy for metastatic breast cancer: an intergroup trial*, Sledge, et al., J. of Clinical Oncology, 21 (4):588-592 (Feb. 2003).

*Mechanisms and Genes of Cellular Suicide*, Steller, Hermann, Science 267 (5203):1445-1449 (1995).

*Body Iron Stores and the Risk of Cancer*, Stevens, et al., N. Eng. J. of Med., 319(16):1047-1052 (1988).

*Anti-Copper Therapy Protects Against Squamous Cell Cancer in Mice*, citing Cox et al, *Inhibition of the Growth of Squamous Cell Carcinoma by Tetrathiomolybdate-Induced Copper Suppression in a Murine Model*, Teknos, et al., Arch. of Otolaryngology: Head And Neck Surgery, in OrcoLink Cancer News, Reuters, 129:781-785 (2003).

*Copper and Carcinogenesis*, Theophanides, et al., Critical Reviews in Oncology/Hematology 42:57-64 (2002).

The Proc. of the Nat'l Acad. of Sci., Van Dang et al, 95:1511-1516 (1988).

*Administration of Liposomal Agents and Blood Clearance Capacity of the Mononuclear Phagocyte System*, Van Etten, Antimicrobial Agents and Chemotherapy, Jul. 1998, 1677-1681, vol. 42, No. 7.

"Cellular Responses to Copper in Aquatic Organisms", Viarengo, *Handbook of Copper Pharmacology and Toxicology*, Ed. Massaro, Humana Press, Chapter 25, 417-431, 2002.

*The Prime Cause and Prevention of Cancer*, Warburg, O., Konrad Tritsch, p. 6. (1969).

*On The Origin of Cancer Cells*, Warburg, O., Science 123 3191):309-314 (Feb. 1956).

*Human Lactoferrin: a Novel Therapeutic with Board Spectrum Potentia*, Weinberg, Pharmacy & Pharmacology, 53 (Oct. 2001).

*Iron and Cancer: a Dangerous Mix*, Weinberg, Iron Disorders Insight, 2(2):11 (1999).

*Development of Clinical Methods of Iron Deprivation for Suppression of Neoplastic and Infectious Diseases*, Weinberg, Cancer Investigation, 17(7):507-513 (1999).

*The Development of Awareness of the Carcinogenic Hazard of Inhaled Iron*, Weinberg, Oncology Res. 11:109-113 (1999).

*Iron Therapy and Cancer*, Weinberg, Kidney Int'l, 55(60):S131-134 (1999).

*The Role of Iron in Cancer*, Weinberg, Euro. J. Cancer Prevention, 5:19-36, (1995).

*Iron in Neoplastic Disease*, Weinberg, Nutrition Cancer, 4(3):223-33 (1993).

*The Development of Awareness of Iron Withholding Defense*, Weinberg, Perspectives in Biology and Medicine, Winter 1993, 36(2):215-221.

*Iron Loading and Disease Surveillance*, Weinberg, Emerging Infections Diseases, May-Jun. 1999, (5(3).

"Molecular Hardware of Copper Homeostasis in *Enderococlus hirae*", Wimmer, *Handbook of Copper Pharmacology and Toxicology*, Massar, Chapter 32, Humana Press, 2002, p. 527-542.

*The Copper Chelating Agent, trientine, suppresses tumor development and angiogenesis in the murine heptatocellular carcinoma cells*, Yoshiji, et al., Int'l J. of Cancer, 94:768-773 (2001).

*The copper chelating agent, Trientine attenuates liver enzymes-altered preneoplastic lesions in rats by angiogenesis suppression*, Yoshiji, et al., Oncology Rep., 10(5):1369-73 (2003).

*Hypoxia-inducible Factor I Activation by Aerobic Glycolysis Implicates the Warburg Effect in Carcinogenesis*, Lu et al., J. Biol. Chem., vol. 277, Issue 26, 23111-23115, Jun. 28, 2002, 10 pages.

*The Molecular formula and proposed structure of the irondextran complex, IMFERON*, London, J. of Pharmaceutical Sciences vol. 93, Issue 7, May 13, 2004, pp. 1838-1846.

Antman, Introduction: The History of Arsenic Trioxide in Cancer Therapy. The Oncologist, vol. 6 (Apr. 2001).

Miller, Taxanes and Platinum Drugs in Cancer Treatment. National Cancer Institute, (Dec. 2002).

Liposomal taxol formulation. Google Search (2007).

Scheindlin, The Duplicitous Nature of Inorganic Arsenic. American Society for Pharmacology and Experimental Therapeutics (2005).

Marani, Quest Goes On For All-Round Platinum Cancer Drug. http://www.cancerpage.com/news/article.asp?id=2907 (2007).

Wheate, DnA binding of the anti-cancer platinum complex. The Royal Society of Chemistry, (2003).

Disulfiram- Brand Name: Antabuse. http://healthyplace.com/medications/disufiram.htm, (2007).

Platinum Cancer Drugs. Google Search, (2007).

Billecke, Polynuclear platinum anticancer drugs are more potent then cisplatin and induce cell cycle arrest in glioma. Neuro-Oncology, (2006).

Medline News Today, Researchers Identify A New Class of Anti-Cancer Drugs Based on Platinum, VCU Massey Cancer Center. www.medlinenewstoday.com, (2006).

Friend B.S., Email Update. (Dec. 28, 2006).

Stedman, "Solution-definition," The American Heritage Stedman's Medical Dictionary, (2004) p. 769.

Stedman, "Core-definition." The American Heritage Stedman's Medical Dictionary, (2004) p. 187.

Reuters, Child Cancer Survivors Face Bad Health As Adults. http://articles.news.aol.com, (2006).

Kruglinski, From the Bruns Archive: The Deadly Rays That Cured Cancer. http://www.discover.com/issues/sep-06/features/burnsarchive/, (2006).

Brownlee, Bad Science+Breast Cancer. Discover, (2002).

Desoize, Particular aspects of platinum compounds used at present in cancer treament. Critical Reviews in Oncology/Hematology, (2002).

Pharmacosmos A/S, CosmoFer Iron Dextran. http://www.pharmcosmos.com/intravenousironinfusion/CosmoFer$_{13}$irondextran.html, (2007).

Poniard Pharmaceuticals, Picoplatin as Second-Line Therapy for Patients With Small Cell Lung Cancer. Clinicaltrials. gov, (2006).

Metals As Drugs/Anti-Cancer Drugs. http://www.portfolio.mvm.ed.ac.uk, (2006).

Desoize, Metals and Metal Compounds in Cancer Treatment. Anticancer Research, vol. 24 (2004).

Petsko, A Christmas Carol. http://genomebiology.com/2001/3/1/comment/1001.1, (2001).

VirtualOrchard.com, Champ Formula 2 (Copper Hydroxide). New Jersey Commercial Tree Fruit Production Guide, (1998).

Cupric hydroxide, Merck Index, (11th edition) No. 2650 p. 413.

Assay Designs Inc, Tumor Necrosis Factor-beta, http://www.assaydesigns.com/commerce/ccpa1015-4076-4076-tumor-necrosis-factor-beta..., (2007).

Assay Designs Inc, Tumor Necrosis Factor-alpha, Human recombinant. (Jan. 25, 2006).

TNF Cancer. Google Search, (2007).

Moss, Tumor Necrosis Factor. Cancer Therapy, (1992).

Cancer.com, Head and Neck Cancer: Cancer Encyclopedia. Answers.com, (2007).

National Cancer Institute Drug Dictionary, Paraplatin. www.cancer.gov, (2007).

Iron Dextran Complex CAS No. 9004-66-4, Second Annual Report on Carcinogens: Report on Carcinogens, 11th Edition, (1981).

Moss Reports, Cancer Decisions Newsletter Archives. (Aug. 20, 2006).
Moss Reports, Cancer Decisions Newsletter Archives. (Aug. 6, 2006).
Varmus, The New Era in Cancer Research. Science: www.sciencemag.org, (May 26, 2006) pp. 1162-1164.
Kiberstis, Frontiers in Cancer Research: Celebrating a Glass Half-Full. Science: www.sciencemag.org, (May 26, 2006), p. 1157.
Brody, Cancer Will Overtake Heart Disease as Leading Killer of Americans. The New York Times, (Feb. 1, 2005).
Wemstedt, The Nobel Prize in Physiology or Medicine 1926: Medicine Speech. http://nobelprize.org, (1927).
Cisplatin CAS No. 15663-27-1. Fifth Annual Report on Carcinogens: Report on Carcinogens, 11th Edition (1989).
Wang and Guo, Copper in Medicine: Homestasis, Chelation Therapy and Antitumor Drug Design. Current Medicinal Chemistry, (2003).
Borman, Targeting Telomerase: Researchers believe enzyme could be a nearly universal target for anticancer drugs. Chemical and Engineering News, vol. 84-No. 41 (2006) pp. 32-33.
Lung Cancer: Non-Small Cell Lung Cancer. (2003).
Iron Dextran. Google Search, (2007).
Auerbach, Intravenous Iron Optimizes the Response to Recombinant Human Erythropoietin in Cancer Patients With Chemotherapy-Related Anemia: A Multicenter, Open-Label, Randomized Trial. Journal of Clinical Onocology, vol. 22-No. 7 (2004).
Cancer Facts & Figures 2003. American Cancer Society, (2003).
Garber, Turning a Tumor's Lights Off. ScienceNOW Daily News, (2006).
Threshold Pharmaceuticals, Metabolic Targeting: Treating Disease by Targeting Abnormal Glucose Metabolism. http://www.thresholdpharm.com/sec/targeting, (2007).
Garber, Energy Boost: The Warburg Effect Returns in a New Theory of Cancer. Journal of the National Cancer Institute, vol. 96-No. 24 (2004) pp. 1805-1806.
Crymes, The De-regulation of Glycolysis in Cancer. Molecular Medicine Journal, (1999).
Wikipedia, List of IARC Group 2B carcinogens. http://www-cie.iarc.fr/ (2007).
Iron Dextran Carcinogen. Google Search, (2007).
Merck Index 11th Editioin p. 465 No. 2927.
NCI Cancer Bulletin, Cancer Incidence and Mortality—Interpreting the Data. NCI Cancer Bulletin, vol. 3-No. 48 (2006).
Meyer, Taming Cancer's Big 4 Killers: New Cancer Therapies and Kinder, Gentler than Traditio Treatments. AARP Bulletin, (Jun. 2002).
Fox, Cancer deaths finally on decline in the U.S.: survey. OncoLink Cancer News, (Jan. 2007).
Medline Plus, Medical Encyclopedia: Multiple myeloma. http://www.nlm.nih.gov/medlineplus/ency/article/000583.htm, (2004).
Bock and Doepel, NIH Researchers Discover "Feeding Channel". NIAID News, (Aug. 2000).
INFed (Iron Dextran Injection, USP).
Leaf, Why We're Losing The War On Cancer (And How To Win It). Fortune Magazine, (Mar. 2004) pp. 77-92.
Dexferrum (Iron Dextran Injection, USP). American Regent Laboratories, Inc.
Garber, Energy Deregulation: Licensing Tumors to Grow Science: www.sciencemag.org, vol. 312 (May 2006) pp. 1158-1159.
Liposomal taxol formulations. Google Patents, (2007).
Chu, Scientists isolate telomerase as cancer drug target. http://www.drugresearcher.com, (Sep. 2006).
Adfero, Ltd., Platinum anti-cancer drugs discovered. (Jan. 2006).

\* cited by examiner

CELL LINE: NCI-H23 LUNG
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]    =    708    ±    98 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 239280 | 83933 | 238572 | 83933 | 0 | 35 |
| DIS.COMP. | 0.003 | 327938 | 34095 | 327230 | 34095 | 0 | 14 |
| | 0.01 | 289465 | 62990 | 288757 | 62990 | 0 | 26 |
| | 0.03 | 269840 | 82815 | 269132 | 82815 | 0 | 35 |
| | 0.1 | 273782 | 88132 | 273074 | 88132 | 0 | 37 |
| | 0.3 | 243699 | 73717 | 242991 | 73717 | 0 | 31 |
| | 1 | 338981 | 43708 | 338273 | 43708 | 0 | 18 |
| | 3 | 273100 | 126786 | 272392 | 126786 | 0 | 53 |
| | 10 | 143339 | 64012 | 142631 | 64012 | 40 | 27 |
| BASE | | 297824 | 50646 | 297116 | 50646 | 0 | 21 |
| DOX | 1 µM | 1334 | 246 | 626 | 246 | 100 | 0 |

THEORETICAL CALCULATED ABSORBANCE VALUES

CELL LINE: NCI-H23 LUNG
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   596        ±        198 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 280621 | 45419 | 280026 | 45419 | 0 | 16 |
| DC+B | 0.003 | 293828 | 44679 | 293233 | 44679 | 0 | 16 |
|  | 0.01 | 257853 | 62646 | 257257 | 62646 | 8 | 22 |
|  | 0.03 | 246812 | 67879 | 246216 | 67879 | 12 | 24 |
|  | 0.1 | 298383 | 46767 | 297788 | 46767 | 0 | 17 |
|  | 0.3 | 288622 | 28595 | 288026 | 28595 | 9 | 10 |
|  | 1 | 217760 | 38288 | 217165 | 38288 | 22 | 14 |
|  | 3 | 2942 | 256 | 2347 | 256 | 99 | 0 |
|  | 10 | 566 | 185 | -30 | 185 | 100 | 0 |
| BASE |  | 254632 | 44431 | 254037 | 44431 | 9 | 16 |
| DOX | 1 µM | 1703 | 429 | 1107 | 429 | 100 | 0 |

Fig. 2E

| IC50 = 1.718 µg/mL |
|---|
| (THEORETICAL IC50 CALCULATED ABSORBANCE VALUE = 140013) |
| CONCENTRATIONS USED FOR REGRESSION 3.000 AND 1.000 µg/mL |
| REGRESSION OUTPUT |

| | |
|---|---|
| CONSTANT | 324573 |
| STD ERR OF Y EST | 27074 |
| R SQUARED | 1 |
| NO. OF OBSERVATIONS | 16 |
| DEGREES OF FREEDOM | 14 |
| X COEFFICENT(S) | -107409 |
| STD ERR OF COEF. | 6768 |

Fig. 2F

CELL LINE: NCI-H460 LUNG
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]  =  809  ±  298 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 114212 | 21835 | 113403 | 21835 | 0 | 19 |
| DIS.COMP. | 0.003 | 85678 | 43980 | 84869 | 43980 | 25 | 39 |
| | 0.01 | 79281 | 28129 | 78472 | 28129 | 31 | 25 |
| | 0.03 | 82290 | 25422 | 81481 | 25422 | 28 | 22 |
| | 0.1 | 81258 | 32786 | 80449 | 32786 | 29 | 29 |
| | 0.3 | 79020 | 29100 | 78211 | 29100 | 31 | 26 |
| | 1 | 62277 | 6501 | 61468 | 6501 | 46 | 6 |
| | 3 | 10113 | 4953 | 9304 | 4953 | 92 | 4 |
| | 10 | 1047 | 356 | 238 | 356 | 100 | 0 |
| BASE | | 80453 | 31751 | 79644 | 31751 | 30 | 28 |
| DOX | 1 µM | 1210 | 207 | 401 | 207 | 100 | 0 |

Fig. 3B

| IC50 = 1.183 µg/mL |
|---|
| (THEORETICAL IC50 CALCULATED ABSORBANCE VALUE = 56701) |
| CONCENTRATIONS USED FOR REGRESSION 3.000 AND 1.000 µg/mL |
| REGRESSION OUTPUT |
| CONSTANT                87550 <br> STD ERR OF Y EST        5779 <br> R SQUARED                1 <br> NO. OF OBSERVATIONS    16 <br> DEGREES OF FREEDOM     14 <br><br> X COEFFICENT(S)        -26082 <br> STD ERR OF COEF.       1445 |

Fig. 3C

CELL LINE: NCI-H460 LUNG
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   837   ±   284 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 63961 | 24027 | 63124 | 24027 | 0 | 38 |
| DC+B | 0.003 | 65444 | 19769 | 64607 | 19769 | 0 | 31 |
|  | 0.01 | 67894 | 19699 | 67057 | 19699 | 8 | 31 |
|  | 0.03 | 51046 | 20762 | 50209 | 20762 | 20 | 33 |
|  | 0.1 | 37264 | 14885 | 36427 | 14885 | 42 | 24 |
|  | 0.3 | 5788 | 1720 | 4951 | 1720 | 92 | 3 |
|  | 1 | 641 | 171 | -196 | 171 | 100 | 0 |
|  | 3 | 450 | 181 | -387 | 181 | 100 | 0 |
|  | 10 | 578 | 167 | -260 | 167 | 100 | 0 |
| BASE |  | 92220 | 18472 | 91383 | 18472 | 0 | 29 |
| DOX | 1 µM | 883 | 247 | 46 | 247 | 100 | 0 |

Fig. 3E

| IC50 = 0.131 µg/mL |  |
|---|---|
| (THEORETICAL IC50 CALCULATED ABSORBANCE VALUE = 31562) | |
| CONCENTRATIONS USED FOR REGRESSION 0.300 AND 0.100 µg/mL | |
| REGRESSION OUTPUT | |
| CONSTANT | 52165 |
| STD ERR OF Y EST | 10596 |
| R SQUARED | 1 |
| NO. OF OBSERVATIONS | 16 |
| DEGREES OF FREEDOM | 14 |
| X COEFFICENT(S) | -157381 |
| STD ERR OF COEF. | 26489 |

Fig. 3F

CELL LINE: MCF7 MAMMARY
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]  =  672  ±  83 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 163588 | 68466 | 162916 | 68466 | 0 | 42 |
| DIS.COMP. | 0.003 | 142391 | 71697 | 141719 | 71697 | 13 | 44 |
| | 0.01 | 179067 | 60307 | 178395 | 60307 | 0 | 37 |
| | 0.03 | 124765 | 62644 | 124093 | 62644 | 24 | 38 |
| | 0.1 | 119649 | 57326 | 118977 | 57326 | 27 | 35 |
| | 0.3 | 114224 | 48706 | 113552 | 48706 | 30 | 30 |
| | 1 | 118291 | 34321 | 117618 | 34321 | 28 | 21 |
| | 3 | 58684 | 29044 | 58012 | 29044 | 64 | 18 |
| | 10 | 16646 | 3030 | 15973 | 3030 | 90 | 2 |
| BASE | | 125715 | 61249 | 125043 | 61249 | 23 | 38 |
| DOX | 1 µM | 732 | 60 | 60 | 60 | 100 | 0 |

Fig. 4B

| IC50 = 2.213 µg/mL |
|---|
| (THEORETICAL IC50 CALCULATED ABSORBANCE VALUE = 81458) |
| CONCENTRATIONS USED FOR REGRESSION 3.000 AND 1.000 µg/mL |
| REGRESSION OUTPUT |
| CONSTANT                147421<br>STD ERR OF Y EST         31792<br>R SQUARED                     1<br>NO. OF OBSERVATIONS           16<br>DEGREES OF FREEDOM            14<br><br>X COEFFICENT(S)          -29803<br>STD ERR OF COEF.           7948 |

Fig. 4C

CELL LINE: MCF7 MAMMARY
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]    =    1450    ±    1255 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 180297 | 67048 | 178847 | 67048 | 0 | 37 |
| DC+B | 0.003 | 200182 | 40578 | 198732 | 40578 | 0 | 23 |
|  | 0.01 | 202789 | 64075 | 201339 | 64075 | 0 | 36 |
|  | 0.03 | 197598 | 28199 | 196148 | 28199 | 0 | 16 |
|  | 0.1 | 150016 | 66716 | 148567 | 66716 | 17 | 37 |
|  | 0.3 | 195335 | 28074 | 193885 | 28074 | 0 | 16 |
|  | 1 | 86580 | 38955 | 85130 | 38955 | 52 | 22 |
|  | 3 | 1046 | 212 | -404 | 212 | 100 | 0 |
|  | 10 | 482 | 146 | -968 | 146 | 100 | 0 |
| BASE |  | 283739 | 80230 | 282289 | 80230 | 0 | 45 |
| DOX | 1 µM | 555 | 233 | -895 | 233 | 100 | 0 |

Fig. 4E

| IC50 = 0.972 µg/mL |  |
|---|---|
| (THEORETICAL IC50 CALCULATED ABSORBANCE VALUE = 89423) | |
| CONCENTRATIONS USED FOR REGRESSION 1.000 AND 0.300 µg/mL | |
| REGRESSION OUTPUT | |
| CONSTANT | 240494 |
| STD ERR OF Y EST | 33953 |
| R SQUARED | 1 |
| NO. OF OBSERVATIONS | 16 |
| DEGREES OF FREEDOM | 14 |
| X COEFFICENT(S) | -155363 |
| STD ERR OF COEF. | 24252 |

Fig. 4F

CELL LINE: ZR-75-1 MAMMARY
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   592   ±   178 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 108103 | 43069 | 107510 | 43069 | 0 | 40 |
| DIS.COMP. | 0.003 | 132348 | 14569 | 131755 | 14569 | 0 | 14 |
|  | 0.01 | 119250 | 30534 | 118658 | 30534 | 0 | 28 |
|  | 0.03 | 124791 | 29590 | 124199 | 29590 | 0 | 28 |
|  | 0.1 | 113021 | 40121 | 112429 | 40121 | 0 | 37 |
|  | 0.3 | 112641 | 21194 | 112049 | 21194 | 0 | 20 |
|  | 1 | 94331 | 8863 | 93738 | 8863 | 13 | 8 |
|  | 3 | 97565 | 17244 | 96972 | 17244 | 10 | 16 |
|  | 10 | 70952 | 24346 | 70359 | 24346 | 35 | 23 |
| BASE |  | 127525 | 14303 | 126933 | 14303 | 0 | 13 |
| DOX | 1 µM | 937 | 171 | 345 | 171 | 100 | 0 |

THEORETICAL CALCULATED ABSORBANCE VALUES

CELL LINE: ZR-75-1 MAMMARY
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND] = 655 ± 149 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 76148 | 14755 | 75493 | 14755 | 0 | 20 |
| DC+B | 0.003 | 94190 | 22989 | 93535 | 22989 | 0 | 30 |
| | 0.01 | 102582 | 21922 | 101927 | 21922 | 0 | 29 |
| | 0.03 | 94237 | 25930 | 93582 | 25930 | 0 | 34 |
| | 0.1 | 89610 | 16748 | 88955 | 16748 | 0 | 22 |
| | 0.3 | 89812 | 13449 | 89157 | 13449 | 0 | 18 |
| | 1 | 66568 | 10830 | 65913 | 10830 | 13 | 14 |
| | 3 | 11946 | 1708 | 11291 | 1708 | 85 | 2 |
| | 10 | 663 | 169 | 8 | 169 | 100 | 0 |
| BASE | | 93992 | 23394 | 93337 | 23394 | 0 | 31 |
| DOX | 1 µM | 607 | 175 | -48 | 175 | 100 | 0 |

Fig. 5E

| IC50 = 2.031 µg/mL |
|---|
| (THEORETICAL IC50 CALCULATED ABSORBANCE VALUE = 37746) |
| CONCENTRATIONS USED FOR REGRESSION 3.000 AND 1.000 µg/mL |
| REGRESSION OUTPUT |
| CONSTANT 93223 |
| STD ERR OF Y EST 7753 |
| R SQUARED 1 |
| NO. OF OBSERVATIONS 16 |
| DEGREES OF FREEDOM 14 |
| X COEFFICENT(S) -27311 |
| STD ERR OF COEF. 1938 |

Fig. 5F

CELL LINE: PC-3 PROSTATE
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   912   ±   286 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 49491 | 15714 | 48579 | 15714 | 0 | 32 |
| DIS.COMP. | 0.003 | 56721 | 19439 | 55808 | 19439 | 0 | 40 |
| | 0.01 | 41732 | 17624 | 40819 | 17624 | 0 | 36 |
| | 0.03 | 57453 | 21988 | 56540 | 21988 | 0 | 45 |
| | 0.1 | 57074 | 24963 | 56161 | 24963 | 16 | 51 |
| | 0.3 | 56819 | 22170 | 55906 | 22170 | 0 | 46 |
| | 1 | 80203 | 19183 | 79290 | 19183 | 0 | 39 |
| | 3 | 90242 | 20098 | 89329 | 20098 | 0 | 41 |
| | 10 | 41161 | 9452 | 40249 | 9452 | 17 | 19 |
| BASE | | 53951 | 15624 | 53039 | 15624 | 0 | 32 |
| DOX | 1 µM | 1801 | 382 | 889 | 382 | 98 | 1 |

Fig. 6B

| IC50 >   10   µg/mL |
|---|

| THEORETICAL CALCULATED ABSORBANCE VALUES |
|---|
| IC10  =  43721 |
| IC50  =  24289 |
| IC90  =  4858 |

Fig. 6C

CELL LINE: PC-3 PROSTATE
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   982   ±   328 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 75060 | 6681 | 74078 | 6681 | 0 | 9 |
| DC+B | 0.003 | 76246 | 12881 | 75263 | 12881 | 0 | 17 |
|  | 0.01 | 76914 | 8723 | 66317 | 28367 | 10 | 38 |
|  | 0.03 | 76769 | 15501 | 75786 | 15501 | 0 | 21 |
|  | 0.1 | 75635 | 6312 | 74653 | 6312 | 0 | 9 |
|  | 0.3 | 75745 | 10158 | 74763 | 10158 | 0 | 14 |
|  | 1 | 60357 | 9393 | 59375 | 9393 | 20 | 13 |
|  | 3 | 8963 | 1479 | 7980 | 1479 | 89 | 2 |
|  | 10 | 844 | 420 | -138 | 420 | 100 | 1 |
| BASE |  | 76812 | 6491 | 75829 | 6491 | 0 | 9 |
| DOX | 1 µM | 1942 | 210 | 960 | 210 | 99 | 0 |

Fig. 6E

| IC50 = 1.869 µg/mL |
|---|
| (THEORETICAL IC50 CALCULATED ABSORBANCE VALUE = 37039) |
| CONCENTRATIONS USED FOR REGRESSION 3.000 AND 1.000 µg/mL |
| REGRESSION OUTPUT<br><br>CONSTANT                     85072<br>STD ERR OF Y EST          6723<br>R SQUARED                      1<br>NO. OF OBSERVATIONS       16<br>DEGREES OF FREEDOM        14<br><br>X COEFFICENT(S)          -25697<br>STD ERR OF COEF.           1681 |

Fig. 6F

CELL LINE: DLD-1 COLON
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   768   ±   118 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 162684 | 18161 | 161917 | 18161 | 0 | 11 |
| DIS.COMP. | 0.003 | 107941 | 77585 | 107174 | 77585 | 34 | 48 |
| | 0.01 | 117770 | 65709 | 117003 | 65709 | 28 | 41 |
| | 0.03 | 117510 | 55001 | 116742 | 55001 | 28 | 34 |
| | 0.1 | 144989 | 38297 | 144222 | 38297 | 11 | 24 |
| | 0.3 | 100932 | 64511 | 100164 | 64511 | 38 | 40 |
| | 1 | 89095 | 58265 | 88327 | 58265 | 45 | 36 |
| | 3 | 54829 | 19219 | 54062 | 19219 | 67 | 12 |
| | 10 | 9397 | 4807 | 8629 | 4807 | 95 | 3 |
| BASE | | 161024 | 20830 | 160256 | 20830 | 1 | 13 |
| DOX | 1 µM | 1322 | 279 | 554 | 279 | 100 | 0 |

Fig. 7B

| IC50 = 1.430 µg/mL |
|---|
| (THEORETICAL IC50 CALCULATED ABSORBANCE VALUE = 80958) |
| CONCENTRATIONS USED FOR REGRESSION 3.000 AND 1.000 µg/mL |
| REGRESSION OUTPUT |
| CONSTANT                              105460 <br> STD ERR OF Y EST                 43383 <br> R SQUARED                                      0 <br> NO. OF OBSERVATIONS              16 <br> DEGREES OF FREEDOM             14 <br><br> X COEFFICENT(S)                    -17133 <br> STD ERR OF COEF.                  10846 |

Fig. 7C

CELL LINE: DLD-1 COLON
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]  =  433  ±  168 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 60191 | 22276 | 59758 | 22276 | 0 | 37 |
| DC+B | 0.003 | 42077 | 20759 | 41644 | 20759 | 30 | 35 |
|  | 0.01 | 70053 | 29529 | 69620 | 29529 | 0 | 49 |
|  | 0.03 | 44268 | 20110 | 43835 | 20110 | 27 | 34 |
|  | 0.1 | 41289 | 25848 | 40857 | 25848 | 32 | 43 |
|  | 0.3 | 18399 | 7678 | 17966 | 7678 | 70 | 13 |
|  | 1 | 7224 | 3177 | 6792 | 3177 | 89 | 5 |
|  | 3 | 564 | 129 | 131 | 129 | 100 | 0 |
|  | 10 | 550 | 328 | 117 | 328 | 100 | 1 |
| BASE |  | 103470 | 32460 | 103037 | 32460 | 0 | 54 |
| DOX | 1 µM | 1481 | 248 | 1049 | 248 | 98 | 0 |

Fig. 7E

| IC50 = 0.196 µg/mL |  |
|---|---|
| (THEORETICAL IC50 CALCULATED ABSORBANCE VALUE = 29879) | |
| CONCENTRATIONS USED FOR REGRESSION 0.300 AND 0.100 µg/mL | |
| REGRESSION OUTPUT | |
| CONSTANT | 52302 |
| STD ERR OF Y EST | 19067 |
| R SQUARED | 1 |
| NO. OF OBSERVATIONS | 16 |
| DEGREES OF FREEDOM | 14 |
| X COEFFICENT(S) | -114452 |
| STD ERR OF COEF. | 47667 |

Fig. 7F

CELL LINE: OVCAR-3 OVARIAN
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   793   ±   114 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 21419 | 14475 | 20626 | 14475 | 0 | 70 |
| DIS.COMP. | 0.003 | 19835 | 15417 | 19042 | 15417 | 8 | 75 |
| | 0.01 | 18879 | 12780 | 18086 | 12780 | 12 | 62 |
| | 0.03 | 25350 | 8809 | 24557 | 8809 | 0 | 43 |
| | 0.1 | 25419 | 10790 | 24626 | 10790 | 0 | 52 |
| | 0.3 | 23016 | 8915 | 22223 | 8915 | 0 | 43 |
| | 1 | 17291 | 12124 | 16498 | 12124 | 20 | 59 |
| | 3 | 12085 | 5735 | 11292 | 5735 | 45 | 28 |
| | 10 | 1725 | 634 | 932 | 634 | 95 | 3 |
| BASE | | 25258 | 12252 | 24465 | 12252 | 0 | 59 |
| DOX | 1 µM | 1441 | 207 | 648 | 207 | 97 | 1 |

Fig. 8B

| IC50 = 3.662 µg/mL |
|---|
| (THEORETICAL IC50 CALCULATED ABSORBANCE VALUE = 10313) |
| CONCENTRATIONS USED FOR REGRESSION 10.300 AND 3.000 µg/mL |
| REGRESSION OUTPUT |
| CONSTANT 15733<br>STD ERR OF Y EST 4080<br>R SQUARED 1<br>NO. OF OBSERVATIONS 16<br>DEGREES OF FREEDOM 14<br><br>X COEFFICENT(S) -1480<br>STD ERR OF COEF. 291 |

Fig. 8C

CELL LINE: OVCAR-3 OVARIAN
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   635   ±   156 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 18870 | 7517 | 18235 | 7517 | 0 | 41 |
| DC+B | 0.003 | 16804 | 4167 | 16169 | 4167 | 11 | 23 |
|  | 0.01 | 21353 | 6899 | 20718 | 6899 | 0 | 38 |
|  | 0.03 | 19334 | 4315 | 18699 | 4315 | 0 | 24 |
|  | 0.1 | 16488 | 5282 | 15853 | 5282 | 13 | 29 |
|  | 0.3 | 9722 | 2501 | 9087 | 2501 | 50 | 14 |
|  | 1 | 1903 | 510 | 1268 | 510 | 93 | 3 |
|  | 3 | 422 | 69 | -214 | 69 | 100 | 0 |
|  | 10 | 596 | 105 | -39 | 105 | 100 | 1 |
| BASE |  | 17687 | 4190 | 17052 | 4190 | 6 | 23 |
| DOX | 1 µM | 1090 | 233 | 455 | 233 | 98 | 1 |

Fig. 8E

| IC50 = 0.299 µg/mL |
|---|
| (THEORETICAL IC50 CALCULATED ABSORBANCE VALUE = 9118) |
| CONCENTRATIONS USED FOR REGRESSION 0.300 AND 0.100 µg/mL |
| REGRESSION OUTPUT |
| CONSTANT                              19237<br>STD ERR OF Y EST                4133<br>R SQUARED                                      0<br>NO. OF OBSERVATIONS        16<br>DEGREES OF FREEDOM         14<br><br>X COEFFICENT(S)                 -33834<br>STD ERR OF COEF.              10332 |

Fig. 8F

CELL LINE: CAKI-1 RENAL
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   870.000   ±   235.511 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 45398 | 5160 | 44528 | 5160 | 0.0 | 11.6 |
| DIS.COMP. | 0.003 | 42038 | 5884 | 41168 | 5884 | 7.5 | 13.2 |
| | 0.01 | 36374 | 14961 | 35504 | 14961 | 20.3 | 33.6 |
| | 0.03 | 38682 | 9289 | 37812 | 9289 | 15.1 | 20.9 |
| | 0.1 | 35966 | 15199 | 35096 | 15199 | 21.2 | 34.1 |
| | 0.3 | 24042 | 7441 | 23172 | 7441 | 48.0 | 16.7 |
| | 1 | 26367 | 7624 | 25497 | 7624 | 42.7 | 17.1 |
| | 3 | 11765 | 7206 | 10895 | 7206 | 75.5 | 16.2 |
| | 10 | 8181 | 919 | 7311 | 919 | 83.6 | 2.1 |
| BASE | | 42572 | 6530 | 41702 | 6530 | 6.3 | 14.7 |
| DOX | 1 µM | 730 | 195 | -140 | 195 | 100.0 | 0.4 |

Fig. 9B

| IC50 = 1.44 µg/mL |
|---|
| (THEORETICAL IC50 CALCULATED ABSORBANCE VALUE = 22263.938) |
| CONCENTRATIONS USED FOR REGRESSION 3.00 AND 1.00 µg/mL |
| REGRESSION OUTPUT |
| CONSTANT                3.28E+04<br>STD ERR OF Y EST         7.42E+03<br>R SQUARED               5.25E-01<br>  NO. OF OBSERVATIONS          16<br>  DEGREES OF FREEDOM           14<br><br>X COEFFICENT(S)          -7.30E+03<br>STD ERR OF COEF.         1.85E+03 |

Fig. 9C

CELL LINE: CAKI-1 RENAL
CELLS PLATED: 5.0E+03 CELLS/WELL
TREATMENT DAY 1 POST PLATING, CONTINUOUS EXPOSURE

*TERMINATOR + BASE (60 µg/mL)*

( MEDIA + MTS [BACKGROUND]   =   522   ±   198 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 24112 | 1386 | 23590 | 1386 | 0 | 6 |
| DC+B | 0.003 | 26995 | 4082 | 26473 | 4082 | 0 | 17 |
| | 0.01 | 24148 | 3290 | 23626 | 3290 | 0 | 14 |
| | 0.03 | 24409 | 3976 | 23887 | 3976 | 0 | 17 |
| | 0.1 | 25371 | 5959 | 24849 | 5959 | 0 | 25 |
| | 0.3 | 18333 | 3081 | 17811 | 3081 | 24 | 13 |
| | 1 | 13138 | 4040 | 12616 | 4040 | 47 | 17 |
| | 3 | 1223 | 261 | 701 | 261 | 97 | 1 |
| | 10 | 757 | 194 | 235 | 194 | 99 | 1 |
| BASE | | 27013 | 3311 | 26491 | 3311 | 0 | 14 |
| DOX | 1 µM | 513 | 126 | -9 | 126 | 100 | 1 |

Fig. 9E

| IC50 = 1.138 µg/mL |
|---|
| (THEORETICAL IC50 CALCULATED ABSORBANCE VALUE = 11795) |
| CONCENTRATIONS USED FOR REGRESSION 3.000 AND 1.000 µg/mL |
| REGRESSION OUTPUT |
| CONSTANT                           18573 <br> STD ERR OF Y EST           2863 <br> R SQUARED                            1 <br> NO. OF OBSERVATIONS     16 <br> DEGREES OF FREEDOM    14 <br><br> X COEFFICENT(S)               -5957 <br> STD ERR OF COEF.              716 |

Fig. 9F

CELL LINE: LOX IMVI MELANOMA
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   1902   ±   639 )

| TREATMENT | | RAW ABSORBANCE VALUE | | MEAN MINUS BACK-GROUND | SD | % INHIBITION | |
|---|---|---|---|---|---|---|---|
| AGENT | DOSAGE (µg/mL) | MEAN | SD | | | MEAN | SD |
| CONTROL | - | 243895 | 44414 | 241994 | 44414 | 0 | 18 |
| DIS.COMP. | 0.003 | 258286 | 19215 | 256384 | 19215 | 0 | 8 |
| | 0.01 | 254659 | 36627 | 252757 | 36627 | 0 | 15 |
| | 0.03 | 254844 | 47365 | 252942 | 47365 | 0 | 20 |
| | 0.1 | 266290 | 15708 | 264388 | 15708 | 0 | 6 |
| | 0.3 | 260996 | 45040 | 259094 | 45040 | 0 | 19 |
| | 1 | 290330 | 53822 | 288429 | 53822 | 0 | 22 |
| | 3 | 209898 | 39408 | 207996 | 39408 | 14 | 16 |
| | 10 | 46118 | 11089 | 44216 | 11089 | 82 | 5 |
| BASE | | 242585 | 36793 | 240683 | 36793 | 1 | 15 |
| DOX | 1 µM | 2613 | 906 | 711 | 906 | 100 | 0 |

Fig. 10B

| IC50 = 6.718 µg/mL |
|---|
| (THEORETICAL IC50 CALCULATED ABSORBANCE VALUE = 120997) |
| CONCENTRATIONS USED FOR REGRESSION 10.000 AND 3.000 µg/mL |
| REGRESSION OUTPUT |
| CONSTANT                           278187<br>STD ERR OF Y EST              28948<br>R SQUARED                               1<br>NO. OF OBSERVATIONS         16<br>DEGREES OF FREEDOM        14<br><br>X COEFFICENT(S)                -23397<br>STD ERR OF COEF.              2068 |

Fig. 10C

CELL LINE: LOX IMVI MELANOMA
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   789   ±   398 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 285056 | 33838 | 213002 | 135019 | 0 | 63 |
| DC+B | 0.003 | 288418 | 15624 | 215524 | 134163 | 0 | 63 |
| | 0.01 | 268852 | 46465 | 200850 | 130503 | 6 | 61 |
| | 0.03 | 247485 | 26154 | 184824 | 116676 | 13 | 55 |
| | 0.1 | 257474 | 29499 | 192316 | 121767 | 10 | 57 |
| | 0.3 | 190485 | 32458 | 142075 | 92346 | 33 | 43 |
| | 1 | 34952 | 6888 | 25424 | 17195 | 88 | 8 |
| | 3 | 1591 | 700 | 404 | 945 | 100 | 0 |
| | 10 | 1029 | 259 | -17 | 524 | 100 | 0 |
| BASE | | 306550 | 29632 | 229123 | 144098 | 0 | 68 |
| DOX | 1 µM | 2221 | 293 | 877 | 1058 | 100 | 0 |

Fig. 10E

| IC50 = 0.513 µg/mL |
|---|
| (THEORETICAL IC50 CALCULATED ABSORBANCE VALUE = 106501) |
| CONCENTRATIONS USED FOR REGRESSION 1.000 AND 0.300 µg/mL |
| REGRESSION OUTPUT |
| CONSTANT 192068<br>STD ERR OF Y EST 66421<br>R SQUARED 0<br>NO. OF OBSERVATIONS 16<br>DEGREES OF FREEDOM 14<br><br>X COEFFICENT(S) -166643<br>STD ERR OF COEF. 47443 |

Fig. 10F

CELL LINE: SNB-75 CNS
CELLS PLATED: 5.0E+03 CELLS/WELL
TREATMENT DAY 1 POST PLATING, CONTINUOUS EXPOSURE

*DISCLOSED COMPOSITION*

( MEDIA + MTS [BACKGROUND]   =   672   ±   302 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 48412 | 19367 | 47739 | 19367 | 0 | 41 |
| DIS.COMP. | 0.003 | 48690 | 12158 | 48018 | 12158 | 0 | 25 |
| | 0.01 | 36743 | 8449 | 36071 | 8449 | 24 | 18 |
| | 0.03 | 43415 | 15428 | 42743 | 15428 | 10 | 32 |
| | 0.1 | 46415 | 12022 | 45743 | 12022 | 4 | 25 |
| | 0.3 | 46134 | 10910 | 45462 | 10910 | 5 | 23 |
| | 1 | 23478 | 12579 | 22806 | 12579 | 52 | 26 |
| | 3 | 7921 | 1545 | 7249 | 1545 | 85 | 3 |
| | 10 | 809 | 123 | 137 | 123 | 100 | 0 |
| BASE | | 58868 | 20011 | 58196 | 20011 | 0 | 42 |
| DOX | 1 µM | 1288 | 302 | 615 | 302 | 99 | 1 |

Fig. 11B

| IC50 = 0.895 µg/mL |
|---|
| (THEORETICAL IC50 CALCULATED ABSORBANCE VALUE = 23870) |
| CONCENTRATIONS USED FOR REGRESSION 1.000 AND 0.300 µg/mL |
| REGRESSION OUTPUT |
| CONSTANT 56348<br>STD ERR OF Y EST 12549<br>R SQUARED 1<br>NO. OF OBSERVATIONS 16<br>DEGREES OF FREEDOM 14<br><br>X COEFFICENT(S) -36287<br>STD ERR OF COEF. 8964 |

Fig. 11C

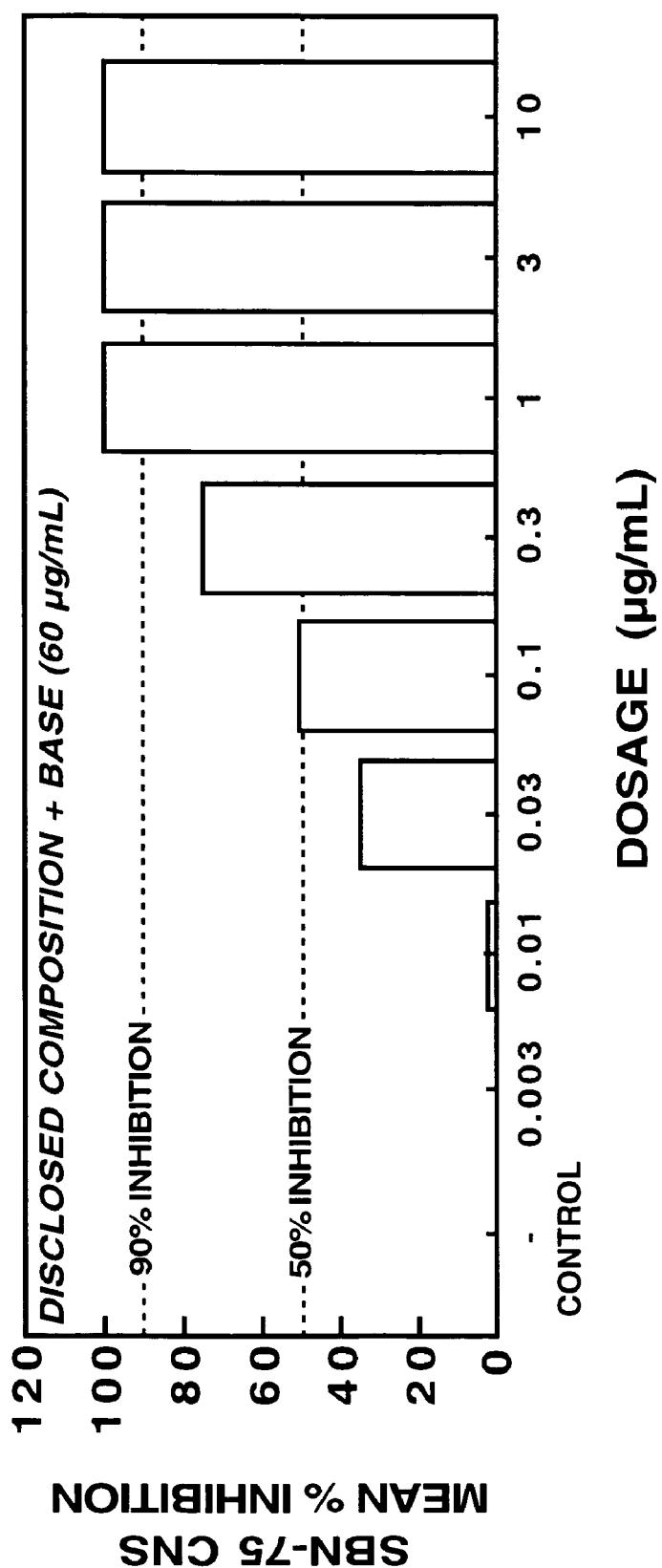

CELL LINE: SNB-75 CNS
CELLS PLATED: 5.0E+03 CELLS/WELL
TREATMENT DAY 1 POST PLATING, CONTINUOUS EXPOSURE

*DISCLOSED COMPOSITION + BASE (60 µg/mL)*

( MEDIA + MTS [BACKGROUND]   =   591   ±   131 )

| TREATMENT | | RAW ABSORBANCE VALUE | | MEAN MINUS BACK- GROUND | SD | % INHIBITION | |
|---|---|---|---|---|---|---|---|
| AGENT | DOSAGE (µg/mL) | MEAN | SD | | | MEAN | SD |
| CONTROL | - | 76631 | 13201 | 76040 | 13201 | 0 | 17 |
| DC+B | 0.003 | 84352 | 17247 | 83761 | 17247 | 0 | 23 |
| | 0.01 | 76032 | 9649 | 75441 | 9649 | 1 | 13 |
| | 0.03 | 43393 | 18208 | 42802 | 18208 | 44 | 24 |
| | 0.1 | 38209 | 12752 | 37618 | 12752 | 51 | 17 |
| | 0.3 | 19327 | 30859 | 18736 | 30859 | 75 | 41 |
| | 1 | 793 | 204 | 202 | 204 | 100 | 0 |
| | 3 | 257 | 73 | -334 | 73 | 100 | 0 |
| | 10 | 452 | 119 | -139 | 119 | 100 | 0 |
| BASE | | 59124 | 15254 | 58533 | 15254 | 23 | 20 |
| DOX | 1 µM | 1006 | 169 | 415 | 169 | 99 | 0 |

Fig. 11E

| IC50 = 0.095 µg/mL |  |
|---|---|
| (THEORETICAL IC50 CALCULATED ABSORBANCE VALUE = 38020) | |
| CONCENTRATIONS USED FOR REGRESSION 0.100 AND 0.030 µg/mL | |
| REGRESSION OUTPUT | |
| CONSTANT | 45023 |
| STD ERR OF Y EST | 15719 |
| R SQUARED | 0 |
| NO. OF OBSERVATIONS | 16 |
| DEGREES OF FREEDOM | 14 |
| X COEFFICENT(S) | -74055 |
| STD ERR OF COEF. | 112276 |

Fig. 11F

TOXICITY VALUES (Tritiated Thymidine Incorporation)

| CONC. (µg/mL) | 0 | 0.32 | 1 | 3.2 | 10 | 32 | 100 |
|---|---|---|---|---|---|---|---|
| SAMPLE 1 | 187251 | 238620 | 247533 | 147690 | 4875 | 7905 | 100 |
| SAMPLE 2 | 215975 | 249276 | 208674 | 168000 | 6001 | 4214 | 100 |
| SAMPLE 3 | 251706 | 243978 | 228104 | 157458 | 5483 | 6214 | 44 |
| MEAN | 218311 | 243958 | 228104 | 157716 | 5453 | 6111 | 67 |
| STD. DEV. | 14.8 | 2.4 | 8.9 | 4.7 | 0.3 | 0.8 | 70 |
| MEAN % INH. | 0 | 0 | 0 | 27.8 | 97.5 | 97.2 | 100 |

Fig. 12B

| IC50 (µg/mL) = 5.87 |
|---|

Fig. 12C

TOXICITY VALUES (Tritiated Thymidine Incorporation)

| CONC. (µg/mL) | 1000 | 320 | 100 | 32 | 10 | 3.2 | 1 | 0.32 | 0.1 | 0.032 | 0.01 | 0.0032 | 0 |
|---|---|---|---|---|---|---|---|---|---|---|---|---|---|
| SAMPLE 1 | 44 | 52 | 36 | 40 | 540 | 336208 | 468933 | 470659 | 484041 | 482276 | 478360 | 520558 | 522374 |
| SAMPLE 2 | 264 | 480 | 1281 | 184 | 1974 | 361141 | 451751 | 479896 | 490045 | 485336 | 476935 | 521223 | 509600 |
| MEAN | 154 | 265 | 659 | 12 | 1257 | 348675 | 460342 | 475278 | 487043 | 483806 | 477148 | 520891 | 515987 |
| MEAN % INH. | 100 | 99.9 | 99.9 | 99.9 | 99.9 | 32.4 | 10.8 | 7.9 | 5.6 | 6.2 | 7.5 | 0 | 0 |

| CELL LINE | IC50 (µg/mL) DISCLOSED COMPOSITION ONLY | IC50 (µg/mL) DISCLOSED COMP. + BASE (60 µg/mL) |
|---|---|---|
| NCI-H23 LUNG | >10 | 1.718 |
| NCI-H460 LUNG | 1.183 | 0.131 |
| MCF7 MAMMARY | 2.213 | 0.972 |
| ZR-75-1 MAMMARY | >10 | 2.031 |
| PC-3 PROSTATE | >10 | 1.869 |
| DLD-1 COLON | 1.430 | 0.196 |
| OVCAR-3 OVARIAN | 3.662 | 0.299 |
| CAKI-1 RENAL | 1.440 | 1.138 |
| LOX IMVI MELANOMA | 6.718 | 0.513 |
| SNB-75 CNS | 0.895 | 0.095 |
| CEM-SS LEUKEMIC (#1) | 5.87 | - |
| CEM-SS LEUKEMIC (#2) | 4.975 | - |

Fig. 14

ELEMENTAL IRON DERIVED FROM IRON DEXTRAN IN MONKEY PLASMA

| CONTROL NUMBER | ID/DAY | TIME | ANALYTE/ LIMIT | VALUES | UNITS |
|---|---|---|---|---|---|
| 413223 | AD51,DAY1 | PRE | IRON | 0.0 | MG/ML |
| 413223 | AD51,DAY1 | PRE | RL | 0.1 | |
| 413224 | AN3B,DAY1 | PRE | IRON | 0.0 | MG/ML |
| 413224 | AN3B,DAY1 | PRE | RL | 0.1 | |
| 413225 | AD51,DAY1 | POST | IRON | 6.8 | MG/ML |
| 413225 | AD51,DAY1 | POST | RL | 0.1 | |
| 413226 | AH3B,DAY1 | POST | IRON | 11.2 | MG/ML |
| 413226 | AH3B,DAY1 | POST | RL | 0.1 | |
| 413227 | AD51,DAY1 | 10 MIN | IRON | 7.1 | MG/ML |
| 413227 | AD51,DAY1 | 10 MIN | RL | 0.1 | |
| 413228 | AH3B,DAY1 | 10 MIN | IRON | 11.8 | MG/ML |
| 413228 | AH3B,DAY1 | 10 MIN | RL | 0.1 | |
| 413229 | AD51,DAY2 | 24 HR | IRON | 4.7 | MG/ML |
| 413229 | AD51,DAY2 | 24 HR | RL | 0.1 | |
| 413230 | AH3B,DAY2 | 24 HR | IRON | 7.0 | MG/ML |
| 413230 | AH3B,DAY2 | 24 HR | RL | 0.1 | |
| 413231 | AD51,DAY3 | 48 HR | IRON | 3.2 | MG/ML |
| 413231 | AD51,DAY3 | 48 HR | RL | 0.1 | |
| 413232 | AH3B,DAY3 | 48 HR | IRON | 6.4 | MG/ML |
| 413232 | AH3B,DAY3 | 48 HR | RL | 0.1 | |
| 413233 | AD51,DAY4 | 72 HR | IRON | 1.6 | MG/ML |
| 413233 | AD51,DAY4 | 72 HR | RL | 0.1 | |
| 413234 | AH3B,DAY4 | 72 HR | IRON | 5.5 | MG/ML |
| 413234 | AH3B,DAY4 | 72 HR | RL | 0.1 | |

Fig. 15A

ELEMENTAL IRON DERIVED FROM IRON DEXTRAN IN MONKEY PLASMA (continued)

| CONTROL NUMBER | ID/DAY | TIME | ANALYTE/ LIMIT | VALUES | UNITS |
|---|---|---|---|---|---|
| 413235 | AD51,DAY5 | 96 HR | IRON | 0.7 | MG/ML |
| 413235 | AD51,DAY5 | 96 HR | RL | 0.1 | |
| 413236 | AH3B,DAY5 | 96 HR | IRON | 3.9 | MG/ML |
| 413236 | AH3B,DAY5 | 96 HR | RL | 0.1 | |
| 413237 | AD51,DAY6 | 120 HR | IRON | 0.1 | MG/ML |
| 413237 | AD51,DAY6 | 120 HR | RL | 0.1 | |
| 413238 | AH3B,DAY6 | 120 HR | IRON | 2.6 | MG/ML |
| 413238 | AH3B,DAY6 | 120 HR | RL | 0.1 | |
| 413239 | AD51,DAY7 | N/A | IRON | 0.0 | MG/ML |
| 413239 | AD51,DAY7 | N/A | RL | 0.1 | |
| 413240 | AH3B,DAY7 | N/A | IRON | 1.4 | MG/ML |
| 413240 | AH3B,DAY7 | N/A | RL | 0.1 | |
| 413241 | AD51,DAY8 | N/A | IRON | 0.0 | MG/ML |
| 413241 | AD51,DAY8 | N/A | RL | 0.1 | |
| 413242 | AH3B,DAY8 | N/A | IRON | 0.6 | MG/ML |
| 413242 | AH3B,DAY8 | N/A | RL | 0.1 | |
| 413243 | AH3B,DAY9 | N/A | IRON | 0.0 | MG/ML |
| 413243 | AH3B,DAY9 | N/A | RL | 0.1 | |
| 413244 | AD51,DAY9 | N/A | IRON | 0.0 | MG/ML |
| 413244 | AD51,DAY9 | N/A | RL | 0.1 | |
| 413245 | AH3B,DAY10 | N/A | IRON | 0.0 | MG/ML |
| 413245 | AH3B,DAY10 | N/A | RL | 0.1 | |
| 413246 | AD51,DAY10 | N/A | IRON | 0.0 | MG/ML |
| 413246 | AD51,DAY10 | N/A | RL | 0.1 | |

Fig. 15B

ELEMENTAL IRON DERIVED FROM IRON DEXTRAN IN MONKEY PLASMA (concluded)

| CONTROL NUMBER | ID/DAY | TIME | ANALYTE/ LIMIT | VALUES | UNITS |
|---|---|---|---|---|---|
| 413247 | AD51,DAY15 | N/A | IRON | 0.0 | MG/ML |
| 413247 | AD51,DAY15 | N/A | RL | 0.1 | |
| 413248 | AH38,DAY38 | N/A | IRON | 0.0 | MG/ML |
| 413248 | AH3B,DAY38 | N/A | RL | 0.1 | |
| 413249 | AD51,DAY22 | N/A | IRON | 0.0 | MG/ML |
| 413249 | AD51,DAY22 | N/A | RL | 0.1 | |
| 413250 | AH3B,DAY22 | N/A | IRON | 0.0 | MG/ML |
| 413250 | AH3B,DAY22 | N/A | RL | 0.1 | |

KEY

AD51 = Monkey administered 400mg equivalent of elemental iron per kg of body weight AH3B = Monkey administered 500mg equivalent of elemental iron per kg of body weight RL = Reporting Limit TIME = When samples were taken after intravenous infusion PRE = pretreatment levels POST = directly after infusion 10 MIN = 10 minutes after infusion

Fig. 15C

SINGLE DOSE ADMINISTRATION
ELEMENTAL IRON DERIVED FROM IRON DEXTRAN IN MONKEY PLASMA

| GROUP NUMBER | NUMBER OF ANIMALS | TREATMENT ADMINISTRATION | | | | OBSERVATION PERIOD |
| --- | --- | --- | --- | --- | --- | --- |
| | | SUBSTANCE | DOSE LEVEL | ROUTE | DOSING REGIMEN | |
| 1 | 1 | IRON DEXTRAN COMPLEX | 400 MG ELEMENTAL IRON/KG | IV | DAY 1 3 HOUR INFUSION 1 MIN/ML | 10 DAYS |
| 2 | 1 | | 500 MG ELEMENTAL IRON/KG | | | |

Fig. 16

ANTI TUMOR COMPOSITIONS AND METHODS OF USE

TECHNICAL FIELD

The present disclosure relates to pharmaceutical compositions and methods of use for treating cancer in mammals.

BACKGROUND

All patents, scientific articles, and other documents mentioned herein are incorporated by reference as if reproduced in full below. Cancer is the rapid and uncontrolled proliferation of new cells within a body, and is a leading cause of death in animals, including humans. This proliferation far exceeds the normal level of apoptosis, the physiological process essential to normal development and homeostasis of multicellular organisms. (Stellar, Science 267:1445-1449 (1995)).

Chemotherapy, often used in conjunction with radiation treatments and surgery, is a standard cancer treatment used today. Chemotherapy is generally understood to mean medications or drugs that destroy cancer cells. Presently, there are over one hundred drugs used in various combinations to treat cancer. (The American Cancer Society, *Consumers Guide to Cancer Drugs*, Jones and Bartlett Publishers, (2000)). "All these drugs have one characteristic in common. They work because they're poisons." (Moss, *Questioning Chemotherapy*, Equinox Press, pg. 77, (2000)). Chemotherapeutic agents are highly toxic and typically have narrow therapeutic indices. These agents exhibit little specificity for malignant cells, and they cannot discriminate effectively between normal and malignant cells. Consequently, all cells and tissues, and especially rapidly proliferating cells, such as the bone marrow cells, the spermatogonia, and the gastrointestinal crypt epithelium cells, are very vulnerable. (Baquiran, *Cancer Chemotherapy Handbook*, Lippincott, pg. 85 (2001)). Moreover, the side effects of chemotherapy can be horrific, as is well known to those of skill in the art and to those unfortunate enough to have the art practiced upon them. (The American Cancer Society, *Consumers Guide to Cancer Drugs*, Jones and Bartlett Publishers, (2000)). See also, (Baquiran, *Cancer Chemotherapv Handbook, Lippincott*, p 85 (2001)); (Chu & Devita, *Physicians' Cancer Chemotherapy Drug Manual*, 2003, Jones and Bartlett Publishers, (2003)); (Lance Armstrong, *It's Not About the Bike*, Berkley Publishing, (2000)), (King, King and Pearlroth, *Cancer Combat*, Bantam Books, (1998)); (Rich, *The Red Devil*, Three Rivers Press, (1999)); and (Marchione, *Hopes in cancer drug dashed*, Milwaukee Journal Sentinel, May 22, (2002)). Current cancer treatments including chemotherapy do not generally work well with solid tumors. (Moss, *Questioning Chemotherapy*, Updated Edition, Equinox Press, 2000:18) and (Masters and Koberle, in *Curing Metastatic Cancer: Lessons from Testicular Germ-Cell Tumours*, Nature Reviews, 3(7) (July 2003)).

Resistance can develop to chemotherapeutic agents, causing the agents to work for some types of cancer, but not for others, or not work at all. Resistance has been demonstrated to every single chemotherapeutic agent ever developed. This resistance may be innate, acquired or emergent resistance. (Chu & Devita; *Physicians' Cancer Chemotherapy Drug Manual*, 2003, Jones and Bartlett Pub. (2003)). In addition, it has been commonly assumed that combining chemotherapeutic agents will result in regimens with superior response rates. However, a study demonstrated that chemotherapy agents, used either in sequence or in combination for metastatic breast cancer, provided equivalent results with regard to survival and quality of life was measured. (Sledge, et al., *Phase III, Trial of Doxorubicin, paclitaxel, and the combination of doxorubicin and paclitaxel as front-line chemotherapy for metastatic breast cancer: an intergroup trial*, J. of Clin. Oncology, 21 (4):588-592 (February, 2003)).

Additionally, a study utilizing four of the newer chemotherapy regimens and drugs produced a two-year survival rate of 11% and substantial toxicity. The response and survival rate did not differ significantly amongst the four groups treated with the different regimens for advanced non-small-cell lung cancer. (Schiller, et al., *Comparison of Four Chemotherapy Regimens for Advanced Non-Small-Cell Lung Cancer*, The N. Eng. J. of Med., 346(2):92-98 (January, 2002)).

Cancer cells are well known to have a higher glucose uptake and metabolism, and the resulting enhanced glycolysis can serve as an indication of a malignant transformation. (Mehvar, *Dextrans for targeted and sustained delivery of therapeutic and imaging agents*, J. of Controlled Release, 69:1-25 (2000)); (Essner, et al., *Advances in FDG PET Probes in Surgical Oncology*, Cancer Jour. 8:100-108 (2002)). Cancer cells utilize and metabolize glucose at high rates, (even in the presence of high oxygen concentrations) forming mostly lactate. (Warburg, O., *On The Origin of Cancer Cells*, Science 123 (3191): 309-314 (February, 1956)). Lactate, therefore, is detected in cancer cells at much higher levels than in the corresponding normal tissues. (Rivenzon-Segal, et. al., *Glycolysis as a metabolic marker in orthotoPic breast cancer, monitored by in vivo 13C MRS*, Amer. J. Phys. Endocrinology Metabolism, 283: E623-E630 (2002); See also, (Lee and Pedersen, *Glucose Metabolism in Cancer*, J. of Biol. Chem. 278 (42):41047-41058 (October, 2003)); (Gatenby and Gawlinski, *The glycolysis phenotype in carcinogenesis and tumor invasion: insights through mathematical models*, Cancer Res., 63(14):3847-54 (July, 2003)); (Degani, *The American Society of Clinical Oncology*, Intn'l J. of Cancer, 107:177-182 (November, 2003)); (Warburg, O. *The Prime Cause and Prevention of Cancer*, Konrad Triltsch, p 6. (1969)). Glucose typically enters most cells by facilitated diffusion through one of a family of glucose transporters. (Katzung, *Basic & Clinical Pharmacology*, McGraw Hill Co. Inc., pg. 715 (2001)). Glucose forms that are incompatible with these transporters can be taken in by phagocytosis, also known as endocytosis, either by a cell of the phagocytic system or a cell associated with a tissue. The phagocytic system, also known as the reticuloendothelial system ("RES"), or the mononuclear phagocyte system ("MPS"), is a diffuse system, which includes the fixed macrophages of tissues, liver, spleen, lymph nodes and bone marrow, along with the fibroblastic reticular cells of hemotopoietic tissues.

Glucose initiates, promotes, drives and amplifies the growth and metastasis of tumor cells. Anaerobic glycolosis favored by tumor cells, is a very inefficient and primitive process to produce ATP, requiring prodigious amounts of glucose. Thus, the scientific community is currently working on ways to deprive tumor cells of glucose. (Van Dang et al, The Proc. of the Nat'l Acad. of Sci. 95:1511-1516 (1998)). (Pedersen, *Inhibiting glycolysis and oxidative phosphorylation, 3-BrPA abolishes cell ATP production*, Reuters News, (Jul. 18, 2002)). An in vivo murine study on xenograft models of human osteosarcoma and non-small cell lung cancer found that the glycolytic inhibitor 2-deoxy-D-glucose in combination with adriamycin or paxlitaxel, resulted in significant slower tumor growth. (Maschek, et al., *2-deoxy-D-glucose increases the efficacy of adriamycin and paclitaxel in human osteosarcoma and non-small cell lung cancers in vivo*, Cancer Res., 64(1):31-34 (2004)). In addition, positive clinical results have been found with the anti-cachexia drug, hydrazine sulfate, which inhibits neoglucogenesis. (Moss, *Cancer Therapy*, Equinox Press, p 316 (1992)). Many dietary modifications directed at depriving cancer cells of glucose have also been studied. (Quillin, *Beating Cancer with Nutrition*, Nutrition Times Press, p 225 (1998)); (Quillin, *Cancer's Sweet Tooth*, Nutrition Science News, (April 2000)); and (Hauser & Hauser, *Cancer-Treating Cancer with Insulin Potentiation Therapy*, Beulah Land Press, (2001)).

Copper (Cu), is an essential trace element, and necessary for life in organisms ranging from bacteria to mammals. Copper promotes and is an essential co-factor for angiogenesis, a requirement for the growth of cancer, especially solid tumors. (Brewer, *Handbook of Copper Pharmacology and Toxicology*, Humana Press, Chap. 27, (2002)); (Brem, *Angiogenesis and Cancer Control: From Concept to Therapeutic Trial*, Cancer Control Jour., 6 (5):436-458 (1999). Since angiogenesis is generally not required in adults, the inhibition of angiogenesis through copper removal, copper reduction therapy, or copper withholding, has been explored as a possible mechanism for inhibiting further tumor growth. (Brewer, supra); See, also U.S. Pat. No. 6,703,050 of Brewer et al. Tumors of many types have a great need for copper and sequester copper, because copper is an essential cofactor for angiogenesis and proliferation. (Brewer. *Copper Control as an Antiangiogenic Anticancer Therapy: Lessons from Treating Wilson's Disease*, Exp. Bio. and Med., 226(7):665-673 (2001)). Because of this avidity for copper, and effects of copper promoting tumor initiation, growth and metastasis, the scientific community continues to develop methods and pharmaceuticals of withholding copper from tumor cells. (Brem, supra); (Brewer, supra); (Brewer, et al., *Treatment of Metastatic Cancer with Tetrathiomolybdate, an Anticopper, Antiangiogenesis Agent: Phase I Study*, Clin. Cancer Res., 6:1-10 (2000)); (Redman, *Phase II Trial of Tetrathiomolybdate in Patients with Advanced Kidney Cancer*, Clin. Cancer Res., 9:1666-1672 (2003)); (Pan, et al., *Copper Deficiency Induced by Tetrathiomolybdate Suppresses Tumor Growth and Angiogenesis*, Cancer Res., 62:4854-4859 (2002)); (Teknos, et al., *Inhibition of the Growth of Squamous Cell Carcinoma by Tetrathiomolybdate-Induced Copper Suppression in a Murine Model*, Arch. of Otolaryngology: Head And Neck Surgery, Oncolink Cancer News, Reuters, 129:781-785 (2003)); (Yoshiji, et al., *The Copper Chelating Agent, trientine, suppresses tumor development and angiogenesis in the murine heptatocellular carcinoma cells*, Int'l J. of Cancer, 94:768-773 (December, 2001); (Yoshiji, et al., *The cooper chelating agent, Trientine attenuates liver enzymes-altered preneoplastic lesions in rats by angiogenesis suppression*, Oncology Rep., 10(5):1369-73 (2003)); (Brem, et al., *Penicillamine and Reduction of Copper for Angiosuppressive Therapy of Adults with Newly Diagnosed Glioblastoma*, H. Lee Moffitt Cancer Center & Research Inst., (1999)); (Sagripanti and Kraemer, *Site-specific Oxidative DNA Damage at Polyguanosines Produced by Copper Plus Hydrogen Peroxide*, J. of Biol. Chem., 264(3):1729-1734 (1989)).

Copper may also promote cancer growth in ways such as damaging DNA. (Sagripanti, supra (1999)). The destructive activity of copper in a cell includes binding to DNA, cleaving DNA, in the presence of reducants and hydrogen peroxides, non-specific disruption of cellular function, and the generation of free hydroxyl radicals through Haber-Weiss reactions. (Theophanides, et al., *Copper and Carcinogenesis*, Critical Reviews In Oncology/Hematology, 42:57-64 (2002)). Copper also plays a role in the formation of reactive oxygen species ("ROS"). (Sagripanti, *DNA Damage Mediated by Metal Ions with Special Reference to Copper and Iron*, Met. Ions Biol. Syst. 36:179-209(1999)).

The use of copper has also been disclosed for the treatment of cancer in a number of U.S. patents as well: U.S. Pat. No. 4,952,607 discloses copper complexes exhibiting super oxide dismutase-like activity in mammalian cells; U.S. Pat. No. 5,124,351 discloses the use of copper chelate of nitrilotriacetic acid or a copper chelate of bis-thiosemicarbazone; U.S. Pat. No. 5,632,982 discloses the use of copper chelates in conjunction with a surface membrane protein receptor internalizing agent, particularly TNF for use against target cells; and U.S. Pat. No. 6,706,759 discloses the use of dithiocarbamate derivatives and copper.

It is also known that a quantitative difference exists between cancer cells and normal cells with respect to iron requirements, because enhanced acquisition of iron initiates, promotes, and amplifies the growth, and metastasis, of tumor cells. Iron is an essential transition metal for a large number of biological processes ranging from oxygen transport through DNA synthesis and electron transport. Iron is also involved in carcinogenic mechanisms, which include the generation of DNA damaging reactive oxygen species, and the suppression of host cell defenses. (Desoize, B., Editor, *Cancer in Metals and Metal Compounds: Part I—Carcinogenesis*, Critical Reviews In Oncology/Hematology, 42:1-3 (2002)); (Galaris, et al., *The Role of Oxidative Stress in Mechanisms of Metal-induced Carcinogenesis*, Critical Reviews In Oncology/Hematology, 42:93-103 (2002)); (Weinberg, *Cancer and Iron: a Dangerous Mix*, Iron Disorders Insight, 2(2):11 (1999)); (Weinberg, *The Development of Awareness of the Carcinogenic Hazard of Inhaled Iron*, Oncology Res. 11:109-113 (1999)); (Weinberg, *Iron Therapy and Cancer*, Kidney Int'l, 55(60): S131-134 (1999)); (Weinberg, *The Role of Iron in Cancer*, Euro. J. Cancer Prevention, 5:19-36, (1996)); (Weinberg, *Iron in Neoplastic Disease*, Nutrition Cancer, 4(3):223-33 (1993)); (Stevens, et al., *Body Iron Stores and the Risk of Cancer*, N. Eng. J. of Med., 319(16):1047-1052 (1988)).

A number of pharmaceuticals have been developed to control and restrict the supply of iron to tumor cells using different approaches, including intracellular iron-chelating agents for withdrawal of the metal, use of gallium salts to interfere with iron uptake, and utilization of monoclonal antibodies to transferrin receptors on tumors to block the uptake of iron. For example, U.S. Pat. No. 6,589,96, incorporated herein in its entirety, teaches the use of iron chelators as chemotherapeutic agents against cancer to deprive cancer cells of iron. See also, (Kwok, et al., *The Iron Metabolism of Neoplastic Cells: alterations that facilitate proliferation?*, Crit. Rev. In Oncology/Hematology, 42:65-78 (2002), discloses tumor cells express high levels of the transferrin receptor 1 (TFR1) and internalize iron (Fe) from transferrin (TF) at a tremendous rate.); (Desoize, B. Editor, *Cancer and Metals and Metal Compounds, Part II—Cancer Treatment*, Crit. Rev. In Oncology/Hematology, 42:213-215 (2002)); (Collery, et al., *Gallium in Cancer Treatment*, Crit. Rev. In Oncology/Hematology, 42:283-296 (2002)); (Weinberg, *Development of Clinical Methods of Iron Deprivation for Suppression of Neoplastic and Infectious Diseases*, Cancer Investigation, 17(7): 507-513 (1999)); (Weinberg, *Human Lactoferrin: a Novel Therapeutic with Board Spectrum Potential*, Pharmacy & Pharmacology, 53 (October 2001)); (Richardson, *Iron Chelators as therapeutic agents for the Treatment of Cancer*, Crit. Rev. In Oncology/Hematology, 42:267-281 (2002)).

When an iron dextran complex is administered to the blood system, the cellular toxicity of iron is blocked by the dextran sheath or shell in doses above or below the rate of clearance of the RES system. (Lawrence, *Development and Comparison* of Iron Dextran Products, J. of Pharm. Sci. & Tech., 52(5): 190-197(1998)); (Cox, Structure of an iron-dextran complex, J. of Pharma & Pharmac, 24:513-517 (1972)); (Henderson & Hillman, Characteristics of Iron Dextran Utilization in Man, Blood, 34(3):357-375 (1969)); U.S. Pat. No. 5,624,668). Iron dextran can remain in the plasma and traffic throughout the body for weeks inertly, while being removed from the plasma by the phagocytic system and cancer cells.

Copper and iron are essential micronutrients for all organisms because of their function as co-factors in enzymes that catalyze redox reactions in fundamental metabolic processes. (Massaro, editor, Handbook of Copper Pharmacology and Toxicity, Humana Press, 2002, Chapter 30, p 481). Studies have shown synergistic interactions between iron and copper, which result in a significant increase in utilization of iron as compared to the utilization found with iron only compounds. (Massaro, Chap. 30, supra). To bind iron to the plasma protein transferrin, oxidation is required from $Fe^{2+}$ to $Fe^{3+}$. The oxidation may be mediated by multicopper ferroxidases, hephaestin or ceruloplasmin. Hephaestin may act together with Ferroportin1 at the surface of enterocytes to oxidize $Fe^{2+}$ to $Fe^{3+}$ prior to export into blood plasma for loading onto transferrin. An additional important role of ceruloplasmin is the mobilization of iron from tissues such as the liver where ceruloplasmin is synthesized. The ceruloplasmin can contain six copper atoms, is secreted from the liver, and can carry at least 95% of total serum copper for delivery to tissues. In addition, ceruloplasmin, via its ferroxidase activity, mediates iron release from the liver, also for delivery to tissues. Thus, both copper and iron support the hematopoietic system, especially red blood cell formation. Each is essential for the formation of red blood cells.

The American Cancer Society report, Cancer Facts and Figures 2003, discloses that "cancer is a group of diseases characterized by uncontrolled growth and spread of abnormal cells. . . . About 1,334,100 new cancer cases are expected to be diagnosed in the United States in 2003, with 556,500 cancer deaths expected in 2003." The present invention includes, but is not limited to, the treatment of these cancers disclosed in Cancer Facts and Figures 2003, page 4, supra, such as, Oral Cavity and Pharynx, Digestive System, Respiratory System, Bones and Joints, Soft Tissue, Skin, Breast, Genital System, Urinary System, Eye and Orbit, Brain and Other Nervous System, Endocrine System, Lymphoma, Multiple Myeloma, Leukemia, and Other Unspecified Primary Sites. Treatment with the present invention also includes basal and squamous cell skin cancers and in situ carcinomas, Hyper Proliferative Disorders, myelodysplasia disorders and Plasma Cell Dyscrasias, which is characterized by an increase in plasma cells in the bone marrow, or uncommonly, other tissue. A description of these clinical abnormalities is disclosed by Markman, M. D. in Basic Cancer Medicine, W. B. Saunders Co., p. 103, (1997).

It would be advantageous to develop an effective chemotherapeutic agent which employs biocompatible materials, materials which feed every cell in the body, to effectuate cell death, at minimum, prevent cancer cell replication, and avoid classic and numerous deadly chemotherapeutic side effects. Such a therapeutic agent would avoid the issues of tissue resistance and lack of specificity that are caused by many pharmaceuticals, thereby destroying or disabling many previously unmanageable cancers without debilitating or killing the patient.

SUMMARY OF THE INVENTION

This disclosure relates to a Composition having anti-cancer properties and methods of use in mammals. A chemical Composition for use as a pharmaceutical for treating cancer of a biologically acceptable copper compound and may include other components such as iron, which is transported to afflicted cells in a pharmaceutical acceptable carrier. For example, the compound may be formed of a core of at least biologically acceptable copper compound which may be encapsulated with a sheath that surrounds or coats the copper compound core and prevents immediate chemical interaction of the core with the surrounding environment. The Composition is combined with a pharmaceutically acceptable carrier for administration to patients and may be used alone or in conjunction with conventional cancer treatments.

Also disclosed is a method for treating cancers by administering the Composition having a biologically acceptable copper compound core, with a sheath encapsulating the copper compound core, and a pharmaceutical carrier to the patient. The patient is monitored regularly to determine the level and/or presence of the cancer. The Composition may be re-administered at intervals determined to be medically necessary by the physician, based on the results of the monitoring.

Without limitation, these and other objects, features, and advantages of the present invention, will become apparent to those with skill in the art after review of the following detailed description of the disclosed embodiments and the appended drawings and claims.

BRIEF DESCRIPTION OF THE DRAWINGS

FIG. 2B is a chart of NCI-H23 lung cells dose response with control, the Composition alone, Base Compound alone and doxorubicin alone.

FIG. 2C is a chart of NCI-H23 lung cells with the Composition alone, with the $IC_{50}$ value.

FIG. 2E is a chart of NCI-H23 lung cells with control, the Composition plus Base Compound, Base Compound alone and doxorubicin alone.

FIG. 2F is a chart of NCI-H23 lung cells with the Composition plus Base Compound, with the $IC_{50}$ value.

FIG. 3B is a chart of NCI-H460 lung cells with control, the Composition alone, Base Compound alone, and doxorubicin alone.

FIG. 3C is a chart of NCI-H460 lung cells with the Composition along, with the $IC_{50}$ value.

FIG. 3E is a chart of NCI-H460 lung cells dose response with control, the Composition plus Base Compound, Base Compound alone and doxorubicin alone.

FIG. 3F is a chart of NCI-H460 lung cells with the Composition plus Base Compound, with the $IC_{50}$ value.

FIG. 4B is a chart of MCF7 mammary cells dose response with control, the Composition alone, Base Compound alone and doxorubicin alone.

FIG. 4C is a chart of MCF7 mammary cells with the Composition alone, with the $IC_{50}$ value.

FIG. 4E is a chart of MCF7 mammary cells with control, the Composition plus Base Compound, Base Compound alone and doxorubicin alone.

FIG. 4F is a chart of MCF7 mammary cells with the Composition plus Base Compound, with the $IC_{50}$ value.

FIG. 5B is a chart of ZR-75-1 mammary cells dose response with control, the Composition alone, Base Compound alone and doxorubicin alone.

FIG. 5C is a chart of ZR-75-1 mammary cells with the Composition alone, with the $IC_{50}$ value.

FIG. 5E is a chart of ZR-75-1 mammary cells alone with control, the Composition plus Base Compound, Base Compound alone and doxorubicin alone.

FIG. 5F is a chart of ZR-75-1 mammary cells with the Composition plus Base Compound, with the $IC_{50}$ value.

FIG. 6B is a chart of PC-3 prostate cells dose response with control, the Composition alone, Base Compound alone and doxorubicin alone.

FIG. 6C is a chart of PC-3 prostate cells with the Composition alone, with the $IC_{50}$ value.

FIG. 6E is a chart of PC-3 prostate cells with control, the Composition plus Base Compound, Base Compound alone and doxorubicin alone.

FIG. 6F is a chart of PC-3 prostate cells with the Composition plus Base Compound, with the $IC_{50}$ value.

FIG. 7B is a chart of DLD-1 colon cells dose response with control, the Composition alone, Base Compound alone and doxorubicin alone.

FIG. 7C is a chart of DLD-1 colon cells with the Composition alone, with the $IC_{50}$ value.

FIG. 7E is a chart of DLD-1 colon cells with control, the Composition plus Base Compound, Base Compound alone and doxorubicin alone.

FIG. 7F is a chart of DLD-1 colon cells with the Composition plus Base Compound, with the $IC_{50}$ value.

FIG. 8B is a chart of OVCAR-3 ovarian cells dose response with control, the Composition alone, Base Compound alone and doxorubicin alone.

FIG. 8C is a chart of OVCAR-3 ovarian cells with the Composition alone, with the $IC_{50}$ value.

FIG. 8E is a chart of OVCAR-3 ovarian cells with control, the Composition plus Base Compound, Base Compound alone and doxorubicin alone.

FIG. 8F is a chart of OVCAR-3 ovarian cells with the Composition plus Base Compound, with the $IC_{50}$ value.

FIG. 9B is a chart of CAKI-1 renal cells dose response with control, the Composition alone, Base Compound alone and doxorubicin alone.

FIG. 9C is a chart of CAKI-1 renal cells with the Composition alone, with the $IC_{50}$ value.

FIG. 9E is a chart of CAKI-1 renal cells with control, the Composition plus Base Compound, Base Compound alone and doxorubicin alone.

FIG. 9F is a chart of CAKI-1 renal cells with the Composition plus Base Compound, with the $IC_{50}$ value.

FIG. 10B is a chart of LOX IMVI melanoma cells dose response with control, the Composition alone, Base Compound alone and doxorubicin alone.

FIG. 10C is a chart of LOX IMVI melanoma cells with the Composition alone, with the $IC_{50}$ value.

FIG. 10E is a chart of LOX IMVI melanoma cells with control, the Composition plus Base Compound, Base Compound alone and doxorubicin alone.

FIG. 10F is a chart of LOX IMVI melanoma cells with the Composition plus Base Compound, with the $IC_{50}$ value.

FIG. 11B is a chart of SBN-75 CSN cells dose response with control, the Composition alone, Base Compound alone and doxorubicin alone.

FIG. 11C is a chart of SBN-75 CNS cells with the Composition alone, with the $IC_{50}$ value.

FIG. 11D is a graph of the concentration of the Composition plus Base Compound plotted against SBN-75 CNS cells mean % inhibition.

FIG. 11E is a chart of SBN-75 CNS cells with control, the Composition plus Base Compound, Base Compound alone and doxorubicin alone.

FIG. 11F is a chart of SBN-75 CNS cells with the Composition plus Base Compound, with the $IC_{50}$ value.

FIG. 12B is a chart of the assayed toxicity values of the CEM-SS Leukemic cells data.

FIG. 12C provides the $IC_{50}$ of the CEM-SS Leukemic cells data.

FIG. 13B is a chart of the assayed toxicity values of the CEM-SS Leukemic cell data.

FIG. 13C provides the $IC_{50}$ of the CEM-SS Leukemic cell data.

FIG. 14 is a table of the cell lines used and the results of this disclosure.

FIGS. 15A, B, and C are portions of a table on the concentration of the equivalent of elemental iron, which was derived from iron dextran, found in the monkey plasma over time.

FIG. 16 is a table of the single dose administrations of elemental iron, which was derived from iron dextran, found in the monkey plasma over time.

DETAILED DESCRIPTION

Figure 1:
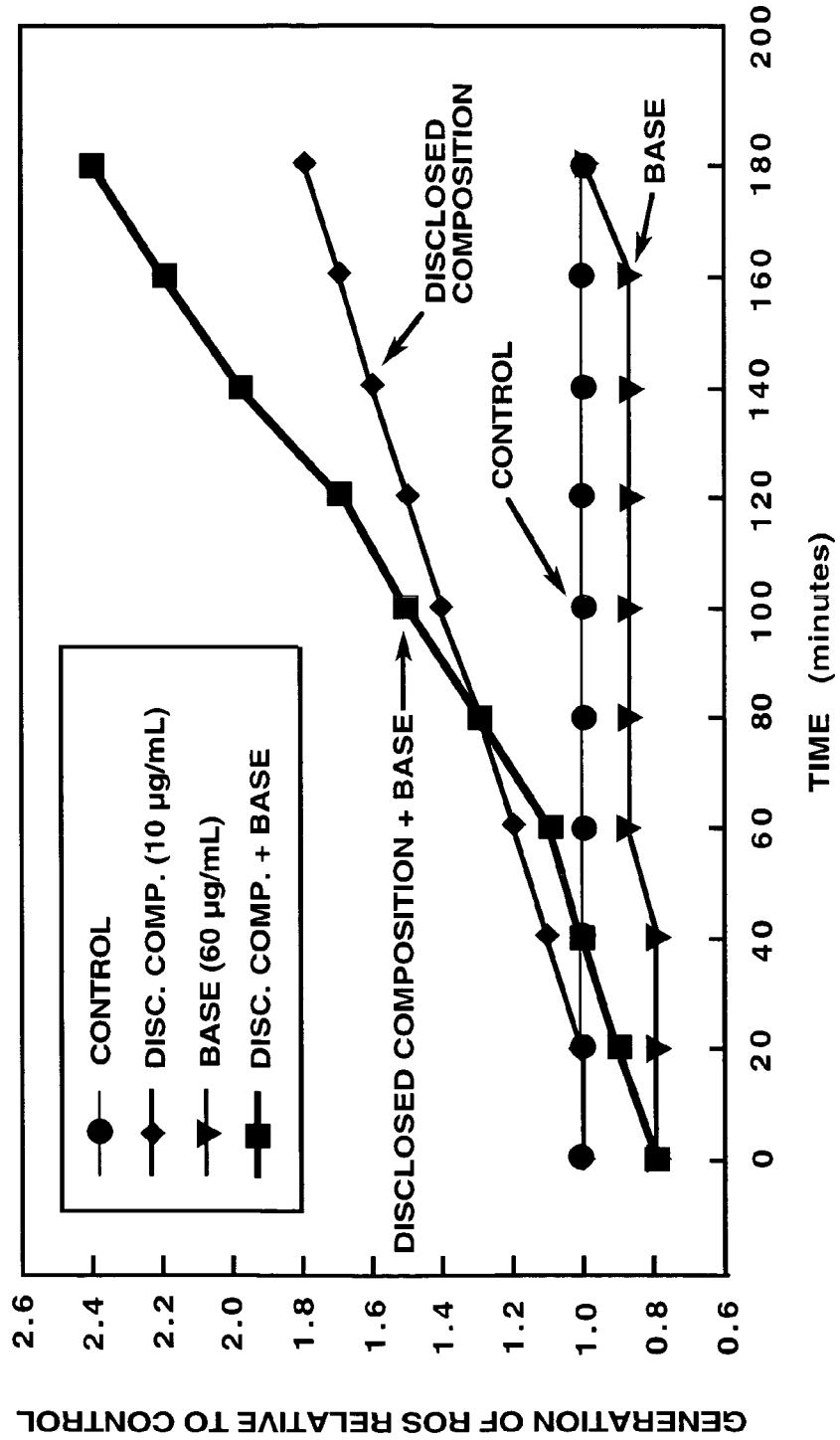
FIG. 1 is a graph of the release of ROS by HT29 human-colon adenocarcinoma cells by iron dextran alone and the Composition alone and in combination after 24 hours pre-incubation.

This disclosure relates to a Composition which can selectively exploit chemical variations and requirements between normal cells and cancer cells to inhibit and/or prevent the proliferation of cancerous cells in mammals. Most cancer treatments are unfocused and detrimentally affect healthy cells as well as cancerous cells in contact with the treatment because of a lack of specificity in traditional treatments. The ability of the disclosed Composition to exploit these chemical differences and requirements, and target cancer cells focuses the therapeutic agent to the desired cells and limits effects on healthy cells of a mammal. The disclosed chemical Composition, therefore, provides a chemotherapeutic that is less toxic with reduced side effects. This disclosure relates to the addition of glucose, copper and iron compounds to cancer cells, cell proliferating diseases (such as pre-cancerous cells, psoriasis, and so on), hyper proliferative disorders, myelodysplasia disorders, plasma cell dyscrasias, solid tumors, liquid tumors, and metastatic diseases to shrink tumors by killing tumor cells and/or arresting their growth. The Composition employs agents, which have been shown to be effective anti-cancer agents in the Examples below, although recurrently the subject of research with respect to the withholding, restricting, limiting and modulating intended to block initiation, promotion, and growth of tumors and metastasis of cancer cells.

The Composition is comprised of, at least, nanoparticles of a fixed copper compound core, or a fixed copper-iron compound core, or a combination of the two. These cores may be encapsulated, coated, adsorbed, complexed, or the like, with a protective sheath or jacket which also functions to target cancer cells. This sheath or jacket may be any combination of materials, such as a glucose or liposome, and, optionally, the resulting glucose encapsulated core may be coated with liposomes. In another embodiment, the core may be encapsulated with dextran alone or any glucose or combination of sugar-based substances. Alternatively, a liposome encapsulated core may then be coated with an outer dextran sheath.

As transition metals, copper and iron can generate reactive oxygen species including hydroxyl radicals. It is widely recognized that transition metals, including $Cu^+$, $Fe^{2+}$, $Sn^{3+}$, $Co^{2+}$ and $Ni^{2+}$, have been demonstrated to cause catalysis of free-radical reactions in biological systems. Therefore, cancer cells can be destroyed by digestion and fragmentation, which can be achieved by oxidation by copper or iron, and/or catalyzed free-radical chemical reactions. The $Cu^{2+}$ associates with the guanine-cytosine base pairs of DNA to cause local free-radical damage to the DNA that is characteristic of attack by hydroxyl ion. Copper is a promoter of free-radical damage to lipids, proteins, and especially to DNA and its base pairs. (Aruoma, *Copper ion-dependent damage to the base Pairs in DNA in the presence of hydrogen peroxide*, Biochem. Jour., 273: 601-4(1991)). In addition to the generation of oxygen species, the transitional metals, copper and iron, may be limiting nutrients to the growth and replication of cancer cells in mammals, as has been demonstrated in many in vitro, mammalian studies.

Suitable copper compounds for use as the core are any biologically acceptable copper compounds which include, but are not limited to, any fixed coppers including, cupric hydroxide, copper oxide, copper oxychloride, cupric carbonate basic, copper sulfate, copper sulfate basic, cuprous oxide, cupric hydroxide-iron hydroxide, copper-iron oxide, cupric citrate, cupric glycinate, cupric gluconate, cupric phosphate, cuprobam, cupric salicylite, indigo copper, cupro-cupric sulfate, cuprous sulfate, cuprous sulfate hemihydrite, any of the natural copper containing minerals such as cupric sulfate basic, the minerals brochantite, langite, malachite, azurite, cheesylite, cornetite, dihydyrite, libethenite, phosphorochalcite, pseudolibethenite, pseudo-malachite, tagilite, antlerite, covellite, marshite, cuprite, chalcocite, Rogojski's salt, brochantite, hydrocyanite, chalcanthtite, and the like, or any copper minerals occurring in nature such as nantokite or dolerophane and so on. See also, for examples of copper compounds, Merck's Manual 13$^{th}$ ed., Merck & Co. 2001, and Hawley's Condensed Chemical Dictionary 14$^{th}$ ed., John Wiley & Sons, Inc. 2001. Copper hydroxide, a fixed copper, is a preferred compound to form the core. In another embodiment, the core may also be composed of cupric hydroxide-iron hydroxide to provide a synergistic effect, which enhances the cellular toxicity of both the copper and iron. In one embodiment, any biocompatible form of copper compound that can cause catalysis of free-radical reactions in biological systems may be used as a core metal for the disclosed Composition. A biologically acceptable copper compound as defined herein is a copper compound, which may be used with and within a biological system with little or no detrimental effect, i.e. it does not appreciably alter or appreciably affect in any adverse way, the biological system into which it is introduced.

In a further embodiment, a combination of copper oxide, copper hydroxide-iron hydroxide or another of the fixed coppers and iron, may be used as a core to provide synergistic effects of the combination. Any biocompatible iron compound may be used in conjunction with the copper core, including without limitation, for example, $Fe^{3+}$, and its salts, iron hydroxide, iron oxyhydroxide, iron oxide, iron glucose, ferric citrate, Ferritin, ferrous fumarate, ferrous sulfate, and the like, to iron load the biological environment, including iron-saturated human holotransferrin.

The nanoparticles of the disclosed Composition preferably can be encapsulated, surrounded, complexed, or adsorbed by, and bound to, at least one sheath or coat that is preferably composed of a sugar substance, such as a glucose, a saccharide, a polysaccharide e.g. starch, cellulose, dextrans, alginides, chitosan, pectin, hyaluronic acid, pullulan (a bacterial polysaccharide), dextran, carboxyalkyl dextran, carboxyalkyl cellulose and the like. These dextrans can include, for example, those disclosed by Mehvar, supra (2000); and *Recent Trends in the Use of Polysaccharides for Improve Delivery of Therapeutic Agents: Pharmacokinetic and Pharmacodynamic Perspectives*, Curr. Pharm. Biotech. 4:283-302 (2003), and liposomes coated with dextran as disclosed by Moghimi, et al., *Long-Circulating and Target-Specific Nanoparticles: Theory to Practice*, Pharm. Rev., 53(2):283-318 (2001)) both of which are incorporated herein in their entirety. The sheath encoats, or encapsulates, the disclosed Composition's core and prevents chemical interaction of the core with the surrounding environment, blocking the degradation of the core and the emanation of the copper and/or iron from the copper compound, and/or the copper-iron compound from the core. The thickness of the sheath may be varied, if desired, by those skilled in the art. Because the sheath is composed primarily of a substance that is not necessarily recognized by the body as foreign matter, the body is less likely to develop a resistance to the Composition. In one embodiment, the sheath can be composed of dextran, also known as macrose, a high molecular weight polysaccharide. Dextran is an ideal candidate for use as a sheath because it is often administered to mammals as a blood plasma substitute or expander, is generally not rejected by the mammalian system, and can remain in the plasma for an extended period of time. Other biocompatible materials for the formation of a polymeric shell, sheath, or jacket can include proteins, polypeptides, oligopeptides, polynucleotides, polysaccharides, lipids and so on. Additional sheath materials include, for example, those of U.S. Pat. Nos. 6,096,331; and 6,506,405, incorporated herein in their entirety. Alternatively, combinations of two or more of the above named materials may be used to form the sheath.

In another embodiment, the disclosed Composition can be sheathed or encapsulated with a liposome coat. This liposome coat may be the sole sheath encapsulating the core, or may be a second coat over one, or a combination, of the above named materials. PEG liposome polymer coatings have been shown to reduce phagocytic system uptake and provide long residence time according to research by the Alza Corporation, *Delivery Times, Issues and Opportunities*, Vol 2 (1), incorporated herein in its entirety. Residence time in the plasma can be extended to periods of at least several days to weeks after IV injection without releasing the encapsulated drug, which would lower the administration frequency of the drug. See, e.g., U.S. Pat. No. 6,465,008; U.S. Pat. Pub. US 2002/017271181; U.S. Pat. Pub. US 2001/005118381; each of which is incorporated herein in its entirety.

Alternatively, the core may be transported to cell-specific sites with the use of targeting agents or markers which may target cancer cells, cell proliferating diseases (such as precancerous cells, psoriasis, and so on), solid tumors, liquid tumors, and metastatic diseases. Any targeting agent or marker which can medicinally utilized within a biological system may be employed to actively transport the core to the specific site of the cancer cells (See, for example, R. C. Juliano, Targeted Drug Delivery, Handbook of Experimental Pharmacology, Vol. 100, Ed. Born, G. V. R. et al., Springer Verlag). For example, a binding molecule to a cancerous cell surface site or cell surface receptor, surfactant, a ligand, an antibody, proteins, peptides, enzymes, specific chemical compounds, and so on, may be used as targeting agents or markers to target cancer cells. These targeting agents or markers may be used instead of, or in conjunction with, at least one sheath encapsulating the core.

The nanoparticle size of the entire disclosed Composition may be approximately 1 nm to approximately 10,000 nm. In a more preferred embodiment, the particle size may be approximately 15 nm to approximately 500 nm. A most preferred embodiment for particle size is approximately 20 nm to approximately 200 nm.

Empty liposomes, which are devoid of drugs, may be co-administered or administered before, during, or after the Composition itself to the patient, to function as a decoy, placebo carrier, or redistribution agent with respect to the phagocytic system and allow the Composition to remain in the plasma for an extended period of time. The empty liposome decoys, or placebo carriers, occupy the phagocytic system and also redistribute the disclosed composition away from clearance by cells in the liver and in the spleen and thus concentrate the disclosed composition in the plasma for an extended period of time. Biocompatible materials used for polymeric shells may also be employed as decoys, alone or in combination with liposomes.

Iron dextran is also an exemplary example of a biocompatible iron compound which iron loads tissues through at least two different pathways, and works advantageously with the disclosed Composition as a redistribution agent. The first is phagocytosis by cancer cells through an extended human plasma residence time. The second is increasing the transferrin saturation through processing of the iron dextran through the phagocytic system. The intra-cellular metabolism of iron dextran within a tumor cell increases the acidity of the environment, which further promotes the breakdown of the disclosed Composition. For the purposes of this patent application, phagocytosis and endocytosis are defined as the uptake of material, including particulate materials, into a cell by the formation of a membrane vesicle, and are used herein as equivalent terms.

In one embodiment, the disclosed composition plus iron dextran plus empty liposomes may be added to the total parenteral nutrition ("TPN") for the cancer patient. The disclosed composition includes essential trace elements of copper, and may include iron, as well as glucose, and/or liposomes, which are fats, to contribute to the patient's bodily requirements. Thus the Composition also provides an important contribution to the total parenteral nutrition of the patient.

In yet another embodiment, the Composition may be used with insulin potentiation therapy ("IPT"), with or without iron dextran, to promote the ingestion of these agents of the invention into the tumor cell. (Hauser & Hauser, *Cancer-Treating Cancer with Insulin Potentiation Therapy*, Beulah Land Press, p 267 (2001)).

Without being limited, held, or bound to any particular theory or mechanism of action, it is believed that the Composition, the redistribution agents, i.e., iron dextran with or without empty liposomes, enters the system, traffics throughout the body as an inert entity, and is removed from the plasma by the phagocytic system and/or cancer cells. The Composition functions as a prodrug, it is inert in the plasma and active intracellularly within cancer cells. The Composition can remain in the mammal's plasma for a period of many days, depending on the dosage levels, when used with a redistribution agent or placebo carrier. (It is known that iron-dextran can remain in the plasma for weeks, especially when doses are administered above the clearance rate of the phagocyte system. The processing of the iron dextran by the phagocytic system is rate limited to a daily maximum amount, leaving the balance for future use.) The sheath may not be immediately recognized as foreign matter by the phagocytic system because it is a sugar-based substance and is not rejected by the mammalian system, allowing the Composition to remain in circulation of the mammal for a longer period than most therapeutics, making it more likely to come into contact with target cells and providing more efficacy with fewer doses than traditional chemotherapeutic agents. The Composition circulates, via any biological pathway, throughout the body and may contact any cell type. For the most part, the phagocytic system takes up the Composition, as do cancer cells which have a high affinity to phagocytize molecules necessary for proliferation, such as sugars. Normal, healthy cells generally have very little interaction with the Composition. The Composition that is taken up by the phagocytic system is processed, to a large degree, through the liver in hepatocytes that store glucose, iron, and copper and are later released through their appropriate protein carriers to feed and nurture cells of the body. Since sugars, copper, and iron are bodily requirements, well known to the phagocytic system, the phagocytic system is able to process, transport, store, or eliminate them with little toxicity, while the Composition kills cancer cells and simultaneously feeds and nourishes cells in the body.

When the Composition is phagocytized by cancer cells, or enters the cells by other means, the Composition is exposed to the cells' acidic environment, including lactic acid, caused by the anaerobic glycolysis process which is common to cancer cells. Any iron dextran that may be present in the cell also contributes to the acidity of the environment during the breakdown of the iron dextran compound. The sugar sheath is metabolized and the core of the disclosed Composition breaks down under acidic conditions, generating at least free ions, free radicals, and reactive oxygen species ("ROS"). The free radicals taken together with the free transition metal ions have cytotoxic effects on the cells and generate DNA-damaging free radicals and ROS. The free radicals and ROS prevent replication of the cell and, eventually, cause cell death. In contrast, normal healthy cells generally process glucose aerobically, without lactic acid production. Therefore, if phagocytized by normal cells, the sheath is not readily broken down and the metal core remains safely encapsulated in the sheath, which buffers the cellular toxicity of the core.

Copper is well known to those skilled in the art as a potent viricide. In vitro testing has shown that copper with hydrogen peroxide kills surrogate models of virtually every microorganism afflicting mammals. (See, Sagripanti, et al., *Virus Inactivation by Copper or Iron Ions alone and in the Presence of Peroxide*, Applied and Environ. Microbio, 59:12, 4374-4376 (1993); Sagripanti, *Metal-based Formulations with High Microbicidal Activity*, Applied and Environ. Microbio, 58:9, 3157-3162 (1992)). The disclosed composition has also been shown effective as a potent viricide, and without being bound to a particular theory or mechanism, it is believed that the viricidal action functions as described above to disrupt the viral DNA and rupture the viral envelope. The disclosed Composition can be useful to destroy those viruses known to cause cancer, such as, for example, HBV and HCV for hepatocellular carcinoma, HPV for cervical cancer, EBV (Epstein-Barr virus) for Burkitt's lymphoma, and HTLV 1 for a form of leukemia. Thus the disclosed composition, with or without the addition of the iron-dextran base, is active in the pre-cancerous stages, before the cells become fully transformed. The disclosed composition may advantageously traffic throughout the body, including the central nervous system and brain.

The administration of iron compositions and/or iron dextran compositions may be combined with the disclosed Composition to provide synergistic reactions between the copper and iron for enhanced cellular toxicity. The synergy between copper and iron is known in the art, and has been described in the literature, see, for example, U.S. Pat. No. 5,202,353, incorporated herein in its entirety, which discloses use of the synergistic affects of copper compositions and iron compositions for use as fungicides and bactericides. The iron compositions and/or iron dextran compositions may also be administered to redistribute the disclosed Composition and allow the Composition a longer residence time in the patient's plasma. Far higher dosages of iron dextran may be employed, than that of elemental iron salts, for a greater cytotoxicity, and a protracted residence plasma time. The greater the iron level, the greater the synergistic cytotoxicity of the Composition. Because it is well known in the art that the phagocytic system removes the smaller particles from the plasma circulation first, the combination of the iron dextran with a smaller diameter than the Composition allows a protracted plasma residence time. The diameters of the iron dextran and the core of the disclosed Composition may be varied to manipulate the plasma time of these particles as desired. In one embodiment, the iron dextran can be administered above the clearance level of the phagocyte system, which can serve as a decoy, placebo carrier, or redistribution agent to allow the Composition to remain in the plasma for an extended period of time. (See, Henderson & Hillman, *Characteristics of Iron Dextran Utilization in Man*, Blood, 34(3):357-375(1969)). This use of iron dextran at a dose above the rate of clearance of the phagocyte system, to allow the disclosed Composition to remain in the plasma for an extended period of time, is known in the art as a redistribution (away from the liver and spleen to the plasma). Generally, smaller doses of iron dextran (50-500 mg) are cleared within approximately 3 days, larger doses of iron dextran (>500 mg), however, are cleared at a constant rate of 10-20 mg/hr and are typically associated with increased plasma concentration of iron dextran for as long as 3 weeks. Other agents which may serve as decoys for the phagocytic system to redistribute the disclosed Composition to the plasma include, without limitation, pullulan, dextran sulfate, empty liposomes, and those taught by U.S. Pat. Nos. 6,506,405, and 6,096,331 incorporated herein in their entirety.

Experiments on metabolic clearance rates done on cynomolgus monkeys (species Macaca fascicularis) have shown the safe use of large dosages of elemental iron derived from iron dextran. (All experiments were preformed in compliance with the Animal Welfare Act and Regulations.) Dosages of 400 mg and 500 mg of elemental iron, derived from iron dextran, per kg of body weight were safely administered to the cynomolgus monkeys by intravenous infusion. The iron dextran showed a protracted plasma residence time which functions as a decoy for the phagocytic system to redistribute the disclosed Composition to the plasma with few negative side effects. As shown in FIGS. 15A, B and C, the administered iron dextran remained in the monkey plasma for at least 120 hours, at milligram levels. Single dosages of iron dextran were also separately administered to monkeys, as shown in FIG. 16, with few negative side effects, i.e. abdominal swelling. The monkey model clears the iron dextran from the system much more very rapidly, as compared to humans, because of a higher metabolic rate. Therefore, a longer plasma residence time is anticipated in humans, as has been shown in research, such as, for example, Henderson & Hillman, (1969).

The side effects of the Composition, with or without the addition of an iron dextran compound, are far fewer than the well-known side effects of the standardly administered chemotherapy, although the disclosed Composition can be used in conjunction with additional therapeutic agents. The disclosed Composition and iron dextran have breakdown byproducts of copper and iron, which support the bio-production of red blood cells, white blood cells and platelets. Because the Composition supports the hemopoietic system, its use limits or eliminates the well-known devastating fatigue, risk of infection, and the adverse effects of cytotoxic chemotherapy on the bone marrow (and other quickly growing cells) that are standardly caused by commonly used chemotherapy agents. In addition, the use of ancillary medications such as colony stimulating factors to accelerate bone marrow recovery and erythropoietin, a colony stimulating growth factor for red blood cells for the prevention of severe myelosuppression, and their severe side effects can be restricted. Since the need for the use of these drugs can be restricted, the quality of life of the patient may be improved.

For diagnostic purposes, the Composition may be labeled with magnetic targeted carriers to allow imaging of the cancer cells and provide information to determine further medical treatments, including targeting tumors with external magnets. (Johnson, *An Innovative Drug Delivery Technology*, Magnetics Business & Technology Magazine, (2002)). A wide variety of other labels may be employed, such as radionuclides, fluors, enzymes, enzyme substrates, enzyme co-factors, enzyme inhibitors, ligands (particularly haptens), etc., and are well known to those skilled in the art.

Since the disclosed composition, iron dextran, and empty liposomes are all formed of biocompatible materials, all may be administered over an extended period of time as compared to other chemotherapeutic agents. The effective dose or effective amount can vary subject to the evaluation of the those of skill in the art in relation to the particular type of cancer, the regimen of administration, the body weight of the subject, the aggressiveness of the cell growth and the degree in which the subject has been negatively affected by prior chemotherapy. In general, a therapeutically effective amount is that which decreases, or at minimum prevents further growth, of a primary or metastatic tumor.

The disclosed Composition can be administered to a patient as a pharmaceutical composition in combination with a pharmaceutical carrier. A pharmaceutical carrier can be any compatible, non-toxic substance suitable for delivery of the Composition to the patient that is medically acceptable. Sterile water, alcohol, fats, waxes, and inert solids may be included in the carrier. Pharmaceutically accepted adjuvants (buffering agents, dispersing agent) may also be incorporated into the pharmaceutical compound. In one embodiment, the Composition may be combined with sterile water, or deinozed water and free dextran, dextran free of drug, to form a sterile colloidal suspension.

The disclosed Composition may be administered to a patient in a variety of ways, such as oral, intravenous, subcutaneous, intraperitoneal, intrathecal, intramuscular, intracranial, inhalational, topical, transdermal, suppository (rectal), pessary (vaginal) or an implantable polymer disclosed composition saturated depot or wafer, such as, for example, a Giladel wafer®. Preferably, the pharmaceutical compound may be administered parenterally, e.g., subcutaneously, intramuscularly or intravenously. Thus, the disclosed Composition may include a solution dissolved in an acceptable carrier, preferably an aqueous carrier, for parenteral administration. A variety of aqueous carriers can be used, e.g., water, buffered water, 0.4% saline, 0.3% glycine and the like. These solutions are sterile and generally free of particulate matter. These compounds may be sterilized by conventional, well-known sterilization techniques. The Composition may contain pharmaceutically acceptable auxiliary substances as required to approximate physiological conditions such as pH adjusting and buffering agents, and if necessary for sensitive patients, toxicity adjusting agents and the like, for example sodium acetate, sodium chloride, potassium chloride, calcium chloride, sodium lactate, etc. The concentration of the disclosed Composition in these formulations can vary widely, e.g., from less than about 0.1 mg to about 5 mg, ranging to as much as 10 mg or 15 mg or more of the equivalent of elemental copper derived from the Composition per ml of carrier. The preferred concentration of the disclosed Composition is approximately 5 mg of the equivalent of elemental copper derived from the Composition per ml of carrier, and will be selected primarily based on fluid volumes, viscosities, etc., in accordance with the particular mode of administration selected. The preferred pH range for use with the disclosed Composition is between approximately 7 and approximately 8.5, and the more preferred pH range is between approximately 7.5 and approximately 8.0.

Actual methods for preparing parenterally administerable compounds and adjustments necessary for administration to patients, typically mammals, will be known or apparent to those skilled in the art and are described in more detail in, for example, *Remington's Pharmaceutical Science: The Science and Practice of Pharmacy*, 20$^{th}$ Ed., Lippincott, Williams & Wilkins; (2000), which is incorporated herein by reference.

It will be appreciated that the disclosed Composition addresses the very pressing problem of targeting cancer therapy for specificity, while greatly limiting or eliminating the horrendous side effects of chemotherapy. Moreover, the disclosed Composition, especially when used with iron dextran, can overcome the difficulties of drug resistance. The disclosed composition may be employed with or without the iron dextran loading, to accomplish highly effective treatment against solid tumors, liquid tumors (blood), as well as metastatic cancers, while providing an agent that is cost effective because low dosages produce high activity and results. The disclosed Composition is designed to be administered by itself as an chemotherapeutic agent, with iron dextran, and/or in conjunction with conventional cancer therapies. Most importantly, the Composition's highly targeted and highly efficient cell kill rate can save innumerable lives at a cost effective rate that can be made available to any medical facility. For example, the disclosed Composition is very well suited to treat hepatocellular carcinoma, with or without iron loading. Hepatocellular carcinoma ("HCC") is the most common, primary cancer of the liver, and causes over 550,000 deaths annually, worldwide. Heretofore, no significantly effective treatments existed for HCC. (Nakakura & Choti, *Management of Hepatocellular Carcinoma*, Oncology, 14(7) (2000)). The disclosed Composition, however, may be introduced to the blood stream, and traffic through the hepatic artery to expose the normal hepatocytes and the cancerous hepatocytes to the Composition. The hepatocytes breakdown the dextran to use or store glucose as glycogen, and may also store copper and iron that is derived from the Composition. Thus, the HCC cell is subject to the cytotoxicity caused by the disclosed Composition. Any excess copper that is not stored, may be excreted through the biliary, and other bodily systems. Copper and iron from the hepatocytes are bound to the respective protein carriers, which include transferrin and ceruloplamin to feed the cells of the patient's body.

The following examples are intended to illustrate but not limit the invention. While they are typical of those that might be used, other procedures known to those skilled in the art may alternatively be used.

EXAMPLES

Example 1

An in vitro human tumor screen was used to evaluate anti-proliferative effects of the disclosed Composition and the Composition in combination with the Base Compound of iron dextran. Human tumor cell lines representing models of cancers with the greatest incidence, greatest increase of incidence, the greatest mortality, or cancers that are highly resistant to treatment were selected. The testing was conducted using standard tissue culture techniques that are well known in the art and the $^3$H-thymidine assay for analysis.

Experimental Design

This experiment was designed to evaluate the anti-proliferative and cytotoxic effects of the disclosed Composition alone, and in combination with Base Compound, and doxorubicin, also known by its trade name Adriamycin, as a positive control which is a mainstay in the treatment of many cancers used in combination with various chemotherapies (See, Chu and Devita, *Cancer Chemotherapy Drug Manual* 2003, Jones and Bartlett Publishers, pg 138-139. (2003)) on the human tumor cell lines CAK-1 renal, DLD-1 colon, LOX IMVI melanoma, MCF7 mammary, NCI-H23 lung, NCI-H460 lung, OVCAR-3 ovarian, PC-3 prostate, SNB-75 CNS, ZR-75-1 mammary, and CEM-SS leukemic cells. See, FIG. 14. For all experiments, the cells were harvested, centrifuged to remove the media, and suspended in fresh complete medium. Samples were taken to determine cell density. All cell counts were determined with a Coulter Model $Z_1$. cell counter (Beckman Coulter, Inc. Fullerton, Calif.) and viability was measured with propidium iodide staining followed by analysis on a Coulter EPICS XL flow cytometer (Beckman Coulter, Inc. Fullerton, Calif.). All cell lines were each plated at $5 \times 10^3$ cells per well in complete medium. The following day, the cells were dosed with 8 dilutions of the Composition alone and the Composition in combination with the Base Compound of iron dextran (60 μg/mL, which is the equivalent of elemental iron derived from iron dextran). All iron dextran amounts are measured as the approximate equivalent of elemental iron derived from the iron dextran. The Base Compound of iron dextran was also run alone as a control. The plates were analyzed on Day 4 after the initiation of treatment.

The Composition was formed as follows: An inorganic copper salt, 4.854 g of copper nitrate (99.999%), was dissolved in 20 ml deionized water (Molecular Biology Reagent from Sigma-Aldrich), or distilled water could also be used. This solution was refluxed for approximately two hours. The copper salt solution was reacted with 2 g of oxidized dextran or 2 g of hydrogenated dextran at low temperature. (Clinical grade dextran, D4751 with an average molecular weight of 64,000-78,000, was purchased from Sigma-Aldrich.) This solution was refluxed for 1 hour before adding 0.2 ml of 0.5 M NaOH in the solution. After refluxing the solution for another two hours, it was divided in half. Half of the solution was combined with 2 g of oxidized dextran, and 40 ml of water were added, and followed by a two-hour refluxing step. The second half of the solution was combined with hydrogenated dextran, 40 ml of water were added, and followed by a two-hour refluxing step. The solutions were then each combined with 0.1 ml of 0.5 NaOH, and the reflux was continued for an additional two hours. The solutions were allowed to cool to room temperature. The resulting solution of a $Cu(OH)_2$-dextran nanoparticles were precipitated in a controlled manner, wherein each $Cu(OH)_2$ nanoparticle is covered by dextran molecules by adding 120 cc of 0.25 M NaOH to the final solutions. The water content of the solutions was evaporated in a vacuum to increase the copper concentration in the solutions. The precipitates with large particles were centrifuged to prepare the aqueous solutions of $Cu(OH)_2$-dextran nanoparticles. The final copper concentration in the solutions was typically approximately 5 mg/ml and the final pH ranges from approximately 7.5 to approximately 8.5, and was assayed by atomic absorption spectrometry and/or inductive coupled plasma spectrometry. The particle size of the $Cu(OH)_2$-dextran nanoparticles was determined by laser light scattering.

The particle size for oxidized dextran was in the range of approximately 150 nm to approximately 200 nm and for hydrogenated dextran was in the range of approximately 20 nm to approximately 50 nm. After determining the particle size, the solutions were tested for free copper ions using a copper electrode. The copper specific electrode was calibrated with four known copper concentrations solutions. These concentrations were as follows: 0.1 moles/liter, 0.01 moles/liter, 0.001 moles/liter and 0.0002 moles/liter (~1 ppm). The millivolt readings of four standard Cu2+ solutions were, respectively:

| Cu2+ Conc. | mV |
|---|---|
| 0.1M | 239 |
| 0.01M | 206 |
| 0.001M | 175 |
| 0.0002M (1 ppm) | 163 |

The mV reading for these copper solutions was typically less than 130 mV, which suggest that free Cu2+ concentration in solutions is less than 1 ppm, and often lower than the level of detection. (As a point of reference, the Environmental Protection Agency allows 1.3 ppm of copper in drinking water, see, for example, a website of the United States Environmental Protection Agency on safe water, and possible contaminants of drinking water, including copper.) The colloidal suspensions of the disclosed Composition in all samples had little free copper detected, typically approximately below the levels of detection of 1 ppm. The copper hydroxide solution prepared using oxidized dextran had a pH of 8.5. The solution formed with hydrogenated dextran exhibited no free copper ions, typically below the levels of detection of 1 ppm.

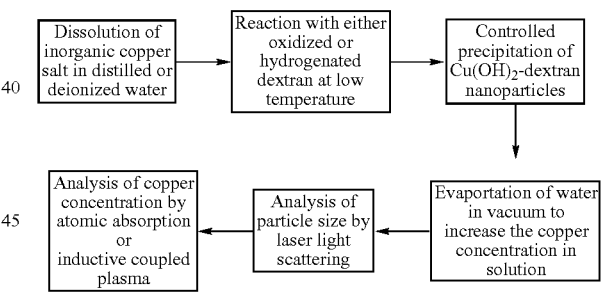

Preparation of Copper Hydroxide-Iron Hydroxide Nanoparticles (a) Preparation of Sample 1

A copper salt, 2.428 g, of Cu nitrate (99.999% pure, Alfa Aesar, catalog # 10699) was combined with 0.2 g of $FeCl_3$, $6H_2O$ (purity 97-102%, Alfa Aesar, Catalog # 12497), and 4.0 g of hydrogenated dextran. These components were dissolved in 70 ml of deionized water (Molecular Biology Reagent from Sigma-Aldrich). This solution was then refluxed for approximately 3 hrs. The solution was allowed to cool before adding 92.8 cc of 0.25M NaOH (Fisher ACS, catalog # S318-3) into the solution. The final pH of the solution was 8.5. After 6 days, pH decreased to 6.85, and 1.7 cc of 0.25M NaOH solution was added to adjust the pH to 8.5. Analysis of the copper and iron concentration in solution was done by atomic absorption spectrometry ("AA") and/inductive coupled plasma spectrometry ("ICP"). The solution was syringe filtered, and the dark green solution was stored in sterile vials. Iron oxyhydroxide may also be employed as a substitute for iron hydroxide in this or any sample.

(b) Preparation of Sample 2

The copper salt, 2.428 g, of Cu nitrate (99.999% pure, Alfa Aesar, catalog # 10699) was combined with 0.4 g of $FeCl_3$, $6H_2O$ (purity 97-102%, Alfa Aesar, Catalog # 12497), and 4.2 g of hydrogenated dextran. These components were dissolved in 75 ml of deionized water (Molecular Biology Reagent from Sigma-Aldrich). This solution was refluxed for approximately 3 hrs. The solution was allowed to cool before adding 102.2 cc of 0.25M NaOH (Fisher ACS, catalog # S318-3) in the solution. The final pH of the solution was 8.5. After 6 days, pH decreased to 7.4, and 1.6 cc of 0.25M NaOH solution was added to adjust the pH to 8.5. Analysis of the copper and iron concentration in solution was done by AA and/ICP. The solution was centrifuged, and the dark green solution with slight haze was stored in sterile vials.

(c) Preparation of Sample 3

The copper salt, 2.428 g, of Cu nitrate (99.999% pure, Alfa Aesar, catalog # 10699) was combined with 0.2 g of $FeCl_3$, $6H_2O$ (purity 97-102%, Alfa Aesar, Catalog # 12497), 1.2 g of hydrogenated dextran, and 2.8 g dextran (MW=15,000). These components were dissolved in 70 ml of deionized water (Molecular Biology Reagent from Sigma-Aldrich). This solution was refluxed for approximately 3 hrs. The solution was allowed to cool before adding 83.2 cc of 0.25M NaOH (Fisher ACS, catalog # S318-3) into the solution. The final pH of the solution was 8.5. After 6 days, pH decreased to 7.64, and 0.6 cc of 0.25M NaOH solution was added to adjust the pH to 8.5. Analysis of the copper and iron concentration in solution was done by AA and/ICP. The solution was centrifuged, and the dark green solution was stored in sterile vials.

Cell Lines and Standard Agents

The cell lines were propagated using standard tissue culture procedures and seeded in microtiter plates prior to dosing. The control groups included a Base Compound (60 μg/mL) only treatment, complete medium control, and positive control (doxorubicin, 1 μM). For each concentration level of the Composition, eight replicates of each cell line were treated.

Cell Culture

The cell lines used in the following Examples are listed below in Chart 1. The Composition was tested on the listed solid tumors, and liquid tumors, but may be effectively used for any type of cancers. The cell lines were propagated under sterile conditions and incubated at 37° C. in HEPA-filtered $CO_2$ tissue culture incubators with 5% $CO_2$ and 95% humidity. Each cell line was sub-cultured weekly to bi-weekly or more frequently for use in experiments.

$^3$H (Tritiated)-Thymidine Assay

Anticellular effects of the compounds on the tumor lines were assessed with the $^3$H-thymidine DNA incorporation assay. Tritiated-thymidine was purchased as a 1 mCi stock and diluted 1:25 in media. One day prior to harvest, 25 μL (1 μCi) of the diluted $^3$H-thymidine was added to each well, and the plates were incubated overnight. The following morning the cells were harvested onto glass fiber filters using a Skatron cell harvester (Molecular Devices Corporation, Sunnyvale Calif.). The filters were then placed in scintillation vials and scintillation cocktail was added (Beckman Coulter, Inc. Fullerton, Calif.). The vials were then read on a Beckman LS6000IC liquid scintillation counter (Beckman Coulter, Inc. Fullerton, Calif.) and the data were reported as counts per minute (CPM). The data were transferred into Lotus 123 for processing.

For all cell lines, the cells were harvested, centrifuged to remove the media, and suspended in fresh complete medium. Samples were taken to determine cell density. The cell count was determined with a Coulter Model $Z_1$ cell counter (Beckman Coulter, Inc. Fullerton, Calif.) and cell viability was measured with propidium iodide staining. Analysis was then conducted on a Coulter EPICS XL flow cytometer (Beckman Coulter, Inc. Fullerton, Calif.). The cell lines were each plated at $5\times10^3$ cells per well in complete medium. On the second day, the cells were washed with 8 dilutions of the disclosed Composition alone, or in combination with the Base Compound at the concentration of 60 μg/mL. A control was run by washing cells with only the Base Compound. On day 4 after the initial treatment, the plates were analyzed. The results were summarized below:

TABLE 1

| Cell Line | $IC_{50}$ (μg/mL) Composition | $IC_{50}$ (μg/mL) Composition and Base Compound (60 μg/mL) |
| --- | --- | --- |
| CAKI-1 renal | 1.440 | 1.138 |
| DLD-1 colon | 1.430 | 0.196 |
| NCI-H23 lung | >10 | 1.718 |
| NCI-H 460 lung | 1.183 | 0.131 |
| LOX IMVI melanoma | 6.718 | 0.513 |
| MCF7 mammary | 2.213 | 0.972 |
| OVCAR-3 ovarian | 3.662 | 0.299 |
| PC-3 prostate | >10 | 1.869 |
| SNB-75 CNS | 0.895 | 0.095 |
| ZR-75-1 mammary | >10 | 2.031 |
| CEM-SS Leukemic 1 | 5.87 | |
| CEM-SS Leukemic 2 | 4.975 | |

The experiments, described below, performed on tumor cells lines are presented with results in Table 1, with the exception of the HT29 human colon adenocarcinoma cells. The Composition plus the Base Compound at 60 μg/ml resulted in 100% cell kill, with the exception of the CAKI-1 renal line, which resulted in 99% cell kill. Moreover, the further addition of increased base compound to composition increases the cytotoxicity, if necessary. In three cell lines that were resistant to Composition alone, up to 10 μg/ml, namely NCI-H23 lung, ZR-75-1 mammary and PC-3 prostate, resistance was completely overcome with the addition of Base Compound to the Composition, at 60 μg/ml, resulting in 100% cell kill. For all cell lines that were exposed to the Base Compound, the $IC_{50}$ was lowered significantly by the synergistic, ctyotoxic effects of the Base Compound in combination with the disclosed Composition, demonstrating enhanced cell kill with the addition of Base Compound. For all the cell lines that were exposed to the Base Compound, Composition with the Base Compound equaled or exceeded the cell kill of doxorubicin, a mainstay chemotherapeutic drug in the treatment of breast cancer and other cancers, which is well known to have many severe side effects.

Example 2

FIG. 1 The Release of ROS (reactive oxygen species) by HT29 Human Colon Adenocarcinoma Cell Line After 24-Hr Incubation.

The data were obtained after a 24 hour incubation of HT29 cells with 10 μg/mL of the disclosed Composition, 60 μg/mL of the Composition plus Base Compound, and 60 μg/mL of the iron dextran Base Compound alone. The assay depends on a non-fluorescent substrate added to wells in which cells are growing. Where ROS are present, the substrate is broken down to form a fluorescent product. The data in FIG. 1 demonstrates that the Composition produces ROS above the level of the control of fresh medium and the Base Compound. The data further demonstrates an increased production of ROS with the disclosed Composition in combination with the Base Compound, above that of the disclosed Composition or the Base Compound alone.

The combination of the disclosed Composition and the Base Compound generates a significant amount of ROS, as do radiation treatments for cancer patients, which is generally believed to exert its cytotoxic effect by the generation of DNA damaging free radicals. The combination of the disclosed Composition and the Base Compound can be used in conjunction with radiation treatment can increase the amount of cancer killing free radicals generated by radiation and exert increased cell-kill over radiation alone. This is known in the art as a radio sensitizer, compounds which amplify and potentiate the cytotoxic effect of radiation.

Example 3

Figure 2A:
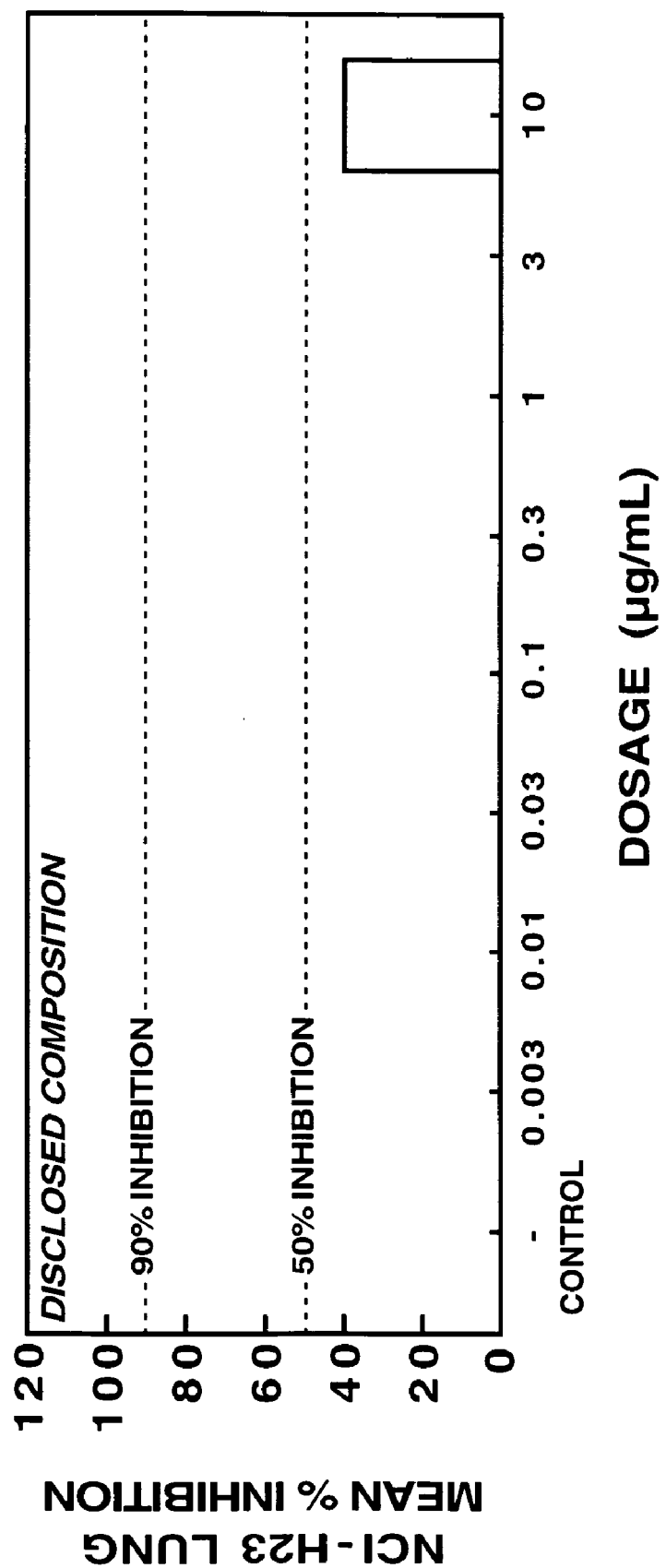
FIG. 2A is a graph of the concentration of the Composition alone plotted against NCI-H23 lung cells mean percent inhibition.

FIG. 2A discloses a graph of the mean inhibitory concentration of the disclosed Composition against the NCI-H23 lung cells. The inhibitory concentration 50 ("$IC_{50}$") is defined as the concentration of the employed composition or compound that is inhibitory or effective on 50%, or more, of the cells used in an experimental procedure. The disclosed Composition has a highly effective $IC_{50}$ level of approximately 10 µg/ml when applied to NCI-H23 lung cells. FIG. 2B provides the absorbance values of the disclosed Composition, the Base Compound, doxorubicin, and a control for the NCI-H23 Lung cells in both media and MTS reagent (Promega, Madison Wis., U.S.). The MTS reagent is a tetrazolium salt that it is converted to a colored compound of formazan when applied to live cells, with the emission of light at approximately 490 nm. The disclosed Composition inhibited forty percent of the cultured NCI-H23 Lung cells at a dosage 10 µg/mL. Although doxorubicin exhibited a high inhibitory effect, it is also known to have many detrimental side effects when used in vivo, which the disclosed Composition will not cause. The absorbance value units are also given and some background absorbance was assumed to have occurred, and typically ranges between 0.2-0.4 units after 4 hours of incubation. FIG. 2C discloses the expected theoretical absorbance levels of the disclosed Composition for varying IC levels.

Figure 2D:
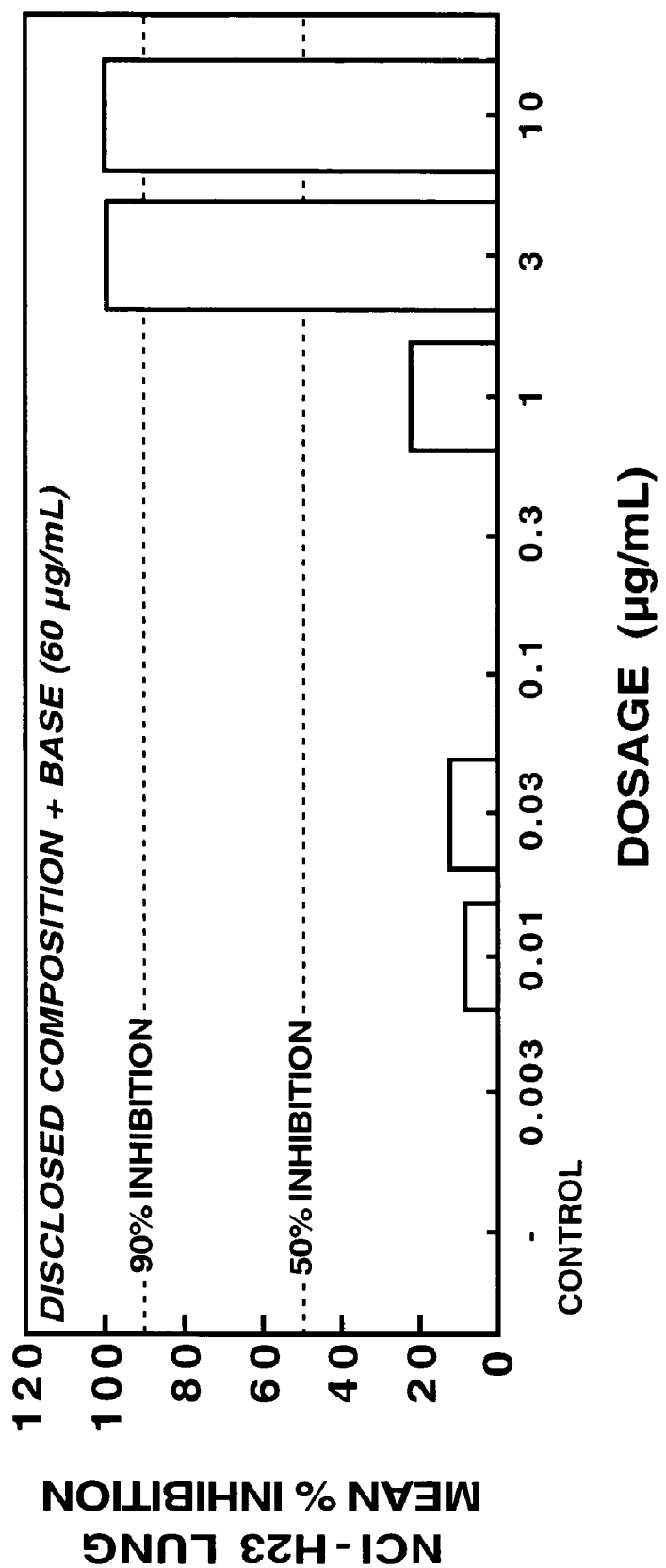
FIG. 2D is a graph of the concentration of the Composition plus Base Compound plotted against NCI-H23 lung cells mean % inhibition.

As shown in FIG. 2D, the NCI-H23 lung cells showed little or no resistance to both the 3 µg/mL and 10 µg/mL dosages of the Composition with the addition of the Base Compound. This combination of the Composition with the addition of the Base Compound resulted in over a 99-100% inhibition of the cells in vitro, which equals that of doxirubicin. The concentration of the Composition together with the Base Compound was 60 µg/mL. FIG. 2E shows the absorbance values and inhibition percentages of the Composition plus Base Compound combination, which demonstrated 100% inhibition of the NCI-H23 lung cells at the low dosage of 10 µg/mL. FIG. 2F show the statistical results of the regression output for the experiments.

Example 4

Figure 3A:
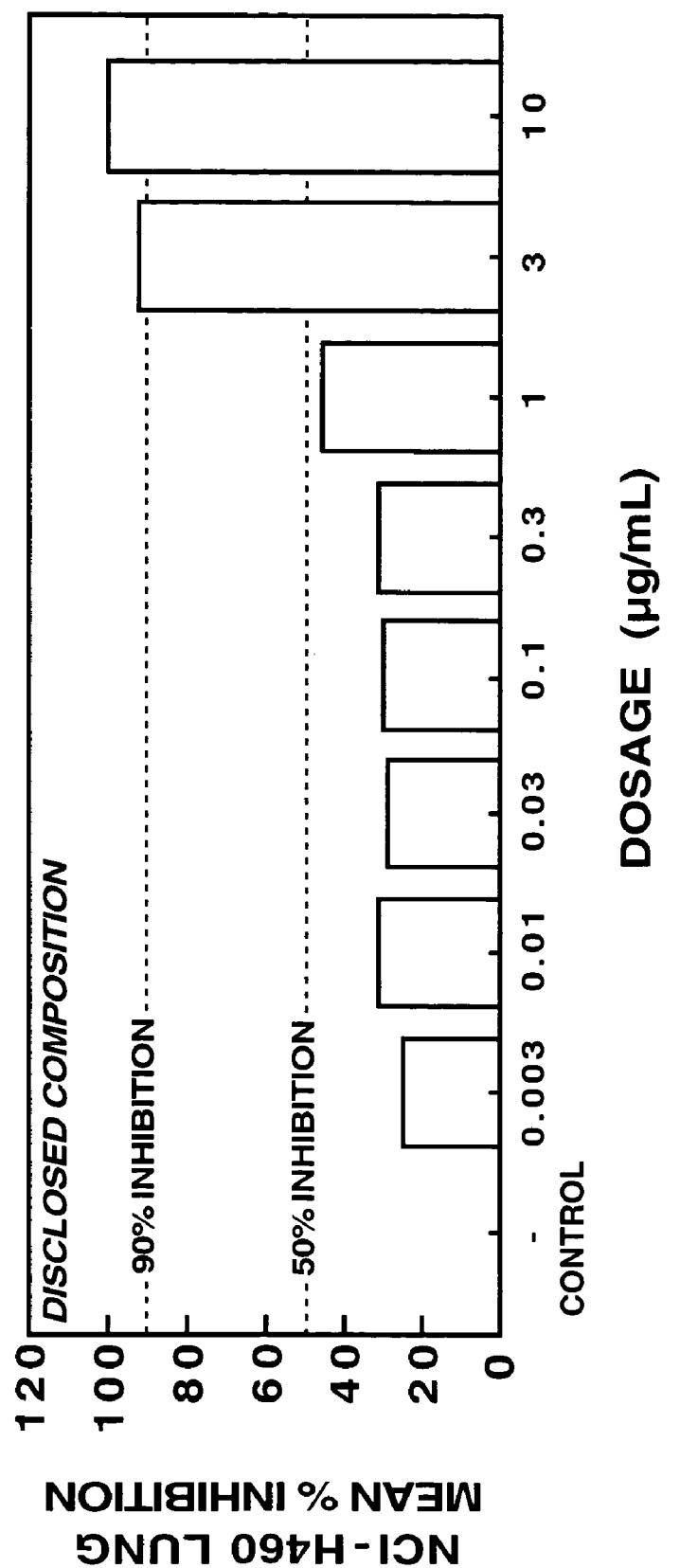
FIG. 3A is a graph of the concentration of the Composition alone plotted against NCI-H460 lung cells mean % inhibition.

FIG. 3A shows over 90% inhibition of NCI-H460 lung cells with the high activity and cytotoxicity of the disclosed Composition at a 10 µg/mL concentration. The disclosed Composition was also highly effective at a 3 µg/mL concentration with a 90% inhibition rate and nearly 50% inhibition of the cells at only a 1 µg/mL concentration. The disclosed Composition also exhibited significant inhibition percentages at very low dosages. FIG. 3B provides the absorbance value units from the varying dosages, as shown, as well as the inhibition percentages for the different dosages, which were very high. FIG. 3C discloses the $IC_{50}$ at a low dosage of 1.183 µg/mL of the Composition, and the statistical analysis of the regression output.

Figure 3D:
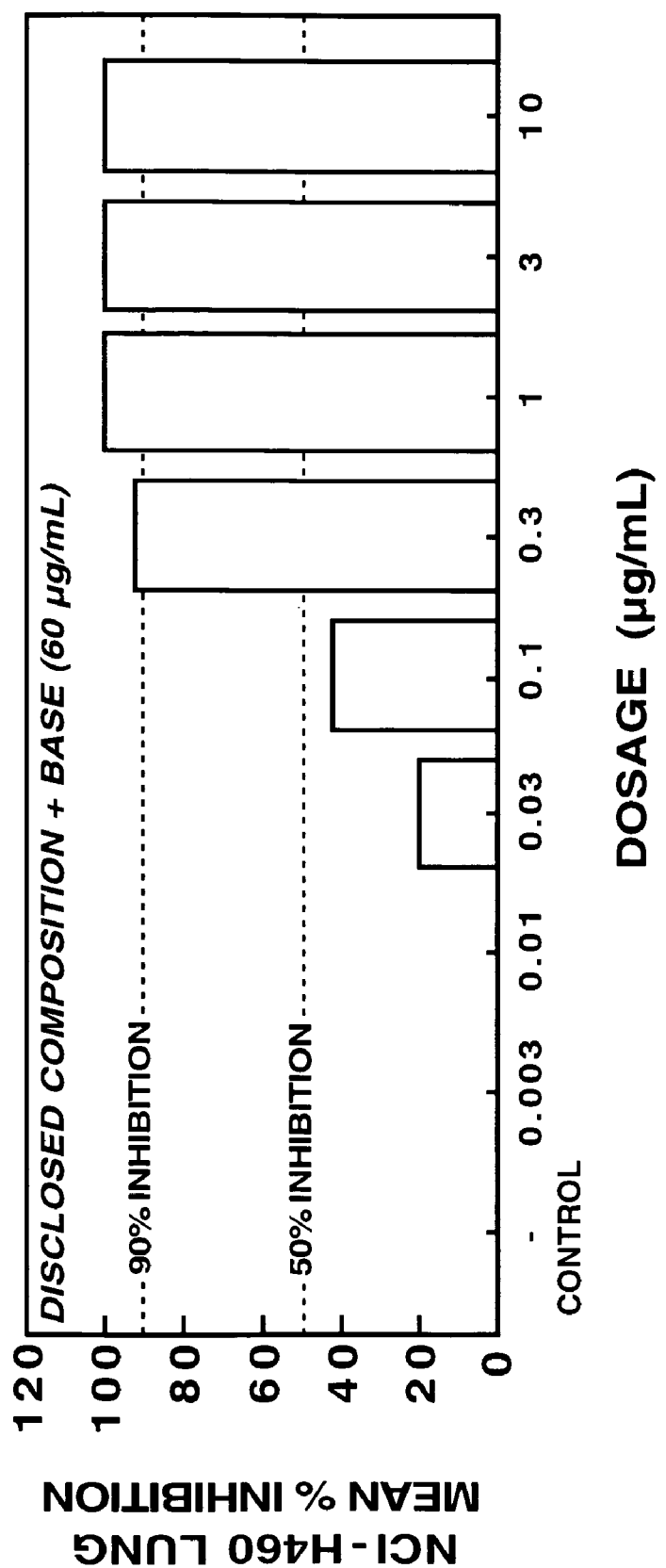
FIG. 3D is a graph of the concentration of the Composition plus Base Compound plotted against NCI-H460 lung cells mean percent inhibition.

This example examines the effect of toxicity of the Composition plus the Base Compound against NCI-H460 lung cells. The results of these tests are shown in FIGS. 3D, 3E and 3F. FIG. 3D shows an enhanced cell kill of the NCI-H460 lung cells where the Base Compound is added to the disclosed Composition, as compared to the results of the Composition itself. As shown in FIG. 3A, 10 µg/ml of the Composition were applied for a resulting 100% cell kill. Where the Base Compound was added to the Composition, 1 µg/ml of Composition plus Base Compound resulted in a 100% cell kill, as shown in FIG. 3D. The concentration of Composition plus Base Compound was a very efficient 0.131 µg/ml resulting in an $IC_{50}$ inhibition, and by contrast, the concentration of the Composition alone was 1.183 µg/ml to resulting in an $IC_{50}$ inhibition of the experimental cells. FIG. 3E discloses the absorbance value units from the varying dosages, as shown, as well as the inhibition percentages for the different dosages, which were very high. The combination of the Composition with the Base Compound was shown to be highly effective in its toxic activity against NCI-H460 Lung cells.

Example 5

Figure 4A:
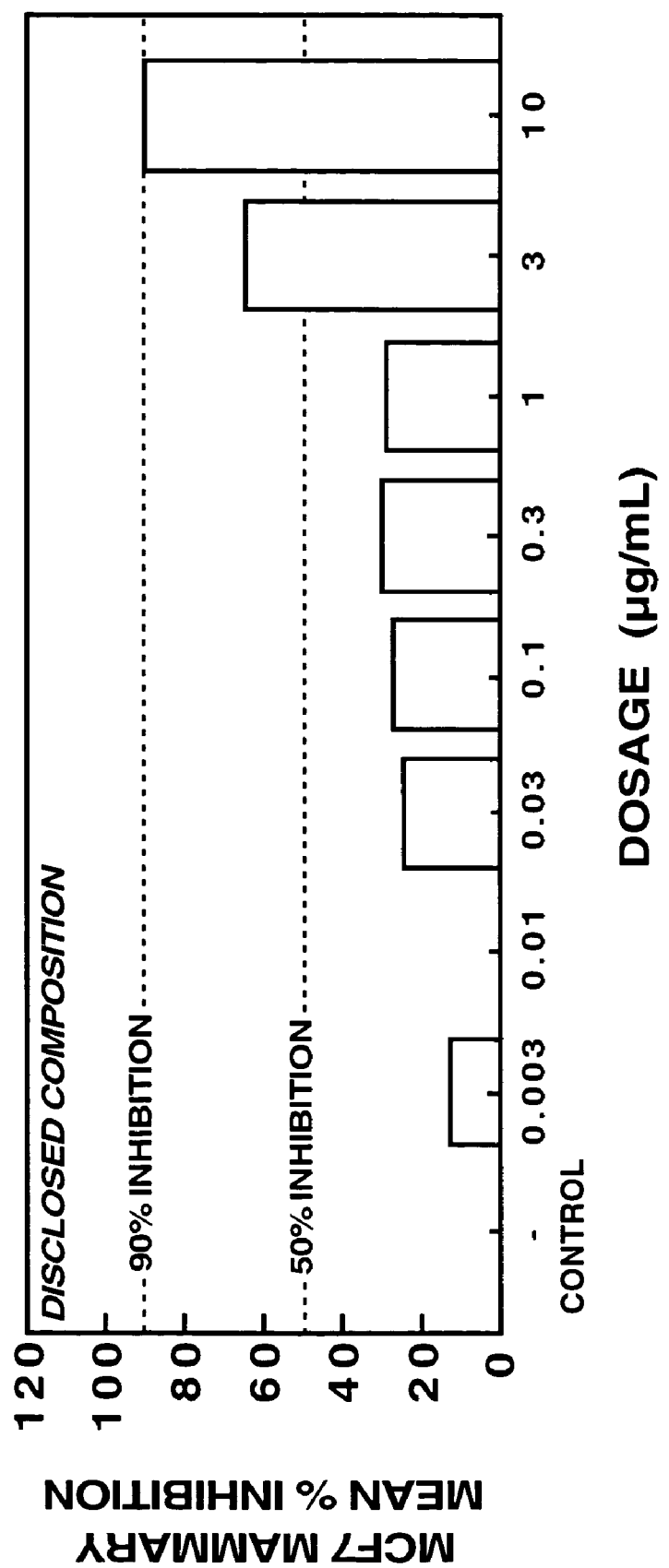
FIG. 4A is a graph of the concentration of the Composition alone plotted against MCF7 mammary cells mean percent inhibition.

This example examines the effect of toxicity of the Composition alone against MCF7 mammary cells. FIG. 4A shows the very high activity of the disclosed Composition against MCF7 mammary cells. The Composition exhibited over 90% inhibition of the cells at 10 µg/mL, and over 60% inhibition at 3 µg/mL. FIG. 4B provides the absorbance values for disclosed Composition, plus the media and MTS. FIG. 4C provides the calculated $IC_{50}$ of 2.213 µg/mL, and the regression output for 3.000 and 1.000 concentrations.

Figure 4D:
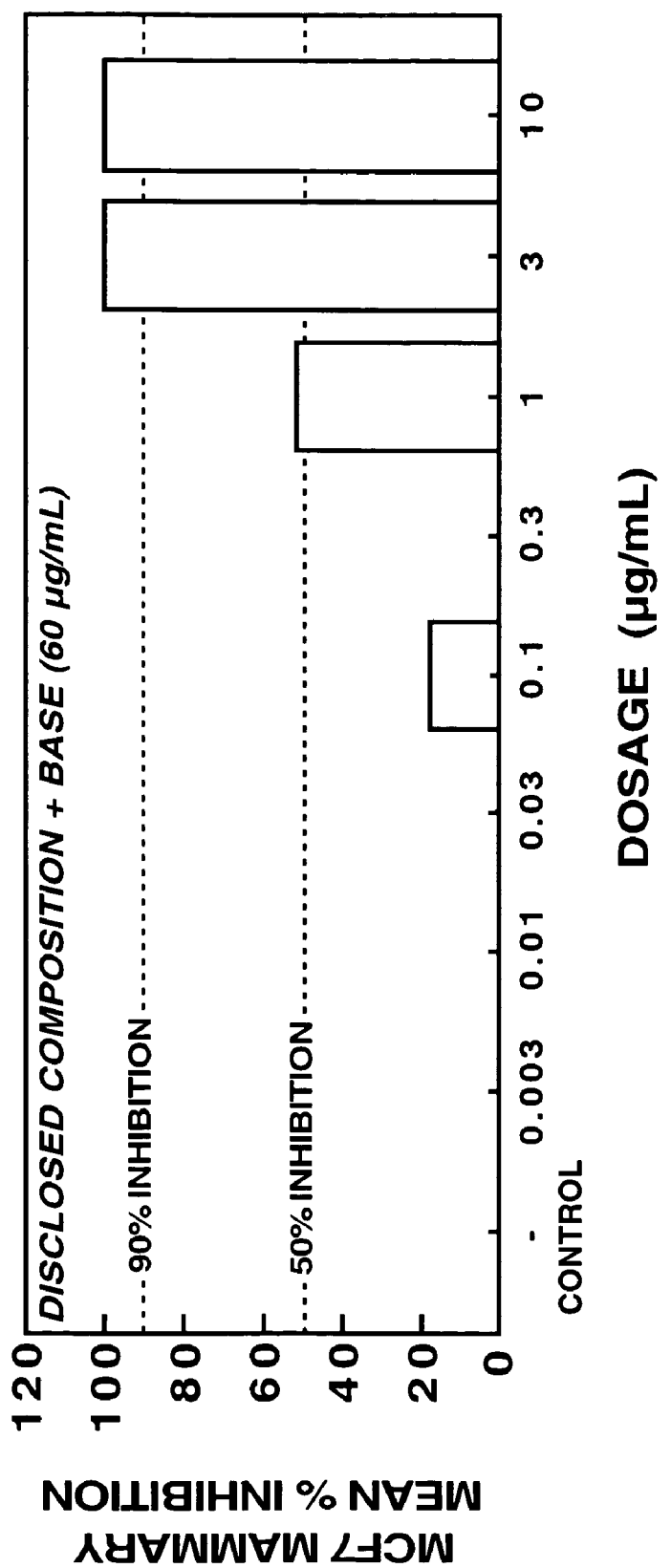
FIG. 4D is a graph of the concentration of the Composition plus Base Compound plotted against MCF7 mammary cells mean % inhibition.

FIGS. 4D, 4E and 4F examine the effect of toxicity of the Composition in combination with the Base Compound against MCF7 mammary cells. These tests show an enhanced cell kill with the addition of the Base Compound to this cell line, as compared to the disclosed Composition only, as shown in FIGS. 4A, 4B, and 4C. FIG. 4A shows that 10 µg/ml were required for 90% cell kill. When tested in combination with the Base Compound, only 3 µg/ml of the Composition is required for 100% of cell kill, which lowered the $IC_{50}$ to 0.972 µg/ml for the same cell line.

Example 6

Figure 5A:
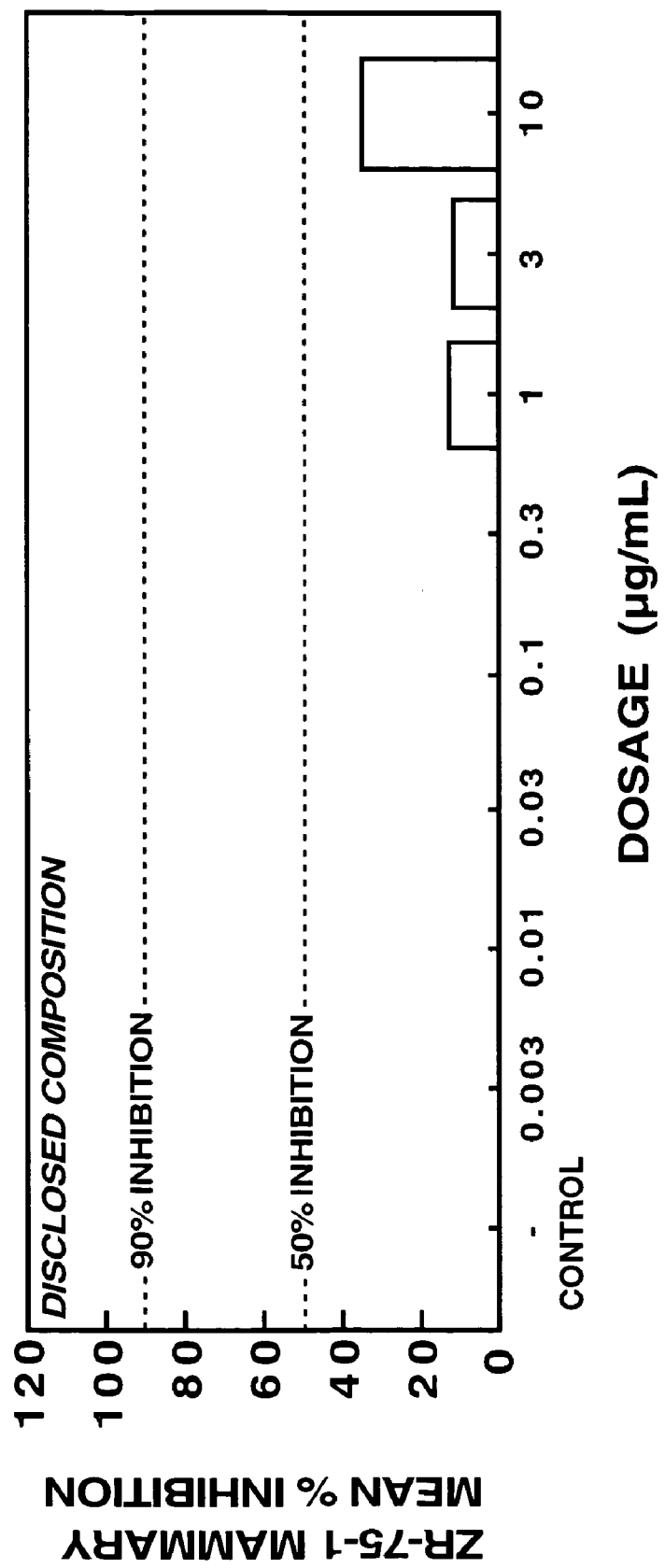
FIG. 5A is a graph of the concentration of the Composition alone plotted against ZR-75-1 mammary cells mean percent inhibition.

FIG. 5A graphs the effect of toxicity of the disclosed Composition against ZR-75-1 mammary cells. These tests showed an approximately 35% inhibition at 10 µg/mL of the ZR-75-1 mammary cells. This cell line showed resistance to the Composition at concentrations up to approximately 10 µg/ml. The absorbance values and inhibition percentages are shown in FIGS. 5B and 5C.

Figure 5D:
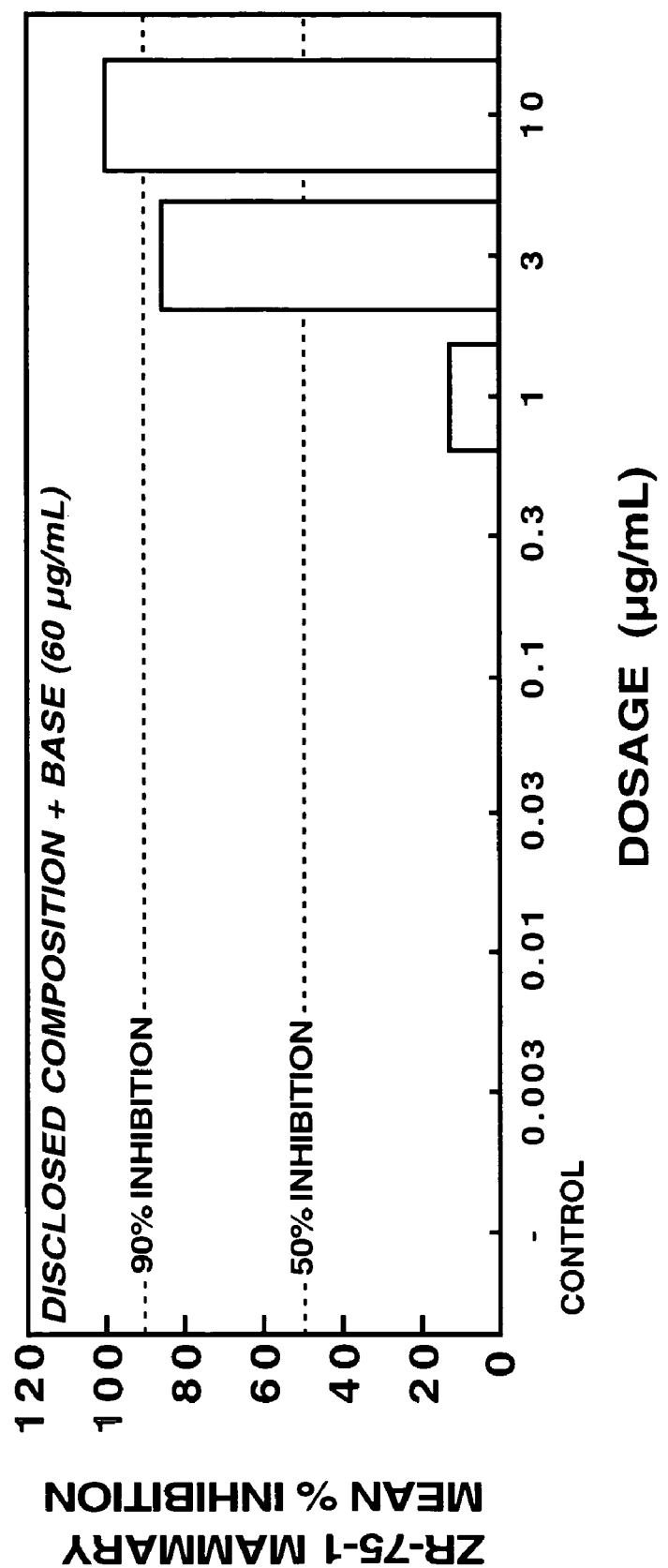
FIG. 5D is a graph of the concentration of the Composition plus Base Compound plotted against ZR-75-1 mammary cells mean % inhibition.

FIG. 5D discloses the very high activity of the combination of the disclosed Composition and the Base Compound against the ZR-75-1 mammary cells. The $IC_{50}$ of this combination was found to be a surprising concentration and calculated to approximately 2.031 µg/mL. The resistance of ZR-75-1 mammary cells was essentially eliminated with the addition of the Base Compound to the Composition. The 10 µg/ml of the Composition plus the Base Compound resulted in an approximately 100% cell kill for this cell line, a very effective therapeutic with few side effects or negative aspects. FIG. 5E provides the absorbance values and inhibition percentages of this experiment with significant inhibition at 3 µg/ml and 10 µg/ml dosages. FIG. 5F discloses a calculated $IC_{50}$ rate of a low concentration of approximately 2.031 µg/ml, and the regression output for the experiment.

Example 7

Figure 6A:
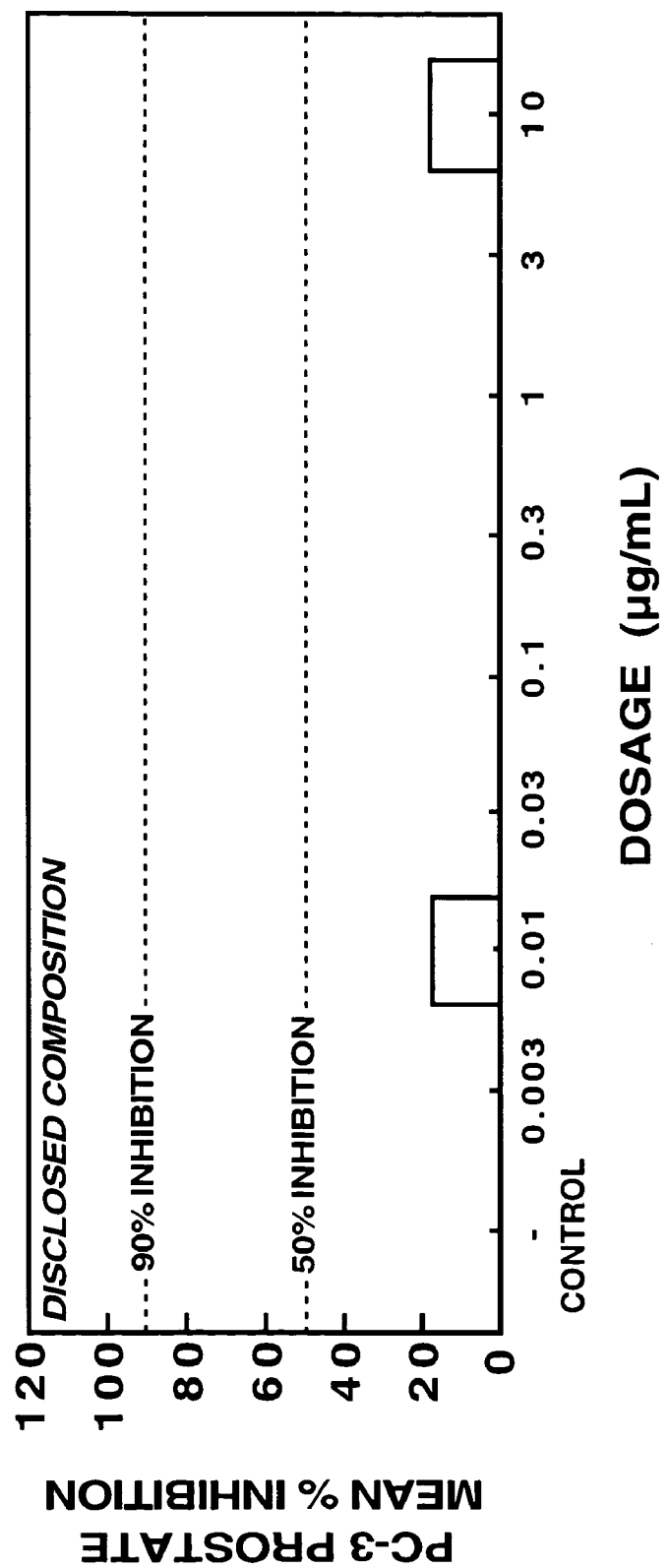
FIG. 6A is a graph of the concentration of the Composition alone plotted against PC-3 prostate cells mean percent inhibition.

FIG. 6A shows the results of toxicity tests of the Composition on PC-3 prostate cells. The PC-3 prostate cells exhibited resistance to the Composition up to concentrations of approximately 10 µg/mL, with some cellular inhibition at 0.01 µg/mL. The dosage of 10 µg/mL resulted in a 17% inhibition of the prostate cells. FIGS. 6B and 6C provide the absorbance values and statistical results of the experiment of Composition on prostate cells.

Figure 6D:
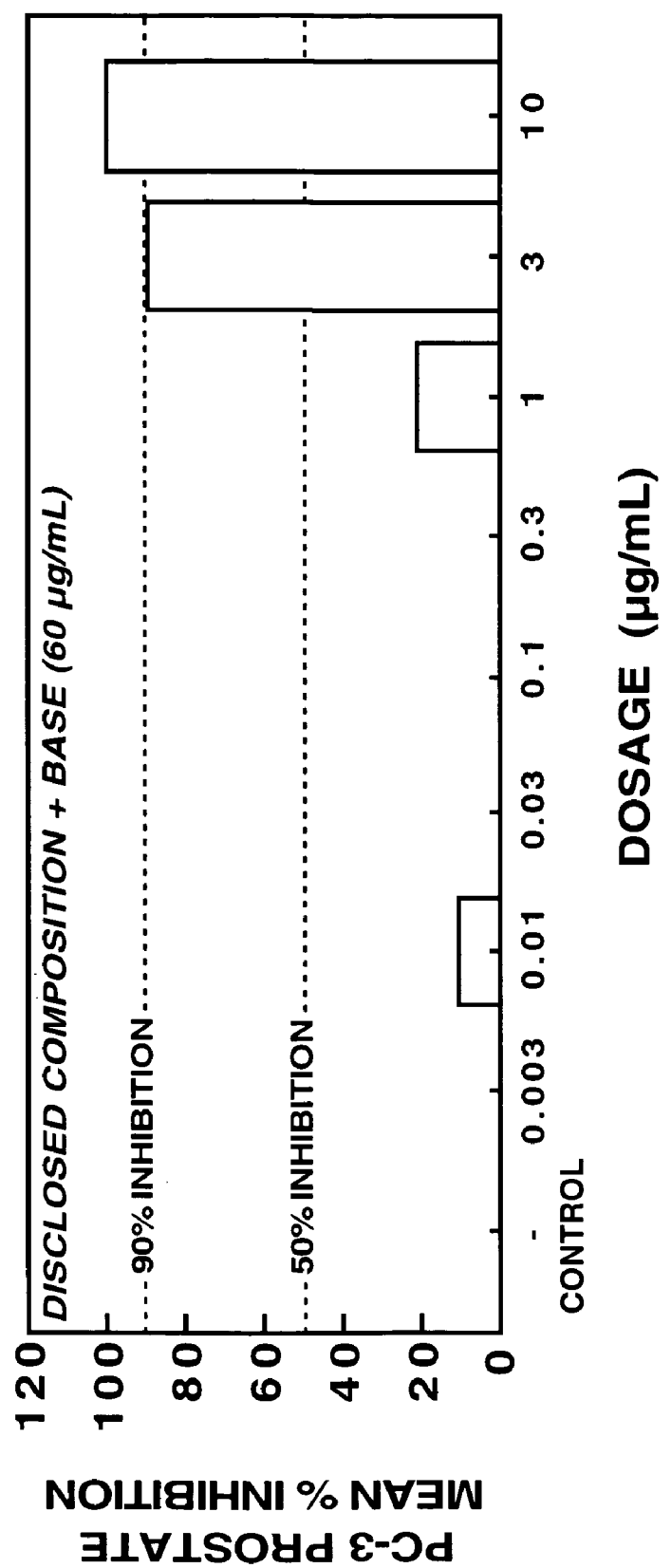
FIG. 6D is a graph of the concentration of the Composition plus Base Compound plotted against PC-3 prostate cells mean % inhibition.

FIG. 6D shows the effects of toxicity of the Composition plus the Base Compound against PC-3 prostate cells. The resistance of PC-3 prostate cells is essentially eliminated with the addition of Base Compound. The addition of the Base Compound shows an enhanced cell kill in these tests to this cell line, as compared to the Composition alone in FIG. 6A. A concentration of 10 µg/ml of Composition in combination with the Base Compound resulted in a 100% of cell kill, with an $IC_{50}$ that was extremely low at a concentration of 1.869 µg/ml. Concentrations as low as 3 µg/ml resulted in approximately 90% inhibition of the cell line. FIGS. 6E and 6F provide the absorbance value and statistical results of this experiment.

The cause of the aberrant experimental results found in both FIGS. 6A and 6D at the 0.01 µg/ml concentration level was not determined.

Example 8

Figure 7A:
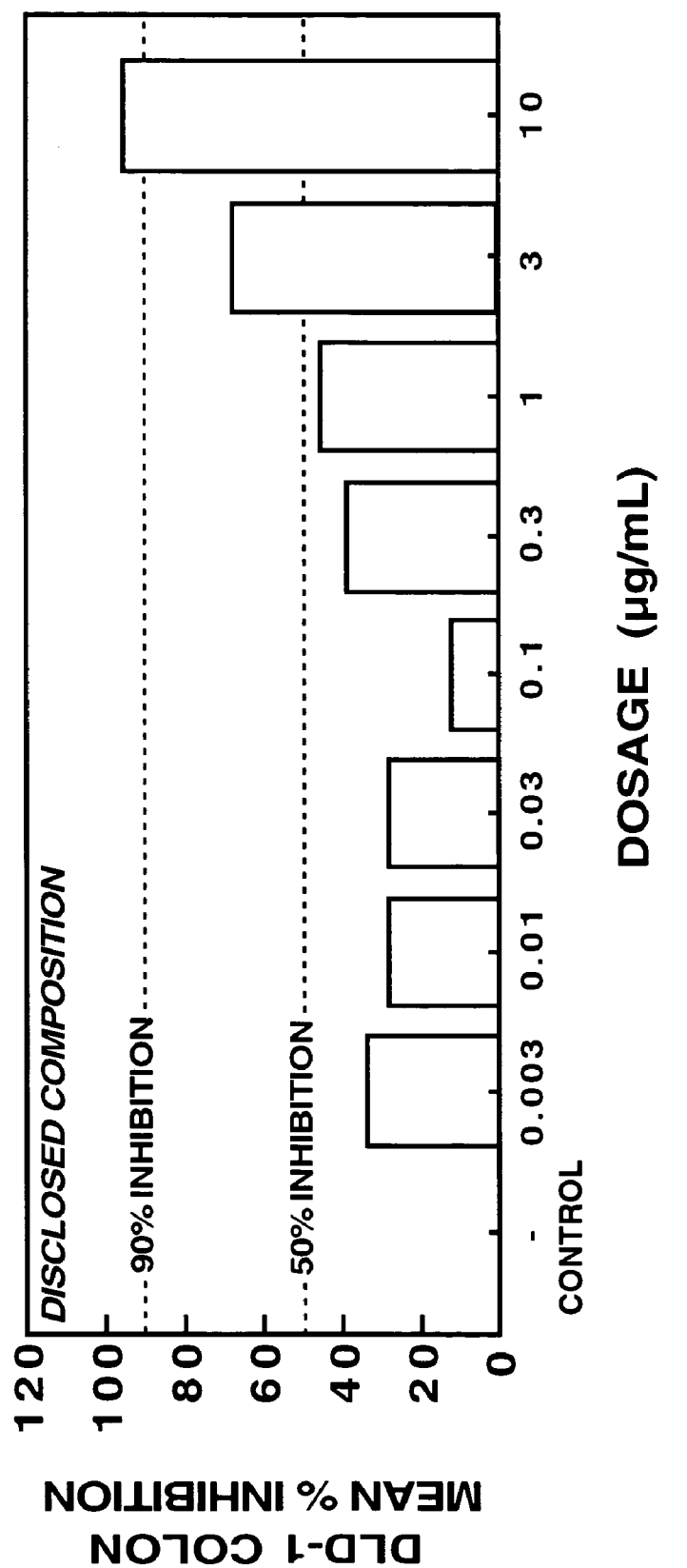
FIG. 7A is a graph of the concentration of the Composition alone plotted against DLD-1 colon cells mean percent inhibition.

FIG. 7A shows the high toxicity effect of the Composition on DLD-1 colon cells. The Composition displayed significant cell kill rates at all concentrations, including at very low concentrations. The resulting inhibition percentages, as shown in FIG. 7B, were very high with a 95% inhibition of the DLD-1 colon cells with 10 µg/mL of the Composition. FIG. 7C provides the statistical analysis of the experimental results.

Figure 7D:
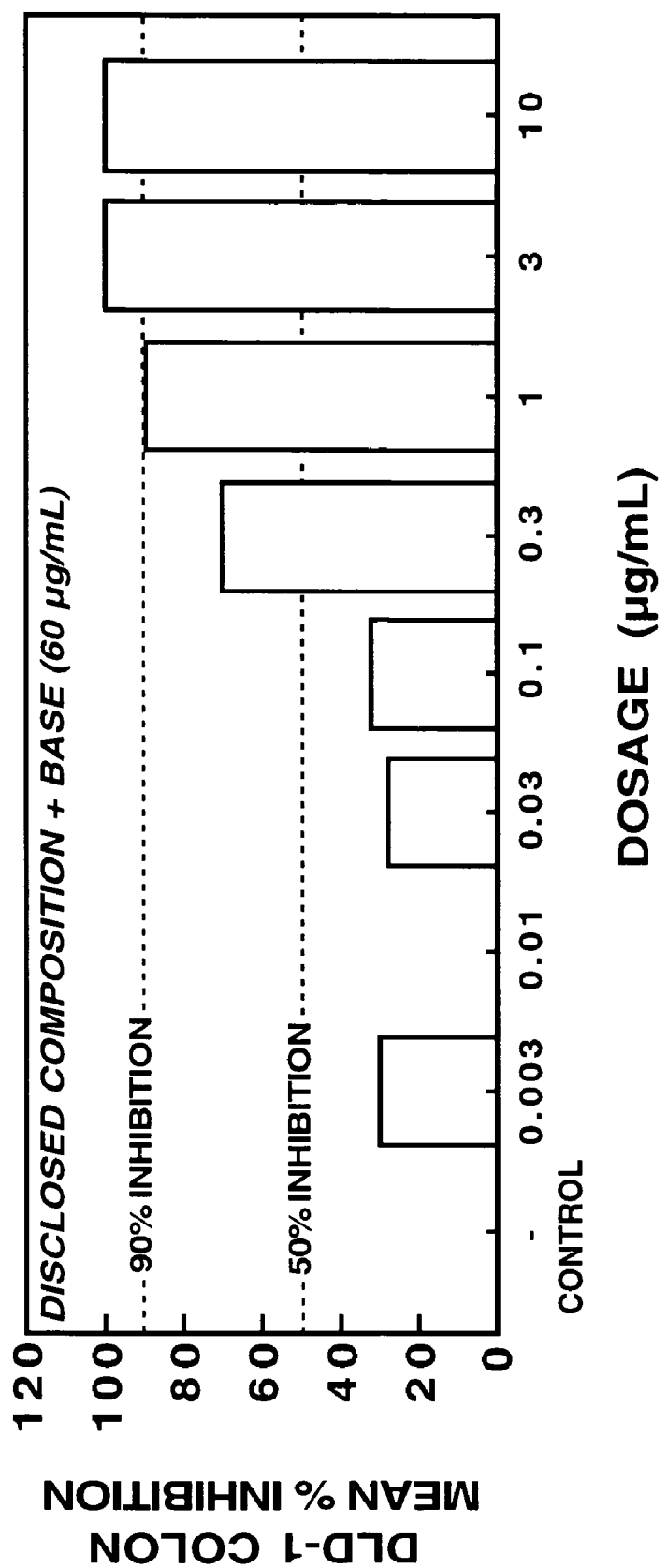
FIG. 7D is a graph of the concentration of the Composition plus Base Compound plotted against DLD-1 colon cells mean % inhibition.

FIG. 7D provides the results of toxicity experiments with the Composition in combination with the Base Compound on DLD-1 colon cells. These tests showed an enhanced cell kill with the addition of Base Compound as compared to the Composition alone. As shown in FIGS. 7D and 7E, an exceedingly low concentration of 3 µg/ml of Composition plus Base Compound was required for 100% of cell kill, as compared to a 95% cell kill by 10 µg/ml of the Composition alone, shown in FIGS. 7A and 7B. The $IC_{50}$ was lowered with the addition of Base Compound for the same cell line to 0.196 µg/ml from an $IC_{50}$ of 1.430 µg/ml for the Composition alone.

Example 9

Figure 8A:
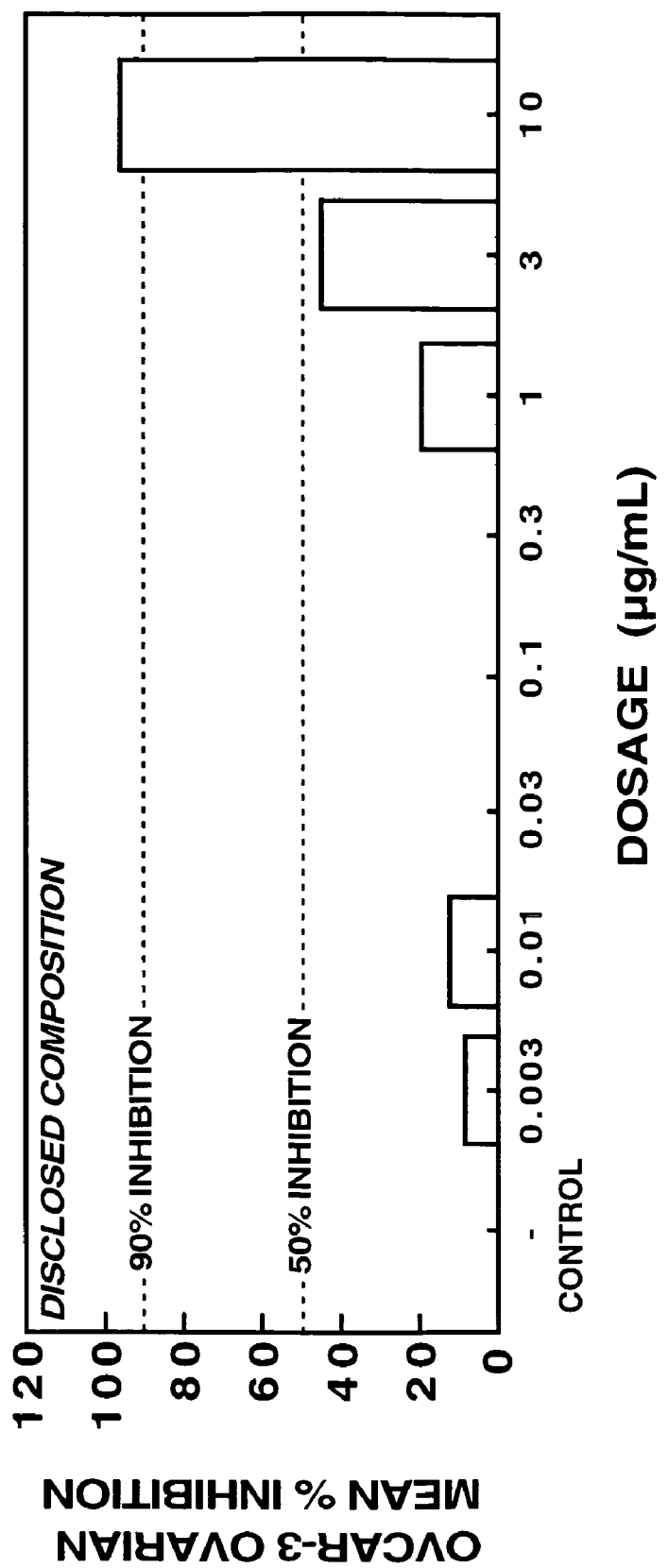
FIG. 8A is a graph of the concentration of the Composition alone plotted against OVCAR-3 ovarian cells mean percent inhibition.

FIG. 8A discloses the highly toxic effect of the Composition against OVCAR-3 ovarian cells with over 90% inhibition rate at very low concentrations of 1 µg/mL, 3 µg/mL and 10 µg/mL. The absorbance values and statistical results of these experiments are given in FIGS. 8B and 8C.

Figure 8D:
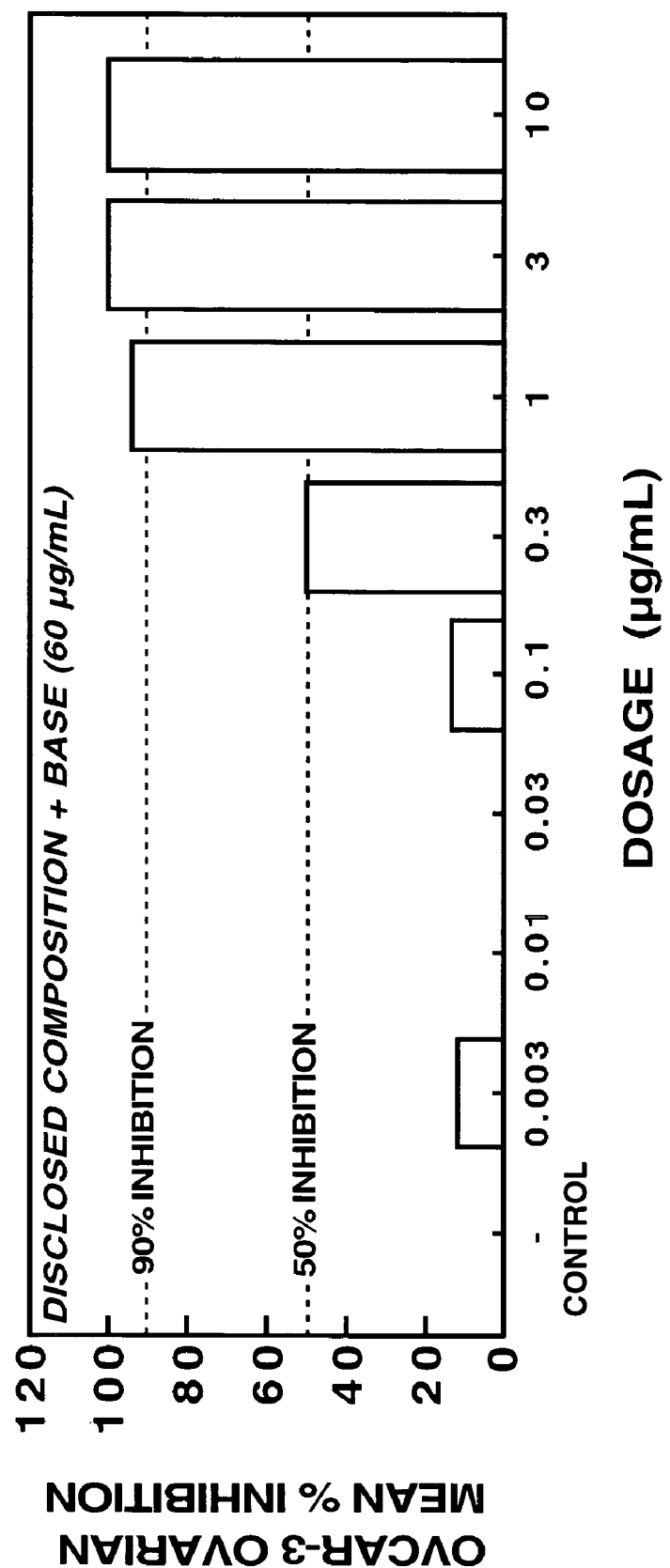
FIG. 8D is a graph of the concentration of the Composition plus Base Compound plotted against OVCAR-3 ovarian cells mean % inhibition.

The toxicity effects of the Composition in combination with the Base Compound on OVCAR-3 ovarian cells are shown in FIG. 8D. These tests showed an enhanced cell kill with the addition of the Base Compound as compared to Composition alone. The combination of the Composition with the Base Compound resulted in a 100% cell kill at the concentration of 3 µg/ml, whereas the application of the Composition alone required 10 µg/ml for a resulting 95% cell kill. The $IC_{50}$ for the combination of the Composition and the Base Compound was lowered to the very low concentration of 0.299 µg/mL.

Example 10

Figure 9A:
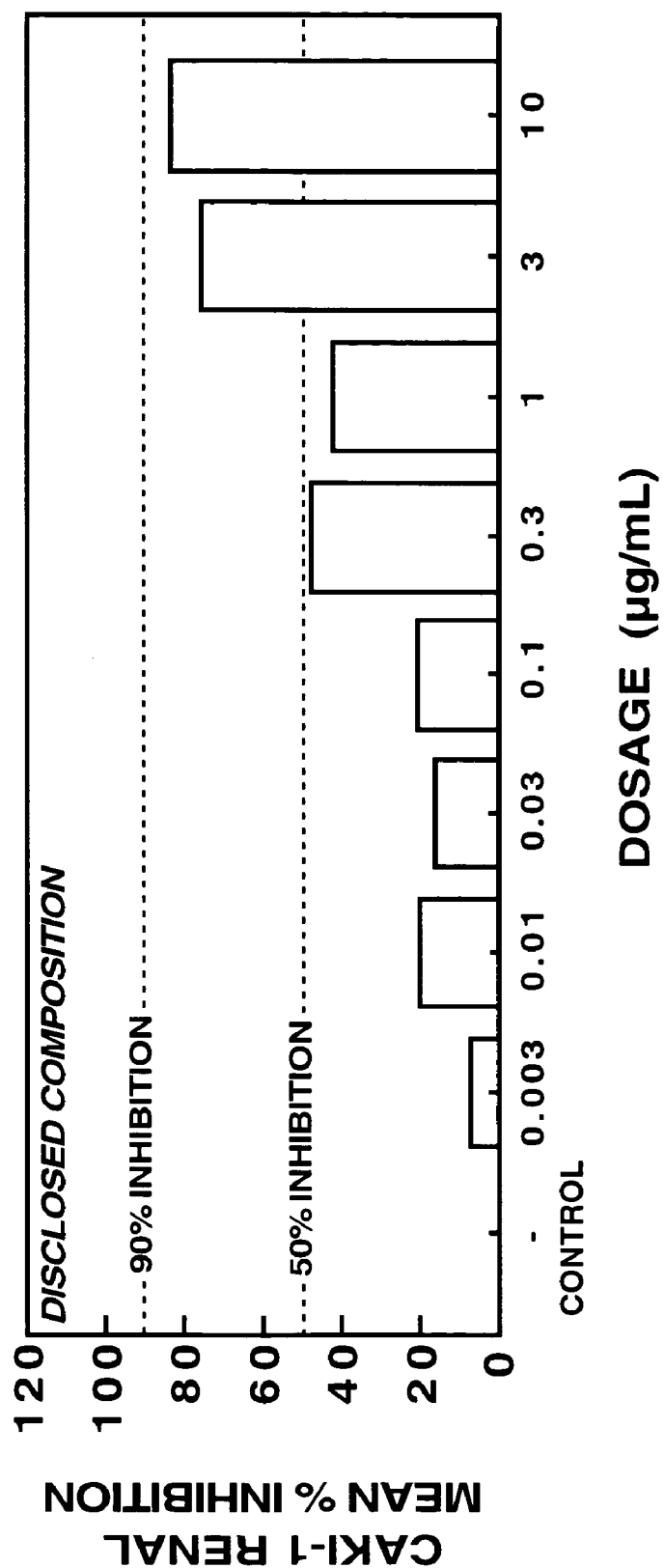
FIG. 9A is a graph of the concentration of the Composition alone plotted against CAKI-1 renal cells mean percent inhibition.

The toxicity effects of the Composition on CAKI-1 renal cells are shown in FIG. 9A. The Composition showed very high activity against this cell line, even at low dosages. The inhibition percentages showed significant activity of the Composition at concentrations as low as 0.01 µg/mL for 20.3% inhibition, and 83.6% inhibition of the cell line at the concentration of 10 µg/ml. See, FIGS. 9B and 9C.

Figure 9D:
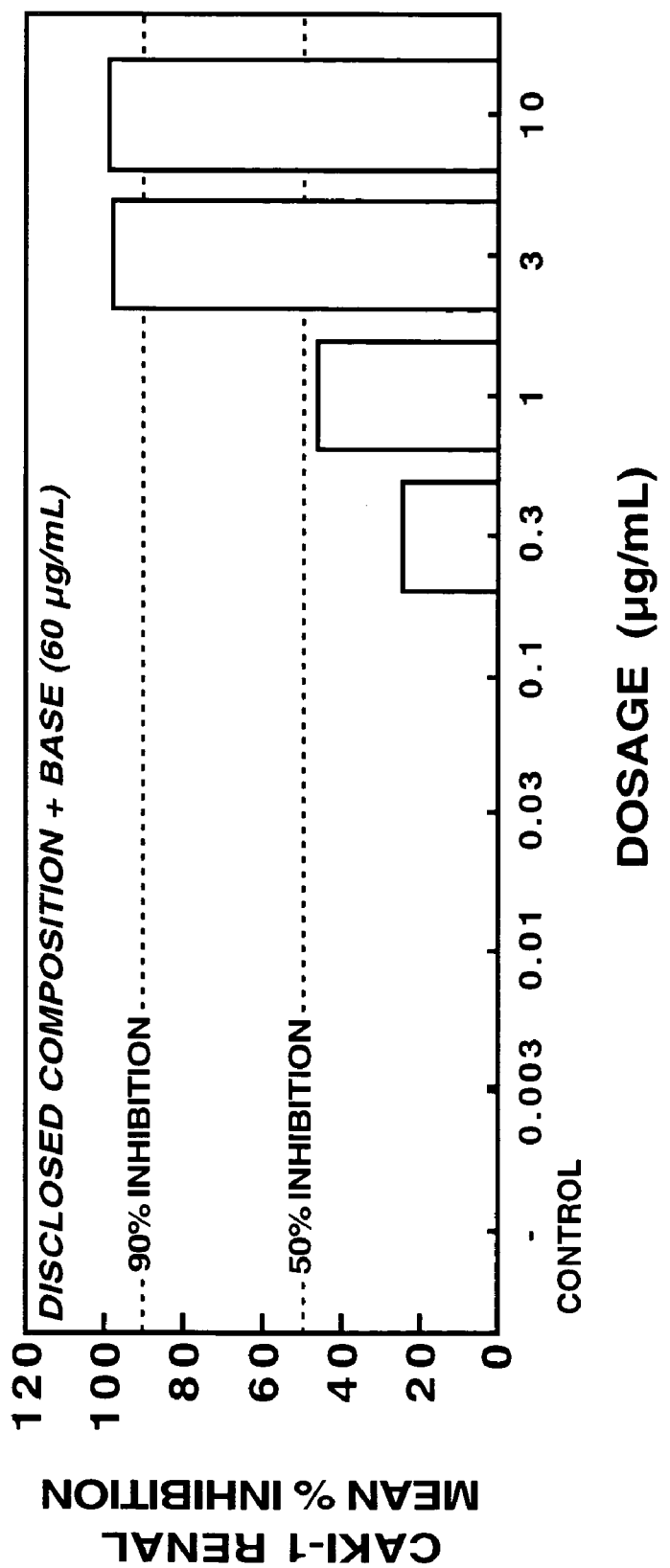
FIG. 9D is a graph of the concentration of the Composition plus Base Compound plotted against CAKI-1 renal cells mean % inhibition.

The combination of the Composition plus the Base Compound showed very high activity against CAKI-1 renal cells, as shown in FIG. 9D. These tests show an enhanced cell kill with the addition of Base Compound as compared to the use of the Composition alone as shown in FIG. 9A. A concentration of 10 µg/ml of the Composition resulted in a 99% cell kill. The $IC_{50}$ was lowered with the addition of Base Compound to 1.138 µg/mL for this cell line in contrast to the $IC_{50}$ of Composition alone, which was 1.44 µg/mL. In the experiments on the CAKI-1 renal cells, both the Composition and the Composition plus the Base Compound demonstrated very significant activity with low $IC_{50}$ rates.

Example 11

Figure 10A:
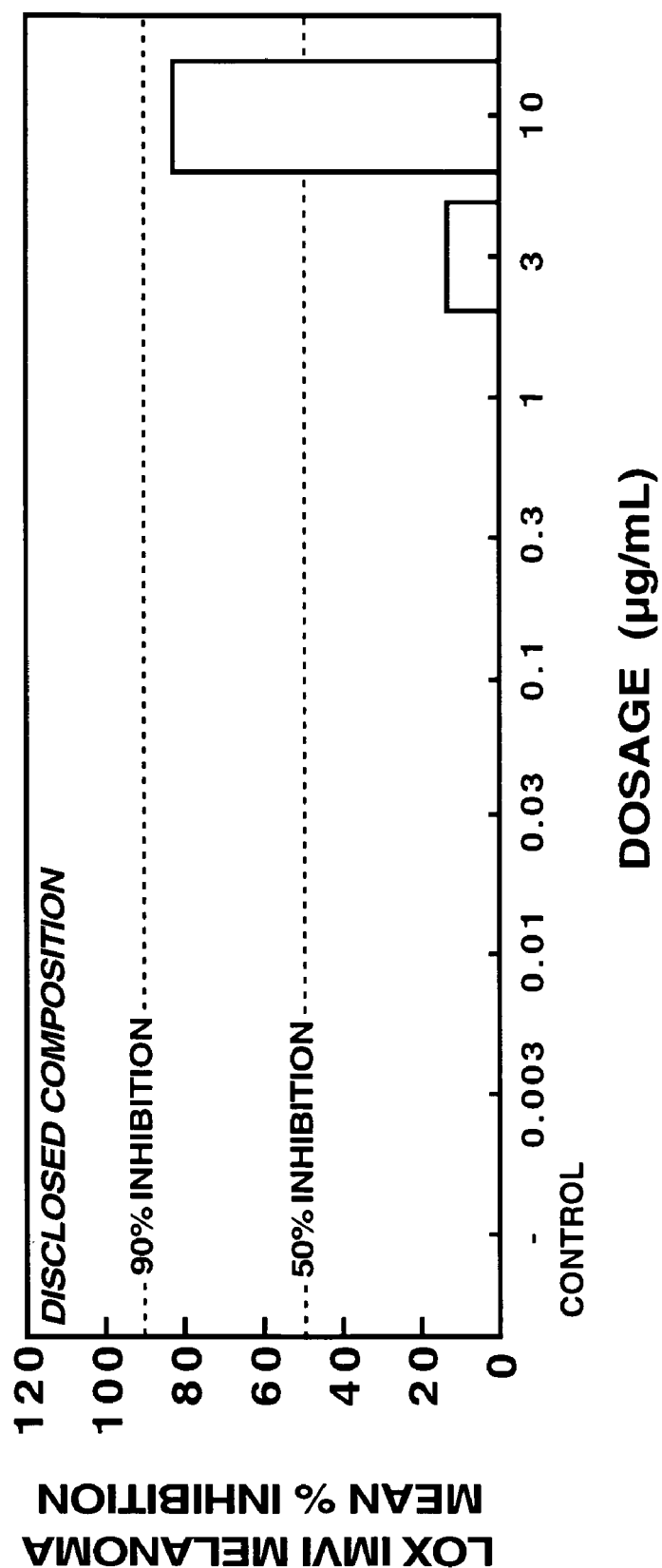
FIG. 10A is a graph of the concentration of the Composition alone plotted against LOX IMVI melanoma cells mean percent inhibition.

FIG. 10A shows the toxic effect the Composition against LOX IMVI melanoma cells. The experiment showed high activity of the Composition and resulted in an approximately 82% inhibition of the cell line at a concentration of 10 µg/mL. FIG. 10B shows the absorbance rates and the inhibition percentages of the experiments with some inhibition at 3 µg/mL. FIG. 10C provides the statistical analysis of the results, including a calculated $IC_{50}$ of 6.718 µg/mL.

Figure 10D:
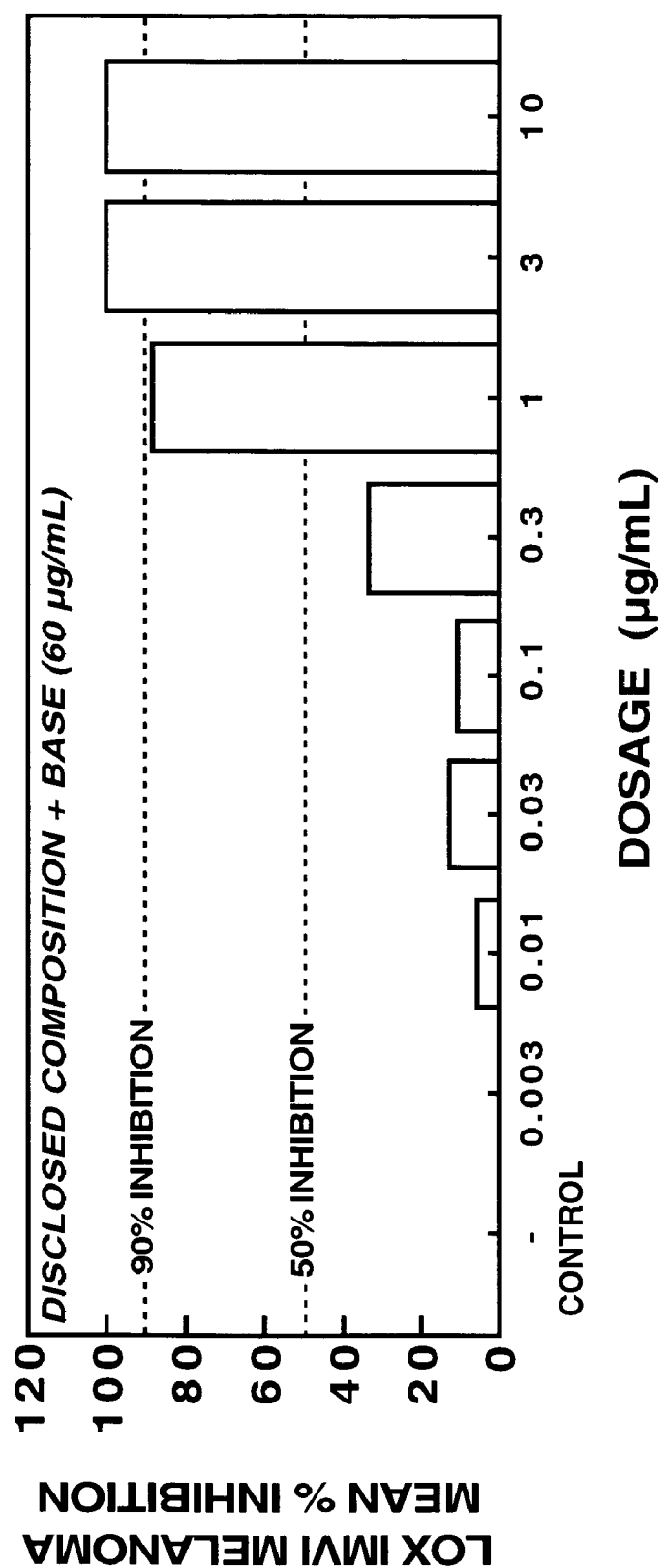
FIG. 10D is a graph of the concentration of the Composition plus Base Compound plotted against LOX IMVI melanoma cells mean % inhibition.

FIG. 10D shows the high activity of the Composition plus the Base Compound on LOX IMVI melanoma cells. The Composition in combination with the Base Compound had highly toxic effects on this cell line, including at very low dosages. These tests show an enhanced cell kill with the addition of Base Compound to this cell line as compared to the use of Composition alone, as shown in FIG. 10A. A 3 µg/ml concentration of the Composition resulted in 100% cell kill, whereas 10 µg/ml were required for 82% cell kill with the Composition alone, as shown as FIG. 10A. The $IC_{50}$ of Composition alone was 6.718 µg/mL, the $IC_{50}$ was lowered with the addition of the Base Compound for the same cell line to 0.513 µg/mL.

Example 12

Figure 11A:
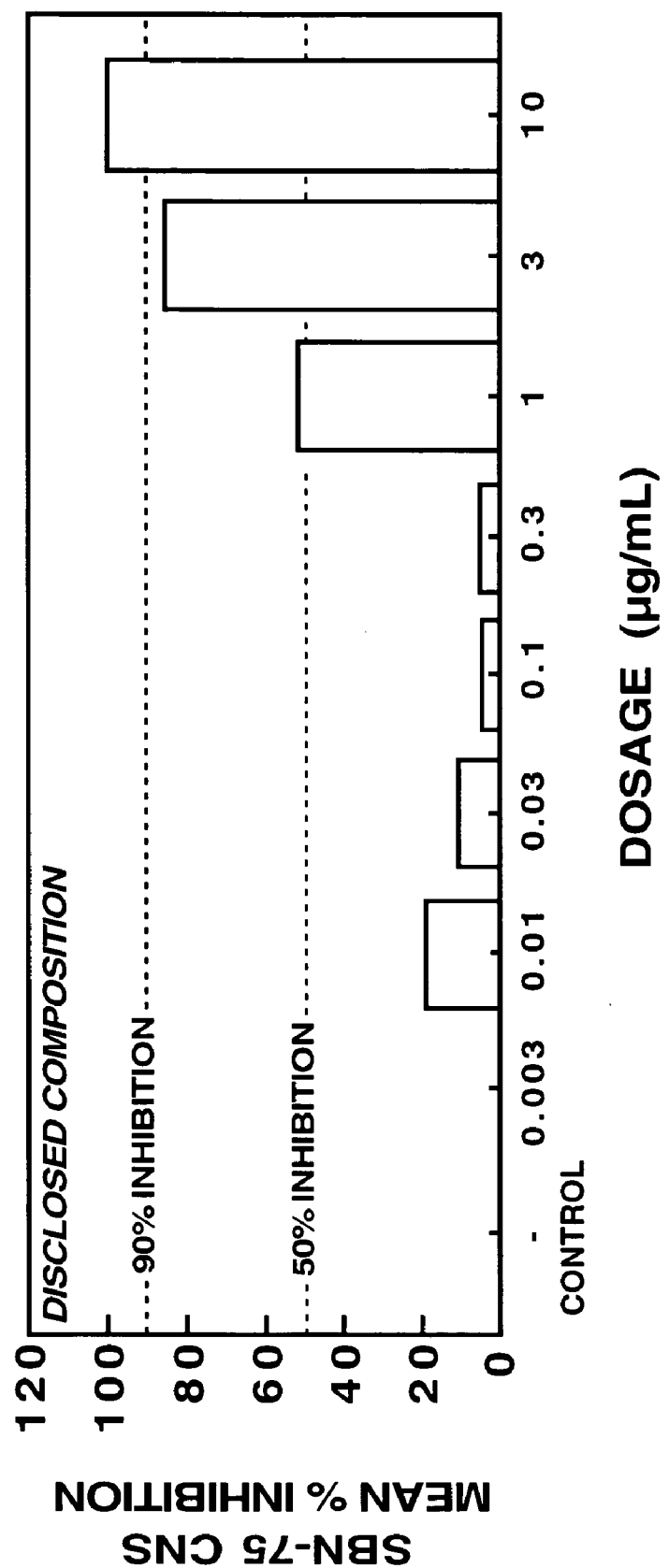
FIG. 11A is a graph of the concentration of the Composition alone plotted against SBN-75 CNS cells mean percent inhibition.

The toxicity of the Composition was tested against SBN-75 CNS cells. The results are shown in FIG. 11A, and show very high activity of the Composition. A concentration of 10 µg/mL resulted in a 100% inhibition of the SBN-75 CNS cells, and a concentration of only 3 µg/mL resulted in an approximately 85% inhibition of this cell line. FIGS. 11B and 11C provide the absorbance values and the statistical analysis of the results.

FIG. 11D discloses the high toxicity effects of the Composition plus the Base Compound against SBN-75 CNS cells. The combination of the Composition and the Base Compound resulted in a very successful 100% inhibition rate at dosages of 1 µg/mL, 3 µg/mL, and 10 µg/mL. These tests show an enhanced cell kill with the addition of the Base Compound to this cell line as compared to the use of the Composition alone. A concentration of 1 µg/ml of Composition plus Base Compound resulted in 100% of cell kill, as compared to a concentration of 10 µg/ml of the Composition alone for 100% cell kill. The $IC_{50}$ was lowered with the addition of Base Compound for the same cell line to 0.095 µg/ml.

Example 13

The CEM-SS cells were obtained from the AIDS Research and References Reagent Repository (Bethesda, Md.). These cells were passaged in T-75 flasks in tissue culture media, which included RPMI 1640 medium (no phenol red), with 10% fetal bovine serum (heat inactivated), 2 mM L-glutamine, 100 U/mL penicillin, 100 µg/ml streptomycin, and 10 µg/ml gentamycin. One day preceding the tritated thymidine assay, the cells were split 1:2 to assure that they were in an exponential growth phase at the time of the cytotoxicty tests. On the day of the assay, the cells were collected by centrifugation, washed twice with tissue culture medium, above, and resuspended at $5 \times 10^4$ cells per mL, and resuspended in fresh tissue culture medium. The total cell and viability counting was performed with a hemacytometer. Cell viability prior to the assay was determined by trypan blue dye exclusion and exceeded, as it must 95%. Cultures were incubated for 6 days at 37° C., 5% $CO_2$.

Figure 12A:
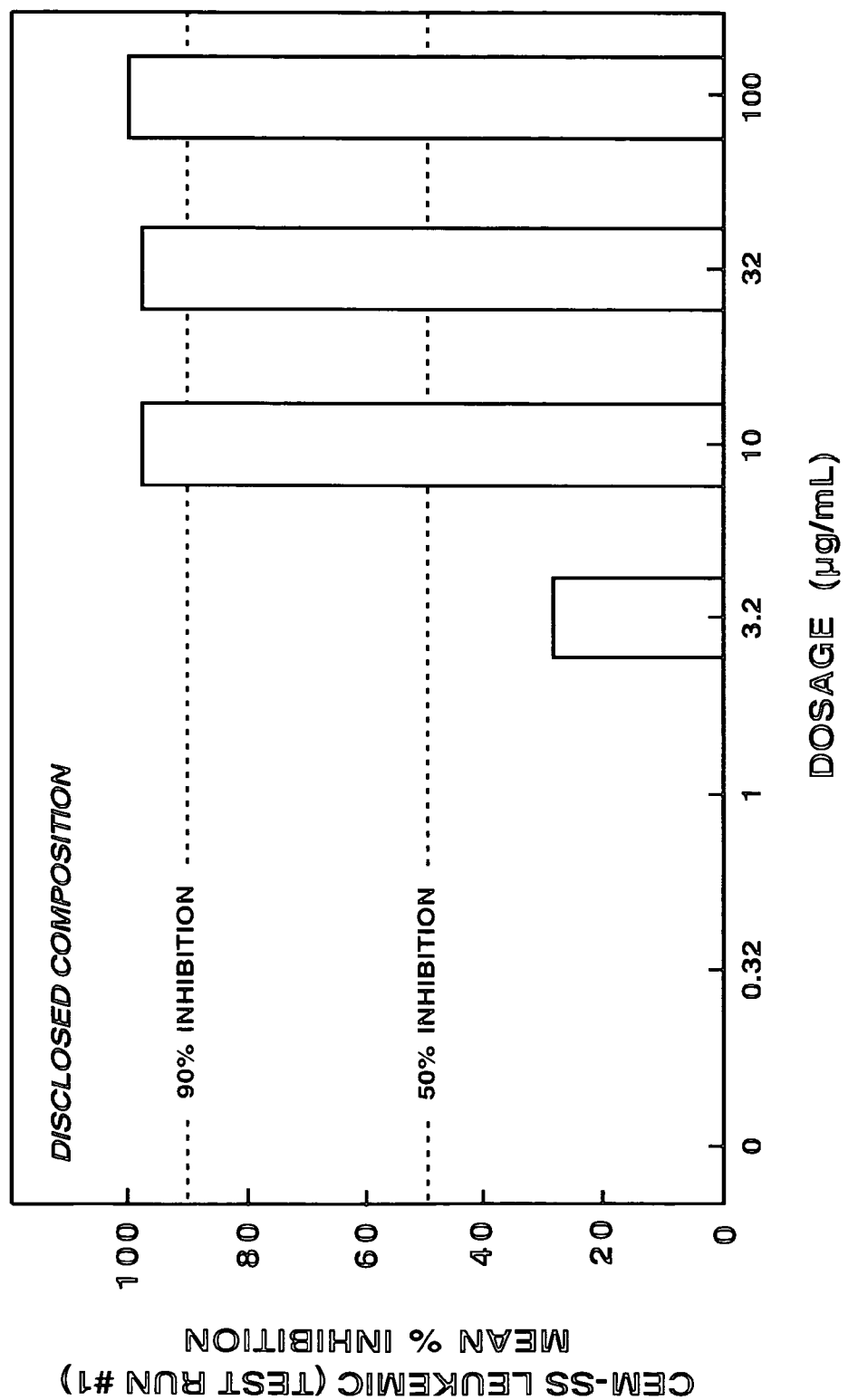
FIG. 12A is a graph of the concentration of the Composition alone plotted against CEM-SS Leukemic cells mean percent inhibition.

The highly toxic effects of the Composition alone against CEM-SS leukemic cells are shown in FIGS. 12A, 12B, 12C. These Figures show an $IC_{50}$ of 5.87 µg/mL and a highly efficient cell kill rate of approximately 98% at a dosage of 10 µg/mL.

Example 14

Figure 13A:
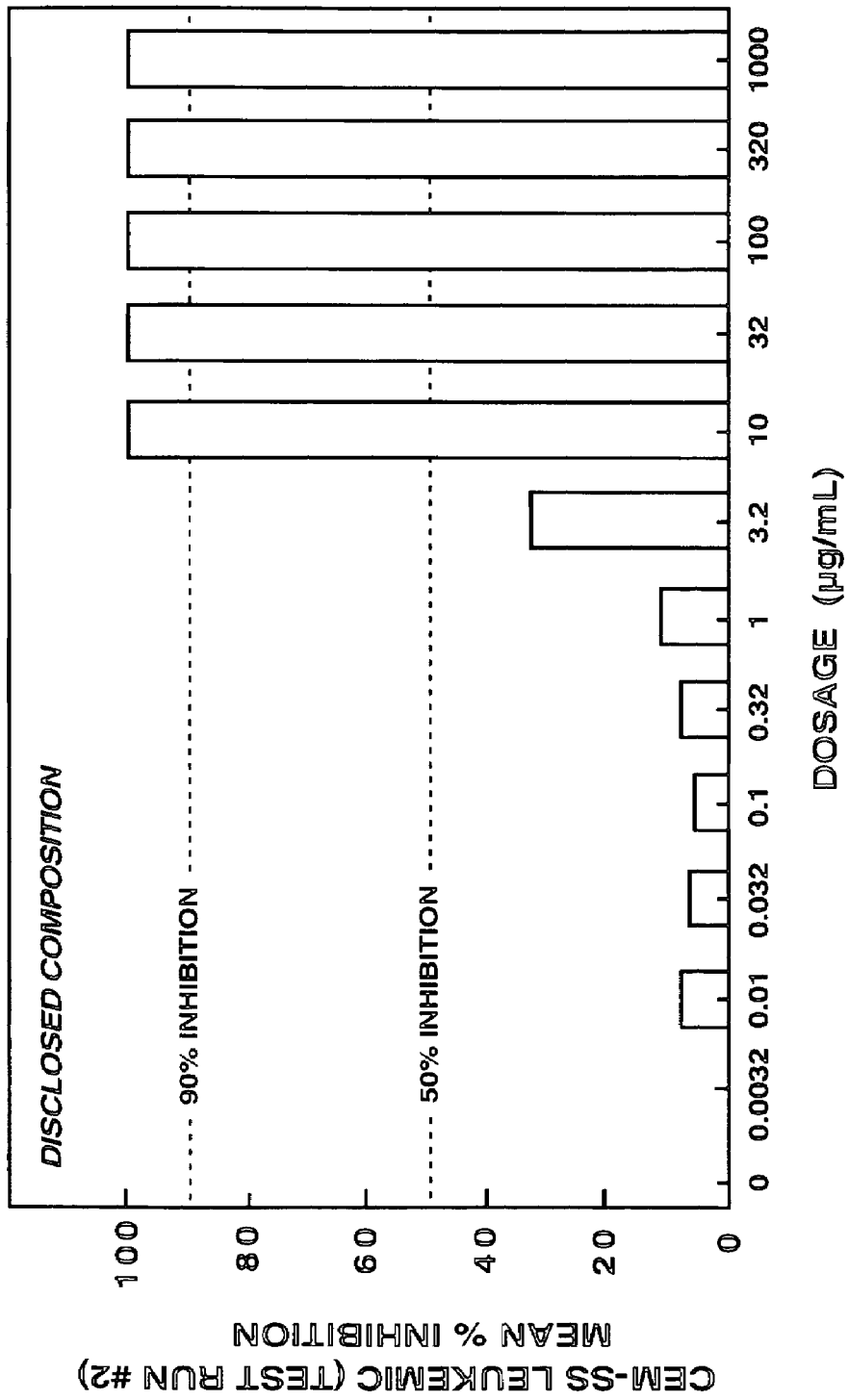
FIG. 13A is a graph of the concentration of the Composition alone plotted against CEM-SS leukemic cells mean percent inhibition.

The high activity of the Composition alone against CEM-SS leukemic cells are shown in FIGS. 13A, 13B, 13C. These Figures show $IC_{50}$ of 4.975 µg/mL and a highly efficient cell kill rate of approximately 100% at a dosage of 10 µg/mL.

In the foregoing description, certain terms are used to illustrate the preferred embodiments. However, no unnecessary limitations are to be construed by the terms used, since the terms are exemplary only, and are not meant to limit the scope of the present invention.

It is further known that other modifications may be made to the present invention, without departing from the scope of the invention, as noted in the appended Claims.

What is claimed is:

1. A method for treating cancer, cell proliferating diseases, solid tumors, liquid tumors, myelodysplasia disorders, hyper proliferative disorders, plasma cell dyscrasias and metastatic diseases in a patient comprising: forming a colloidal solution composition having a broad spectrum of anti-neoplastic properties, said composition having a core of at least a biologically acceptable copper compound, wherein said copper compound is a fixed copper compound selected from the group consisting of cupric hydroxide, copper oxide, copper oxychloride, cupric carbonate basic, copper sulfate basic, cuprous oxide, cupric hydroxide-iron hydroxide, copper-iron oxide, cupric citrate, cupric phosphate, cuprobam, indigo copper, minerals brochantite, langite, malachite, cornetite, libethenite, pseudolibethenite, pseudo-malachite, antlerite, covellite, marshite, cuprite, chalcocite, Rogojski's salt, brochantite, hydrocyanite, nantokite and dolerophane, said core being encapsulated, encoated, adsorbed, complexed or bound in at least one of a sheath, a shell, a polymeric shell, a cover, a casing, an encoating, a jacket or combination thereof, and a pharmaceutically acceptable carrier; said sheath, shell, polymeric shell, cover, casing, encoating, jacket or combination thereof being made of a material targeting cancer cells, cell proliferating disease cells, solid tumor cells, liquid tumor cells, myelodisplasia cells, hyper proliferative disorder cells, plasma cell dyscrasias cells or metastatic disease cells, and preventing immediate chemical interaction of the core with the surrounding environment; and administering the colloidal solution composition to a patient.

2. The method of claim 1, further comprising administering a redistribution agent selected from the group consisting of iron dextran and iron glucose at intervals of: after the administration of the composition; prior to the administration of the composition; co-administration with the composition or combinations thereof.

3. The method of claim 2, further comprising the loading of tissues and transferrin by the redistribution agent.

4. The method of claim 1, further comprising parenterally administering the composition to the patient.

5. The method of claim 1, further comprising orally administering the composition to the patient.

6. The method of claim 1, further comprising transdermally administering the composition to the patient.

7. The method of claim 1, further comprising inhalationally administering the composition to the patient.

8. The method of claim 1, further comprising administering the composition with an implantable polymer depot.

9. The method of claim 1, wherein the composition is administered for the total parenteral nutrition of a patient.

10. The method of claim 1, wherein the composition is administered with insulin potentiation therapy of a patient.

11. The method of claim 1, further comprising the addition of magnetic particles to the composition for imaging of cells.

12. A method for treating cancer, cell proliferating diseases, solid tumors, liquid tumors, myelodysplasia disorders, hyper proliferative disorders, plasma cell dyscrasias and metastatic diseases in a patient comprising: forming a colloidal solution composition having a broad spectrum of anti-neoplastic properties, said composition having a core of at least a biologically acceptable copper compound, wherein said copper compound is a fixed copper compound selected from the group consisting of cupric hydroxide, copper oxide, copper oxychloride, cupric carbonate basic, copper sulfate basic, cuprous oxide, cupric hydroxide-iron hydroxide, copper-iron oxide, cupric citrate, cupric phosphate, cuprobam, indigo copper, minerals brochantite, langite, malachite, cornetite, libethenite, pseudolibethenite, pseudo-malachite, antlerite, covellite, marshite, cuprite, chalcocite, Rogojski's salt, brochantite, hydrocyanite, nantokite and dolerophane, said core being encapsulated, encoated, adsorbed, complexed or bound in at least one of a sheath, a shell, a polymeric shell, a cover, a casing, an encoating, a jacket or combination thereof, and a pharmaceutically acceptable carrier, said sheath, shell, polymeric shell, cover, casing, encoating, jacket or combination thereof being made of a material targeting cancer cells, cell proliferating disease cells, solid tumor cells, liquid tumor cells, myelodisplasia cells, hyper proliferative disorder cells, plasma cell dyscrasias cells or metastatic disease cells, and preventing immediate chemical interaction of the core with the surrounding environment; and administering the colloidal solution composition to a patient and re-administering the composition at intervals based on results of the monitoring; further comprising administering a redistribution agent after the administration of the composition; prior to the administration of the composition; co-administration with the composition and combinations thereof, wherein said redistribution agent is selected from the group consisting of iron dextran and iron glucose.

13. The method of claim 12, further comprising the loading of tissues and transferrin by the redistribution agent.

14. The method of claim 12, further comprising parenterally administering the composition to the patient.

15. The method of claim 12, further comprising orally administering the composition to the patient.

16. The method of claim 12, further comprising transdermally administering the composition to the patient.

17. The method of claim 12, further comprising inhalationally administering the composition to the patient.

18. The method of claim 12, further comprising administering the composition with an implantable polymer depot.

19. The method of claim 12, wherein the composition is administered for the total parenteral nutrition of a patient.

20. The method of claim 12, wherein the composition is administered with insulin potentiation therapy of a patient.

21. The method of claim 12, further comprising the addition of magnetic particles to the composition for imaging of cells.

22. The method of claim 1 in which the sheath, shell, polymeric shell, cover, casing, encoating, jacket or combination thereof includes a substance selected from the group consisting of glucose, a saccharide, a polysaccharide, a carbohydrate, a protein, a dextran, a fat, a liposome, derivatives thereof or combinations thereof.

23. The method of claim 1 in which the core comprises nanoparticles covered by sheath material.

24. The method of claim 1 in which a biocompatible iron compound is used in conjunction with the core of at least a biologically acceptable copper compound.

25. The method of claim 24 in which the iron compound is selected from the group consisting of iron hydroxide, iron oxyhydroxide, iron oxide, iron glucose, ferric citrate, Ferritin, ferrous fumarate, ferrous sulfate, and iron saturated human holotransferrin.

* * * * *